(12) United States Patent
Dubrovsky et al.

(10) Patent No.: US 8,623,324 B2
(45) Date of Patent: Jan. 7, 2014

(54) LUMINESCENT DYES WITH A WATER-SOLUBLE INTRAMOLECULAR BRIDGE AND THEIR BIOLOGICAL CONJUGATES

(75) Inventors: Timothy Dubrovsky, Davis, CA (US); Barnaby Abrams, San Carlos, CA (US); Zhenjun Diwu, Sunnyvale, CA (US); Qinglin Meng, Sunnyvale, CA (US); Jinfang Liao, Foster City, CA (US); Haitao Guo, Sunnyvale, CA (US)

(73) Assignees: AAT Bioquest Inc., Sunnyvale, CA (US); Becton, Dickinson and Company, Franklin Lakes, NJ (US)

( * ) Notice: Subject to any disclaimer, the term of this patent is extended or adjusted under 35 U.S.C. 154(b) by 197 days.

(21) Appl. No.: 13/181,107

(22) Filed: Jul. 12, 2011

(65) Prior Publication Data

US 2012/0183954 A1 Jul. 19, 2012

Related U.S. Application Data

(60) Provisional application No. 61/399,995, filed on Jul. 21, 2010.

(51) Int. Cl.
*A61K 51/00* (2006.01)
*A61M 36/14* (2006.01)

(52) U.S. Cl.
USPC ............ 424/1.11; 435/6.1; 435/7.1; 435/7.5; 435/7.8; 530/321; 530/391.3; 530/330; 530/394; 530/402; 536/112; 536/22.1; 534/15; 540/492

(58) Field of Classification Search
None
See application file for complete search history.

(56) References Cited

U.S. PATENT DOCUMENTS

| | | | |
|---|---|---|---|
| 6,403,807 B1 * | 6/2002 | Singh et al. | 548/455 |
| 7,465,810 B2 | 12/2008 | Diwu et al. | |
| 2003/0170575 A1 | 9/2003 | Furuuchi | |
| 2004/0028611 A1 * | 2/2004 | Frangioni | 424/9.6 |
| 2006/0121503 A1 * | 6/2006 | Diwu et al. | 435/6 |
| 2007/0098638 A1 * | 5/2007 | Achilefu et al. | 424/9.6 |
| 2008/0177086 A1 * | 7/2008 | Frank et al. | 548/525 |
| 2009/0163446 A1 | 6/2009 | Hanson et al. | |

FOREIGN PATENT DOCUMENTS

| | | |
|---|---|---|
| WO | WO 9746099 A1 * | 12/1997 |
| WO | 0102374 A1 | 1/2001 |
| WO | 2004024734 A1 | 3/2004 |
| WO | 2005003086 A2 | 1/2005 |
| WO | 2007038659 A1 | 4/2007 |
| WO | WO 2007038659 A1 * | 4/2007 |

OTHER PUBLICATIONS

Broekema et al. J. Med. Chem. 2005, 48, 6442-6453.*

Bruyneel et al., "Laccase-Mediated Synthesis of Novel Substituted Phenoxazine Chromophores Featuring Tuneable Water Solubility", Chemistry—A European Journal, vol. 15. No. 33, Aug. 17, 2009, pp. 8283-8295, XP55019117.

Bruyneel et al, "Live-Cell Imaging with Water-Soluble Aminophenoxazinone Dyes Synthesised through Laccase Biocatalysis", Chembiochem, vol. 11, No. 10, Jun. 8, 2010, pp. 1451-1457, XP55019116.

Bugaut et al., "Exploring the Differential Recognition of DNA G-Quadruplex Targets by Small Molecules Using Dynamic Combinatorial Chemistry", Angewandte Chemie International Edition, vol. 47, No. 14, Mar. 25, 2008, pp. 2677-2680, XP55019112.

Bugaut et al., "Exploring the Differential Recognition of DNA G-quadruplex Targets by Small Molecules using Dynamic Combinatorial Chemistry", Angewandte Chemie Supporting Information, VCH, DE, Jan. 1, 2008. pp. 1-18, XP007920242.

Burgett et al., "A Concise and Flexible Total Synthesis of (-)-Diazonamide A", Angewandte Chemie International Edition, vol. 42, No. 40, Oct. 20, 2003, pp. 4961-4966, XP55001112.

E.J. Cross, "The Identification of Sulphonic Acid Reduction Products of Azo Dyes II-Sulphonic Acids of 1-Amino-2-naphthol", Journal of the Society of Dyers and Colourists, vol. 78, No. 6, Jan. 1, 1962, pp. 280-285, XP55019111.

Endoh N. et al., "Useful synthesis of the longer array oxazole rings for telomestatin", Heterocycles, Elsevier Science Publishers B.V. Amsterdam, NL, vol. 60, No. 7, Jun. 9, 2003, pp. 1567-1572, XP001538348.

International Search Report for application No. PCT/US2011/044776 dated Mar. 2, 2012.

Jared F. Mike et al, "An Efficient Synthesis of 2,6-Disubstituted Benzobisoxazoles: New Building Blocks for Organic Semiconductors", Organic Letters, vol. 10, No. 21, Nov. 6, 2008, pp. 4915-4918, XP55019109.

Muzik F, "Aromatische Diazo- and Azoverbindungen XL. Schliessung des Oxazinringes bei Amino-peri-benzaminonaphtholsulfonsauren. Uber die Darstellung einiger Peri-naphthoxazin-derivate", Collection of Czechoslovak Chemical Communications, Institute of Organic Chemistry & Biochemistry, Prague; CZ, vol. 25. Jan. 1 ,1960, pp. 2831-2840, XP009156491.

Truong Son et al., "Study of the reactions of dyes of the alizarin green series with U022+ ions in the presence of cetyltrimethylammonium cation", Collection of Czechoslovak Chemical Communications.

(Continued)

*Primary Examiner* — Michael G Hartley
*Assistant Examiner* — Sean R Donohue
(74) *Attorney, Agent, or Firm* — Bozicevic, Field & Francis LLP; Bret E. Field; Glenn J. Foulds

(57) ABSTRACT

Chemically reactive dyes that are intramolecularly crosslinked with a water-soluble bridge, their bioconjugates and their uses are described. Reactive fluorescent dyes that have a water-soluble bridge are superior to those of conjugates of spectrally non-crosslinked dyes or the dyes that are crosslinked with a hydrophobic bridge. The invention includes reactive fluorescent dyes, their biological conjugates and uses.

4 Claims, 10 Drawing Sheets

(56) References Cited

OTHER PUBLICATIONS

Institute of Organic Chemistry & Biochemistry, Prague; CZ, vol. 44, No. 11, Jan. 1, 1979, pp. 3264-3274, XP009156492.

Partial International Search Report, PCT/US2011/044776, dated Dec. 29, 2011.

* cited by examiner

LUMINESCENT DYES WITH A WATER-SOLUBLE INTRAMOLECULAR BRIDGE AND THEIR BIOLOGICAL CONJUGATES

BACKGROUND OF THE INVENTION

1. Field of the Invention

The invention relates to luminescent dyes, including reactive dyes and dye conjugates; and their biological uses.

2. Description of Related Art

Luminescent probes are valuable reagents for the analysis and separation of molecules and cells and for the detection and quantification of other materials. A very small number of luminescent molecules can be detected under optimal circumstances. Some specific examples of the application of fluorescent probes are (1) identification and separation of subpopulations of cells in a mixture of cells by the techniques of fluorescence flow cytometry, fluorescence-activated cell sorting and fluorescence microscopy; (2) determination of the concentration of a substance that binds to a second species (e.g., antigen-antibody reactions) in the technique of fluorescence immunoassay; (3) localization of substances in gels and other insoluble supports by the techniques of fluorescence staining. These techniques are described by Herzenberg, et al., "CELLULAR IMMUNOLOGY" 3rd ed., Chapter 22; Blackwell Scientific Publications (1978); and by Goldman, "FLUORESCENCE ANTIBODY METHODS", Academic Press, New York, (1968); and by Taylor, et al., APPLICATIONS OF FLUORESCENCE IN THE BIOMEDICAL SCIENCES, Alan Liss Inc., (1986), and Shapiro, PRACTICAL FLOW CYTOMETRY, 4th ed., Wiley-Liss (2003), all of which are incorporated herein by reference.

When employing luminescent dyes for the above purposes, there are many constraints on the choice of the fluorescent dye. One constraint is the absorption and emission characteristics of the fluorescent dye, since many ligands, receptors, and materials in the sample under test, e.g. blood, urine, cerebrospinal fluid, will fluoresce and interfere with an accurate determination of the fluorescence of the fluorescent label. This phenomenon is called autofluorescence or background fluorescence. Another consideration is the ability to conjugate the fluorescent dye to ligands and receptors and other biological and non-biological materials and the effect of such conjugation on the fluorescent dye. In many situations, conjugation to another molecule may result in a substantial change in the fluorescent characteristics of the fluorescent dye and, in some cases, substantially destroy or reduce the quantum efficiency of the fluorescent dye. It is also possible that conjugation with the fluorescent dye will inactivate the function of the molecule that is labeled. A third consideration is the quantum efficiency of the luminescent dyes which should be high for sensitive detection. A fourth consideration is the light absorbing capability, or extinction coefficient, of the luminescent dyes, which should also be as large as possible. Also of concern is whether the fluorescent molecules will interact with each other when in close proximity, resulting in self-quenching. An additional concern is whether there is non-specific binding of the luminescent dyes to other compounds or container walls, either by themselves or in conjunction with the compound to which the fluorescent dye is conjugated.

The applicability and value of the methods indicated above are closely tied to the availability of suitable fluorescent compounds. In particular, there is a need for fluorescent substances that emit in the longer wavelength region (yellow to near infrared), since excitation of these chromophores produces less autofluorescence and also multiple chromophores fluorescing at different wavelengths can be analyzed simultaneously if the full visible and near infrared regions of the spectrum can be utilized. Fluorescein, a widely used fluorescent compound, is a useful emitter in the green region although in certain immunoassays and cell analysis systems background autofluorescence generated by excitation at fluorescein absorption wavelengths limits the detection sensitivity. However, the conventional red fluorescent label rhodamine has proved to be less effective than fluorescein.

Phycobiliproteins have made an important contribution because of their high extinction coefficient and high quantum yield. These chromophore-containing proteins can be covalently linked to many proteins and are used in fluorescence antibody assays in microscopy and flow cytometry. The phycobiliproteins have the disadvantages that (1) the protein labeling procedure is relatively complex; (2) the protein labeling efficiency is not usually high (typically an average of 0.5 phycobiliprotein molecules per protein); (3) the phycobiliproteins are natural products and their preparation and purification are complex; (4) the phycobiliproteins are expensive; (5) there are at present no phycobiliproteins available as labeling reagents that fluoresce further to the red region of the spectrum than allophycocyanine, which fluoresces maximally at 680 nm; (6) the phycobiliproteins are large proteins with molecular weights ranging from 33,000 to 240,000 and are larger than many materials that are desirable to label, such as metabolites, drugs, hormones, derivatized nucleotides, and many proteins including antibodies. The latter disadvantage is of particular importance because antibodies, avidin, DNA-hybridization probes, hormones, and small molecules labeled with the large phycobiliproteins may not be able to bind to their targets because of steric limitations imposed by the size of the conjugated complex.

Other techniques involving histology, cytology, immunoassays would also enjoy substantial benefits from the use of a fluorescent dye with a high quantum efficiency, absorption and emission characteristics at longer wavelengths, having simple means for conjugation and being substantially free of nonspecific interference.

Fluorescent compounds are covalently or noncovalently attached to other materials to impart color and fluorescence. Brightly luminescent dyes permit detection or location of the attached materials with great sensitivity. Certain carbocyanine dyes have demonstrated utility as labeling reagents for a variety of biological applications, e.g. U.S. Pat. No. 4,981,977 to Southwick, et al. (1991); U.S. Pat. No. 5,268,486 to Waggoner, et al. (1993); U.S. Pat. No. 5,569,587 to Waggoner (1996); U.S. Pat. No. 5,569,766 to Waggoner, et al. (1996); U.S. Pat. No. 5,486,616 to Waggoner, et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung, et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000). Nevertheless, many carbocyanine dyes are known to share certain disadvantages, e.g. severe quenching of the fluorescence of carbocyanine dyes in biopolymer conjugates, e.g. quenching of Cy5 and Cy7 dye variants on conjugates, as discussed by Gruber, et al., BIOCONJUGATE CHEM., 11, 696 (2000). In addition, certain desired sulfoalkyl derivatives of the reactive carbocyanine dyes are difficult to prepare, as indicated for Cy3 and Cy5 variants by Waggoner and colleagues in BIOCONJUGATE CHEM., 4, 105, 109 (1993).

Cyanine dyes also have a very strong tendency to self-aggregate (i.e. stack), which can significantly reduce the fluorescence quantum yields, as described in the extensive review by Mishra, et al., CHEM. REV., 100, 1973 (2000).

Another problem with the existing carbocyanine labeling dyes is the free rotation/vibration of two indolium (or benzothiazolium, or benzoimidazolium) heads around the middle conjugated double bonds that significantly reduce their fluorescence intensities. This phenomenon is called 'loose belt effect' that is described in "MODERN MOLECULAR PHOTOCHEMISTRY", Chapters 5 and 6, University Science Books, Sausalito, Calif., authored by Nicholas J. Turro (1991).

This so-called 'loose belt effect' can be eliminated by the crosslinking of the two heads. 1,1'-crosslinking of cyanines is disclosed by R. Singh, et al. WO 01/02374 (2001), which is supposed to eliminate the 'loose belt effect' described above. However, Diwu et al., U.S. Pat. No. 7,465,810, observed that the 1,1'-crosslinking actually caused the decreased fluorescence quantum yield of dye-protein conjugates compared to that of non-crosslinked carbocycanine-protein conjugates at the similar ratios of dye/protein. This unfavorable fluorescence decrease might be caused by the inappropriate stereochemistry of 1,1'-crosslinking or by the increased hydrophobicity, which results from the addition of the highly hydrophobic bridge.

Diwu et al., U.S. Pat. No. 7,465,810, observed that the fluorescence properties of cyanine labeling dyes were improved by the intramolecularly crosslinking of the two indoline moieties between the 1-position and 3'-position. The 1,3'-crosslinked carbocyanines are superior to those of conjugates of spectrally similar 1,1'-crosslinked or non-crosslinked dyes. This improvement with 1,3'-cros slinked cyanine might result from the favorable configuration. However, the hydrophobic bridge significantly increases the dye hydrophobicity. Compared to the non-crosslinked carbocyanine dyes the conjugation of either 1,3'-crosslinked or 1,1'-crosslinked carbocyanines to proteins and other biological molecules often caused the precipitation of the labeling target molecules due to the significantly reduced water solubility of labeling dyes caused by the highly hydrophobic cross linker. In some cases, the cros slinking of carbocyanines by a highly hydrophobic bridge result in a complete activity loss of the target molecules to be labeled.

We discovered new water-soluble cross linkers that do not only eliminate the 'loose belt effect' to increase the fluorescence quantum yields of labeling dyes, but also increase their water solubility, thus eliminating the drawback of protein precipitation with the existing luminescent dyes that contain a hydrophobic cross linking bridge. We found that this strategy of water-soluble bridge can also be used improve the labeling and spectral properties of luminescent dyes of other types.

Xanthene dyes are another class of fluorescent probes that are predominantly used for labeling proteins and other biological molecules, e.g., U.S. Pat. No. 7,704,284 to Eliu, et al. (2010); U.S. Pat. No. 7,491,830 to Lam, et al. (2009); U.S. Pat. No. 7,344,701 to Reddington, et al. (2008); U.S. Pat. No. 6,229,055 to Klaubert, et al. (2001); U.S. Pat. No. 6,130,101 to Mao et al. (2000). We discovered that the 'loose belt effect' of xanthene dyes can be eliminated by the crosslinking of the two substitute heads with the new water-soluble cross linkers while their water solubilities are also significantly increased. The same principle can also be used to simultaneously increase the fluorescence quantum yields and water solubility of oxazole dye-protein conjugates and luminescent metal complex-protein conjugates.

Using a FSC versus SSC dot plot the lymphocytes are gated and the median fluorescence is measured.

SUMMARY OF THE INVENTION AND DESCRIPTION OF PREFERRED EMBODIMENTS

Figure 1:
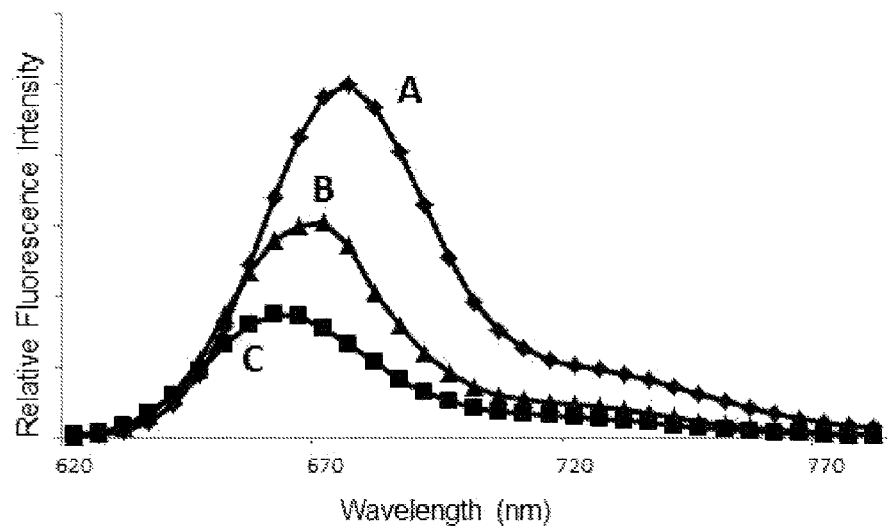
FIG. 1. Comparison of fluorescence quantum yields of dye-goat anti-rabbit IgG (GAR) conjugates that are respectively prepared from Cyanines 133, 134 and 135 (Cy5 NHS ester) and characterized as described in Examples 56. Their PBS solutions are adjusted to have the same absorption of OD=0.05 at 600 nm. The PBS solutions are excited at 600 nm, and the emissions are scanned from 620 to 800 nm. The protein conjugate prepared from Compound 134 (Curve A, dye/protein=4.8) is much brighter than the conjugates prepared from either Compound 133 (Curve B, dye/protein=4.6) or 135 (Curve C, dye/protein=4.5). Compound 133 causes protein to precipitate when the ratio of dye/protein is larger than 10 while the dye-protein conjugate of Compound 134 is still water soluble when the ratio of dye/protein is larger than 10.
Figure 2:
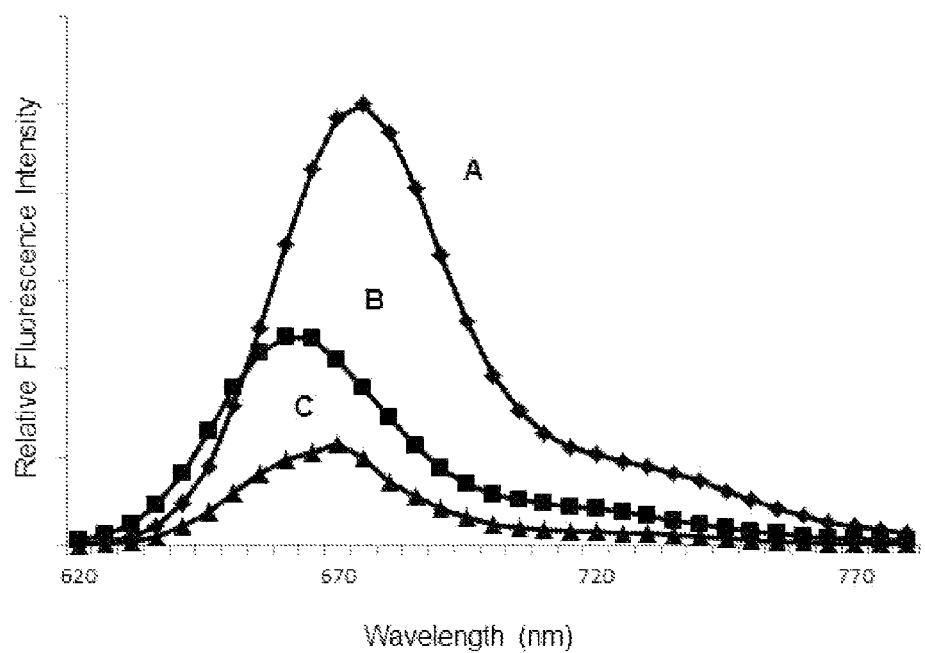
FIG. 2. Comparison of fluorescence quantum yields of dye-goat anti-rabbit IgG (GAR) conjugates that are respectively prepared from Cyanines 39, 136 and 137 (Cy5 Bis-NHS ester) and characterized as described in Examples 56. Their PBS solutions are adjusted to have the same absorption of OD=0.05 at 600 nm. The PBS solutions are excited at 600 nm, and the emissions are scanned from 620 to 800 nm. The protein conjugate prepared from Compound 39 (Curve A, dye/protein=5.1) is much brighter than the conjugates prepared from either Compound 136 (Curve C, dye/protein=5.0) or 137 (Curve B, dye/protein=5.3). Compound 136 causes protein to precipitate when the ratio of dye/protein is larger than 8 while the dye-protein conjugate of Compound 39 is still water soluble when the ratio of dye/protein is larger than 8.
Figure 3:
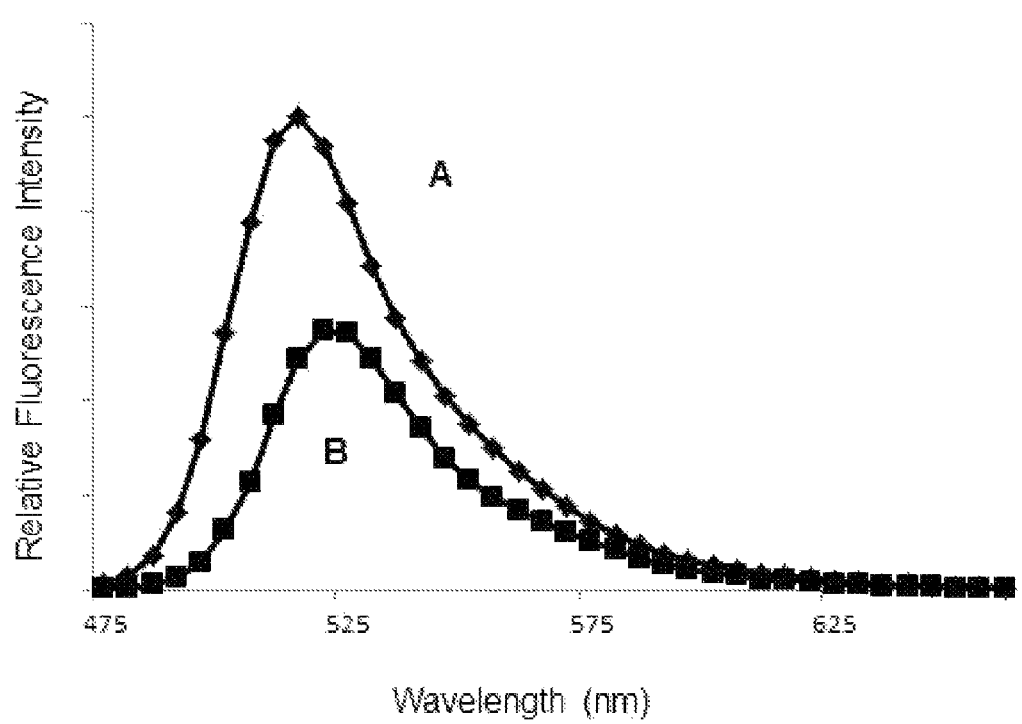
FIG. 3. Comparison of fluorescence quantum yields of dye-goat anti-rabbit IgG (GAR) conjugates that are respectively prepared from Rhodamine 43 and 132 and characterized as described in Examples 56. Their PBS solutions are adjusted to have the same absorption of OD=0.1 at 450 nm. The PBS solutions are excited at 460 nm, and the emissions are scanned from 470 to 650 nm. The protein conjugate prepared from Compound 43 (Curve A, dye/protein=4.5) is much brighter than the conjugate prepared from Compound 132 (Curve B, dye/protein=4.7). Compound 132 causes protein to precipitate when the ratio of dye/protein is larger than 12 while the dye-protein conjugate of Compound 43 is still water soluble when the ratio of dye/protein is larger than 12.

We discovered that a new class of water-soluble cross linking bridge unexpectedly mitigates problems discussed in the background section and results in dye-polymer conjugates that are substantially more luminescent on proteins, nucleic acids and other biopolymers, than conjugates labeled with structurally similar non-crosslinked dyes or the dyes that are cross linked with a hydrophobic bridge (see FIGS. 1, 2 and 3). The enhanced luminescence intensity and retained binding affinity of dye-biomolecule conjugates of the invention results in greater assay sensitivity.

Furthermore, the dyes of the invention typically exhibit absorbance maxima between about 400 nm and 1000 nm, so these dyes can be selected to match the principal emission lines of the violet laser (405 nm), Argon laser (488 nm), mercury arc lamp (546 nm), frequency-doubled Nd-Yag laser (532 nm), Kr-ion laser (568 nm and 647 nm), He—Ne laser (543 nm, 594 nm, and 633 nm) or long-wavelength laser diodes (especially 635 nm and longer). Some dyes of the invention exhibit very long wavelength excitation (at least 640 nm, but some greater than about 730 nm) and emission bands (at least 665 nm, and some greater than about 750 nm), so they are particularly useful for samples that are transparent to infrared wavelengths.

The present invention comprises reactive luminescent dyes that are cross linked with a water soluble bridge (WSB) and their conjugates. The dyes and dye conjugates are used to locate or detect the interaction or presence of analytes or ligands in a sample. Kits incorporating such dyes or dye conjugates facilitate their use in such methods.

In another aspect, the present invention provides dye-conjugates that comprise one or more of the luminescent dyes of the invention that are cross linked with a water soluble bridge (WSB) conjugated to a substrate. In preferred embodiments, the dye-conjugates are used as fluorescent detection reagents to detect, identify, locate, or quantitate analytes in a sample.

In a preferred embodiment of the invention, the dye-conjugate substrate is a biopolymer, and the biopolymer is conjugated to a one or more of the of the luminescent dyes of the invention that are cross linked with a water soluble bridge (WSB) to obtain a fluorescent biopolymer. The fluorescent biopolymer dye-conjugates of the invention have utility as, or as part of, detection reagents, including analyte-specific detection reagents. Useful biopolymers include, for example, amino acid polymers, nucleic acid polymers, polysaccharides, carbohydrates, and lipids. In a preferred embodiment, the biopolymer component of the dye-biopolymer conjugate is an amino acid polymer, as broadly defined herein. In a preferred embodiment, the biopolymer is a monoclonal antibody.

In another aspect, the present invention provides kits containing the reactive dyes or dye-conjugates of the present invention. Kits of the present invention can contain additional components useful for carrying out the intended application, such as other reagents or buffers.

The dyes of the invention typically have Formula 1:

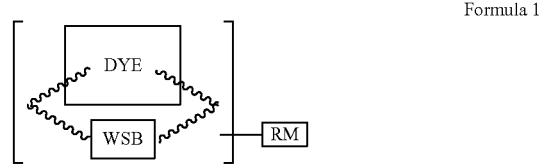

Formula 1 wherein DYE represents a luminescent dye; RM is a chemically reactive moiety described below; WSB is a water-soluble bridge that is used to cross link either two bulky substitutes of the same ring of a luminescent dye or two different rings of a luminescent dye.

The dyes of the invention comprise a luminescent dye that contains: 1) an RM group; and 2) a water-soluble and non-conjugated bridge that intramolecularly crosslinks either two bulky substitutes of the same ring of a luminescent dye or two different rings of a luminescent dye. In one embodiment of the invention, the first or second ring system is substituted by a side chain that contains an RM group. In another embodiment, WSB contains an RM group.

In one aspect of the invention, the luminescent dyes of the invention are sulfonated one or more times. In addition, the dyes of the invention are substituted by one or more chemically reactive moieties (RM) or conjugated substances as described below. In a preferred embodiment, the dye of the invention is substituted by only one RM.

Preferred WSB incorporates at least a negatively charged group (e.g., carboxy, sulfonate, phosphate and phosphonate) to increase water solubility. By "sulfonate" is meant sulfonic acid, or salts of sulfonic acid (sulfonate). Similarly, by "carboxy" is meant carboxylic acid or salts of carboxylic acid. "Phosphate", as used herein, is an ester of phosphoric acid, and includes salts of phosphate. "Phosphonate", as used herein, means phosphonic acid and includes salts of phosphonate. In addition, "sulfonate" and "phosphonate" are interchangeable with "sulfonyl" and "phosphonyl" respectively. As used herein, unless otherwise specified, the alkyl portions of substituents such as alkyl, alkoxy, arylalkyl, alylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfonate, amino, or hydroxy.

Another preferred WSB is a peptide that contains at least two water soluble moieties derived from sulfoalkyl, sulfoaryl, sulfoheteroaryl, phosphonylalkyl, phosphonylaryl or phosphonylheteroaryl group. Another preferred WSB contains an thiophene moiety. Another preferred WSB contains an RM.

Preferred DYE is a fluorescein, a rhodamine, an oxazine, a cyanine, an oxazole, a bodipy, a phthalocyanine, a thiophene, a ruthernium complex or a lanthanide complex.

Another preferred embodiment is a compound of Formula 2

Formula 2

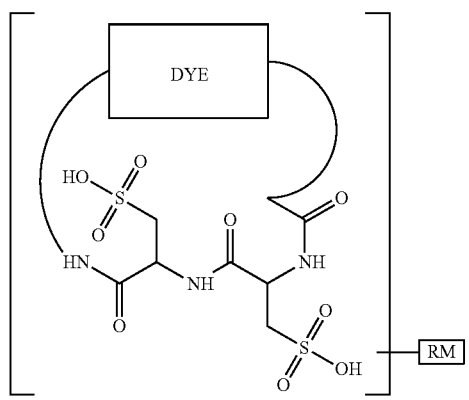

wherein DYE represents a luminescent dye. RM is a chemically reactive moiety described below.

Another preferred embodiment is a compound of Formula 3

Formula 3

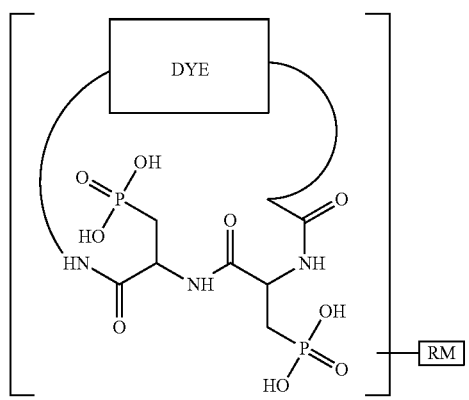

wherein DYE represents a luminescent dye. RM is a chemically reactive moiety described below.

Another preferred embodiment is a compound of Formula 4

Formula 4

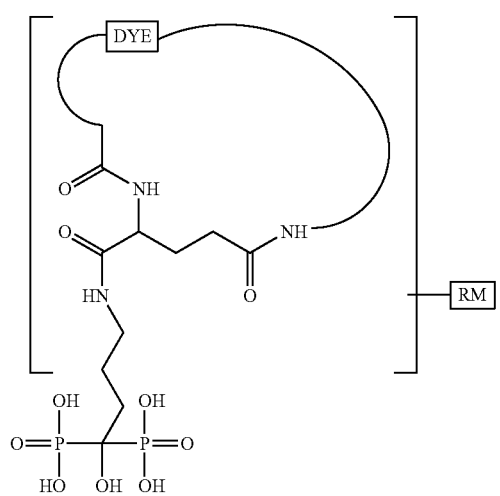

wherein DYE represents a luminescent dye. RM is a chemically reactive moiety described below.

Another preferred embodiment is a compound of Formula 5

Formula 5

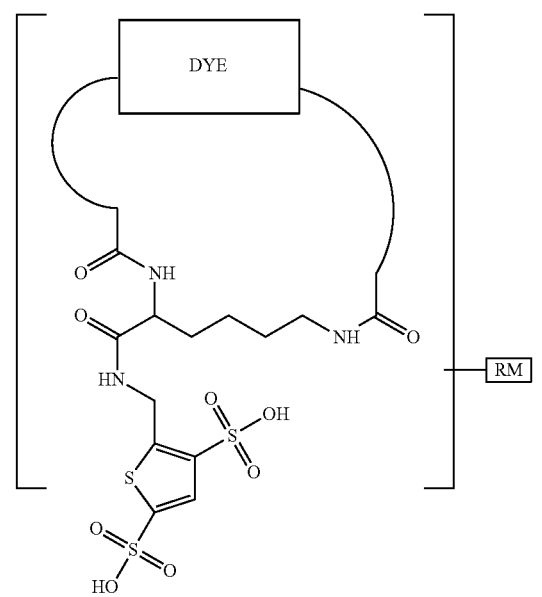

wherein DYE represents a luminescent dye. RM is a chemically reactive moiety described below.

Another preferred embodiment is a compound of Formula 6

Formula 6

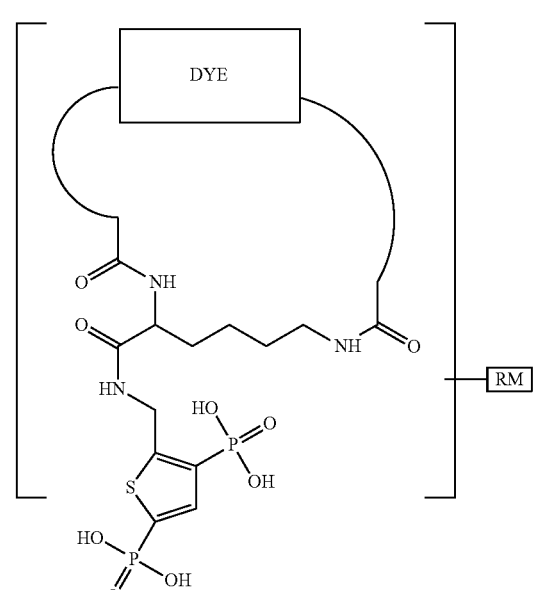

wherein DYE represents a luminescent dye. RM is a chemically reactive moiety described below.

Another preferred embodiment is a compound of Formula 7

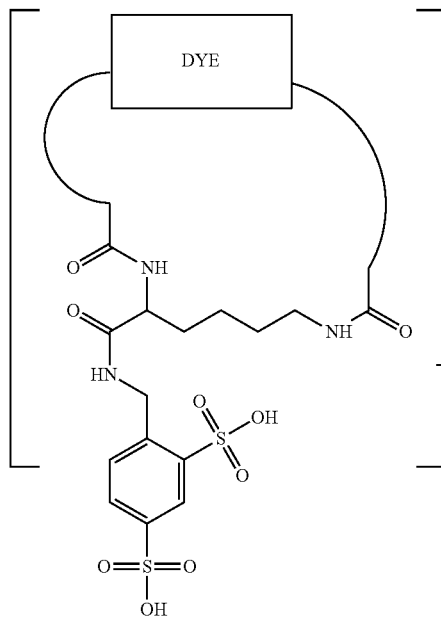

Formula 7 wherein DYE represents a luminescent dye. RM is a chemically reactive moiety described below.

Another preferred embodiment is a compound of Formula 8

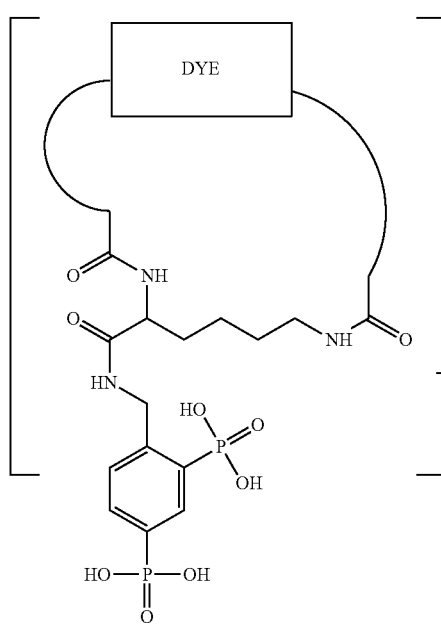

Formula 8 wherein DYE represents a luminescent dye. RM is a chemically reactive moiety described below.

Another preferred embodiment is a compound of Formula 9:

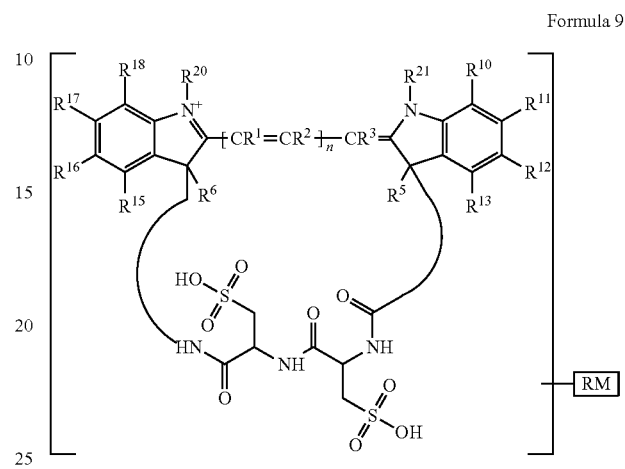

Formula 9 wherein $R^1$ to $R^3$ are independently a hydrogen, a halogen, an alkyl having 1-20 carbons, an aryl, a heteroaryl or an RM; $R^5$ and $R^6$ are independently an alkyl having 1-20 carbons, an aryl, a heteroaryl or an RM; $R^{10}$ to $R^{19}$ are independently a hydrogen, an alkyl having 1-20 carbons, an alkoxy having 1-20 carbons, a trifluoromethyl, a halogen, a methylthio, a sulfonyl, a boronyl, a phosphonyl, a cyano, a carbonyl, a hydroxy, an amino, a thiol, an aryl, a heteroaryl or an RM; $R^{20}$ and $R^{21}$ are independently an alkyl, an arylalkyl, an alkoxyalkyl, a polyethyleneglycol or an RM; One or more of $R^{10}$ and $R^{21}$, $R^{10}$ and $R^{11}$, $R^{11}$ and $R^{12}$, $R^{12}$ and $R^{13}$, $R^5$ and $R^{13}$, $R^6$ and $R^{15}$, $R^{15}$ and $R^{16}$, $R^{16}$ and $R^{17}$, $R^{17}$ and $R^{18}$, or $R^{18}$ and $R^{20}$ are optionally taken in combination to form a cycloalkyl, a hetero ring, an aryl or a heteroaryl ring; RM is a chemically reactive moiety described below; n is 0 to 3.

The length of the conjugated polymethine bridge between the two ring systems greatly affects the dye's absorption and emission properties. Each of $R^1$, $R^2$, $R^3$, when present, is independently a hydrogen, a fluoro, a chloro, an alkyl having 1-6 carbons, an alkoxy having 1-6 carbons, an aryl, an aryloxy, a N-heteroaromatic moiety, or an iminium ion. Alternatively, two substituents $R_1/R_2$, $R_2/R_3$, when taken in combination, form a 4-, 5-, or 6-membered saturated or unsaturated hydrocarbon ring that is unsubstituted or is optionally substituted one or more times by a saturated or unsaturated alkyl having 1-6 carbons, a halogen, or a carbonyl oxygen. Typically, each of $R_1$, $R_2$ and $R_3$, when present, is a hydrogen. Where one of $R_1$, $R_2$ and $R_3$ is a nonhydrogen, it is typically the substituent on the center carbon of bridged and conjugated double bonds. Similarly, where bridged and conjugated double bonds incorporate a 4-, 5-, or 6-membered ring, it typically occurs at the center of the conjugated bridge moiety.

Another preferred embodiment is a compound of Formula 10:

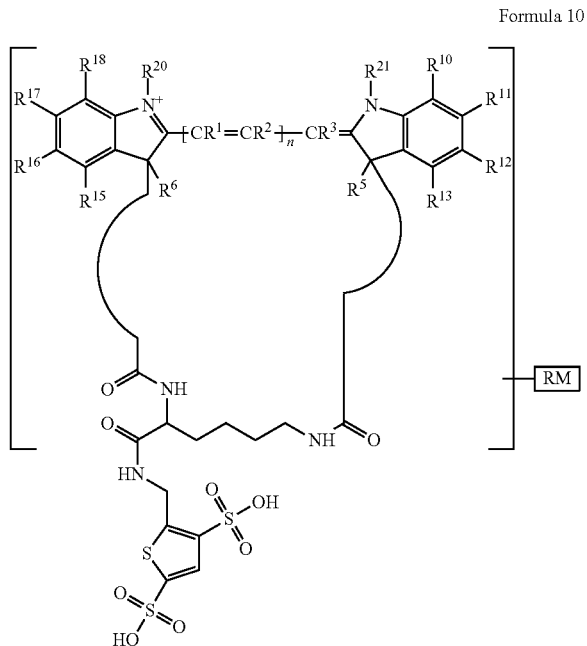

Formula 10 wherein $R^1$ to $R^3$ are independently a hydrogen, a halogen, an alkyl having 1-20 carbons, an aryl, a heteroaryl or an RM; $R^5$ and $R^6$ are independently an alkyl having 1-20 carbons, an aryl, a heteroaryl or an RM; $R^{10}$ to $R^{19}$ are independently a hydrogen, an alkyl having 1-20 carbons, an alkoxy having 1-20 carbons, a trifluoromethyl, a halogen, a methylthio, a sulfonyl, a boronyl, a phosphonyl, a cyano, a carbonyl, a hydroxy, an amino, a thiol, an aryl, a heteroaryl or an RM; $R^{20}$ and $R^{21}$ are independently an alkyl, an arylalkyl, an alkoxyalkyl, a polyethyleneglycol or an RM; One or more of $R^{10}$ and $R^{21}$, $R^{10}$ and $R^{11}$, $R^{11}$ and $R^{12}$, $R^{12}$ and $R^{13}$, $R^5$ and $R^{13}$, $R^6$ and $R^{15}$, $R^{15}$ and $R^{16}$, $R^{16}$ and $R^{17}$, $R^{17}$ and $R^{18}$, or $R^{18}$ and $R^{20}$ are optionally taken in combination to form a cycloalkyl, a hetero ring, an aryl or a heteroaryl ring; RM is a chemically reactive moiety described below; n is 0 to 3.

Another preferred embodiment is a compound of Formula 11:

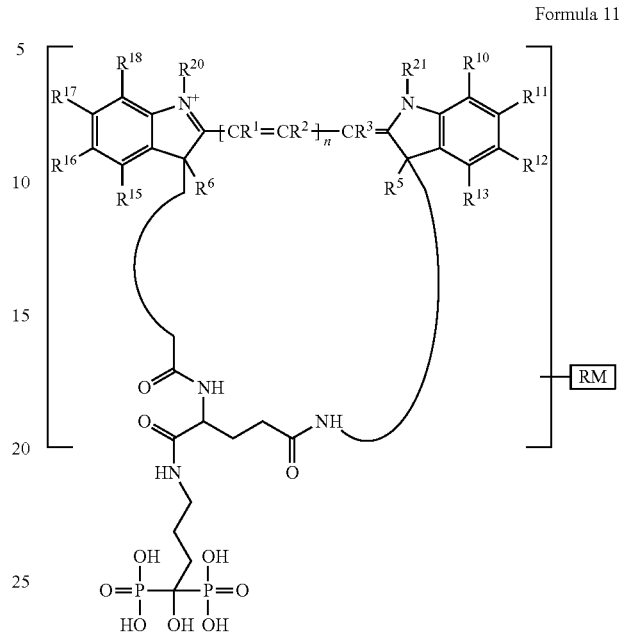

Formula 11 wherein $R^1$ to $R^3$ are independently a hydrogen, a halogen, an alkyl having 1-20 carbons, an aryl, a heteroaryl or an RM; $R^5$ and $R^6$ are independently an alkyl having 1-20 carbons, an aryl, a heteroaryl or an RM; $R^{10}$ to $R^{19}$ are independently a hydrogen, an alkyl having 1-20 carbons, an alkoxy having 1-20 carbons, a trifluoromethyl, a halogen, a methylthio, a sulfonyl, a boronyl, a phosphonyl, a cyano, a carbonyl, a hydroxy, an amino, a thiol, an aryl, a heteroaryl or an RM; $R^{20}$ and $R^{21}$ are independently an alkyl, an arylalkyl, an alkoxyalkyl, a polyethyleneglycol or an RM; One or more of $R^{10}$ and $R^{21}$, $R^{10}$ and $R^{11}$, $R^{11}$ and $R^{12}$, $R^{12}$ and $R^{13}$, $R^5$ and $R^{13}$, $R^6$ and $R^{15}$, $R^{15}$ and $R^{16}$, $R^{16}$ and $R^{17}$, $R^{17}$ and $R^{18}$, or $R^{18}$ and $R^{20}$ are optionally taken in combination to form a cycloalkyl, a hetero ring, an aryl or a heteroaryl ring; RM is a chemically reactive moiety described below; n is 0 to 3.

Another preferred embodiment is a compound of Formula 12:

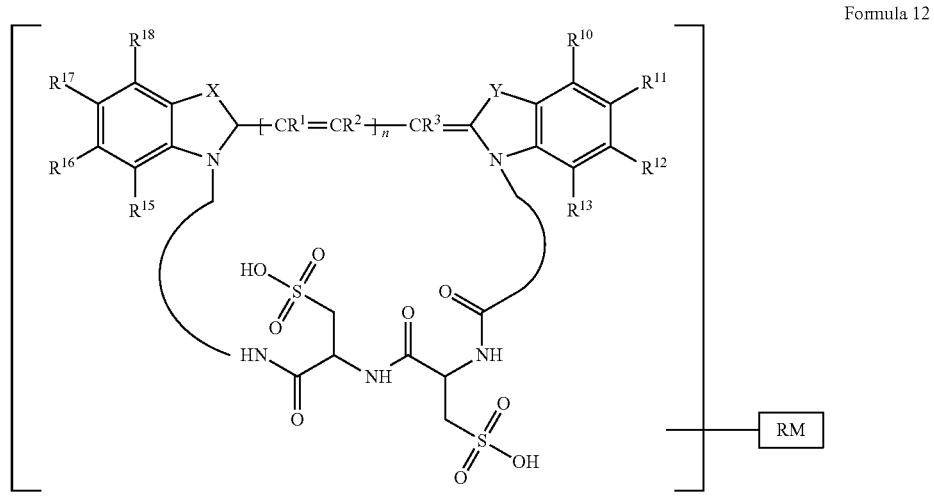

Formula 12 wherein X and Y are independently O, S, Se or $CR^{20}R^{21}$; $R_1$ to $R^3$ are independently a hydrogen, a halogen, an alkyl having 1-20 carbons, an aryl, a heteroaryl or an RM; $R^5$ and $R^6$ are independently an alkyl having 1-20 carbons, an aryl, a heteroaryl or an RM; $R^{10}$ to $R^{19}$ are independently a hydrogen, an alkyl having 1-20 carbons, an alkoxy having 1-20 carbons, a trifluoromethyl, a halogen, a methylthio, a sulfonyl, a boronyl, a phosphonyl, a cyano, a carbonyl, a hydroxy, an amino, a thiol, an aryl, a heteroaryl or an RM; $R^{20}$ and $R^{21}$ are independently an alkyl, an arylalkyl, an alkoxyalkyl, a polyethyleneglycol or an RM; One or more of $R^{10}$ and $R^{20}$, $R^{10}$ and $R^{21}$, $R^{10}$ and $R^{11}$, $R^{11}$ and $R^{12}$, $R^{12}$ and $R^{13}$, $R^{15}$ and $R^{16}$, $R^{16}$ and $R^{17}$, $R^{17}$ and $R^{18}$, or $R^{18}$ and $R^{20}$, $R^{18}$ and $R^{21}$ are optionally taken in combination to form a cycloalkyl, a hetero ring, an aryl or a heteroaryl ring; RM is a chemically reactive moiety described below; n is 0 to 3.

Another preferred embodiment of the invention is a compound of Formula 13 wherein X and Y are independently O, S, Se or $CR^3OR^{31}$; n is 0 to 3; $R^1$ to $R^3$ are independently a hydrogen, a halogen, an alkyl having 1-20 carbons, an aryl, a heteroaryl or an RM; $R^8$ to $R^{27}$ are independently a hydrogen, an alkyl having 1-20 carbons, an alkoxy having 1-20 carbons, a trifluoromethyl, a halogen, a methylthio, a sulfonyl, a boronyl, a phosphonyl, a cyano, a carbonyl, a hydroxy, an amino, a thiol, an aryl, a heteroaryl or an RM; $R^{30}$ and $R^{31}$ are independently an alkyl, an arylalkyl, an alkoxyalkyl, a polyethyleneglycol or an RM; RM is a chemically reactive moiety described below.

Another preferred embodiment of the invention is a compound of Formula 14

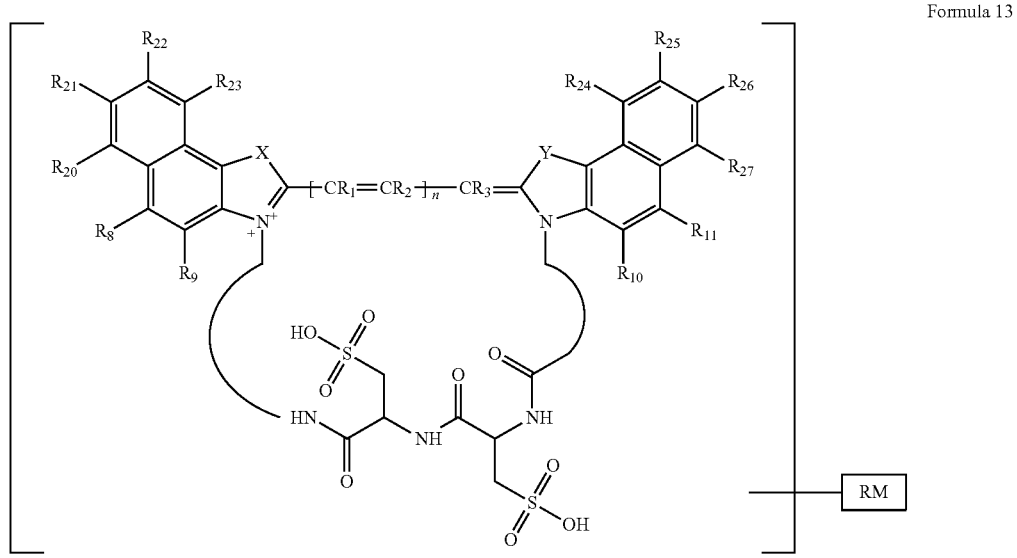

Formula 13

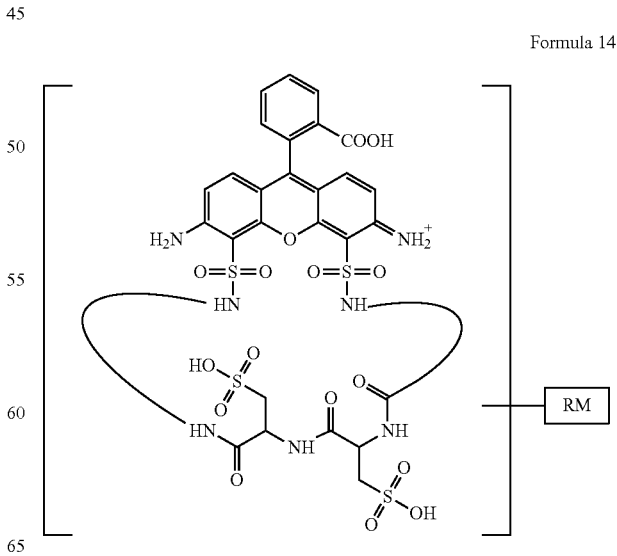

Formula 14 wherein RM is a chemically reactive moiety described below.

Another preferred embodiment of the invention is a compound of Formula 15

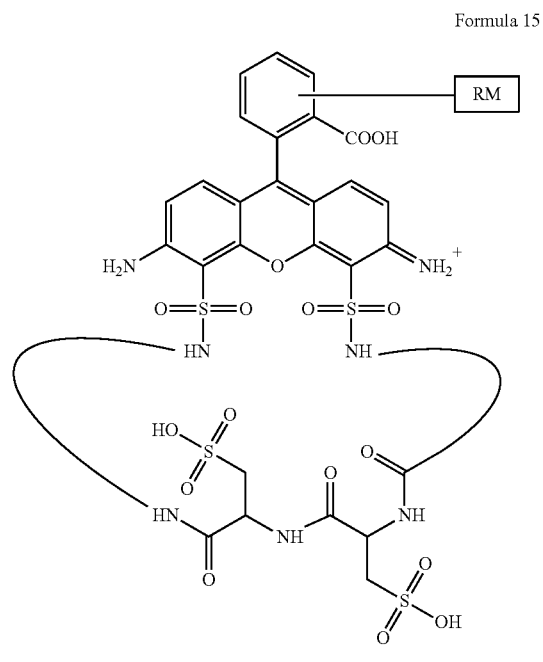

Formula 15 wherein RM is a chemically reactive moiety described below.

Another preferred embodiment of the invention is a compound of Formula 16

Formula 16

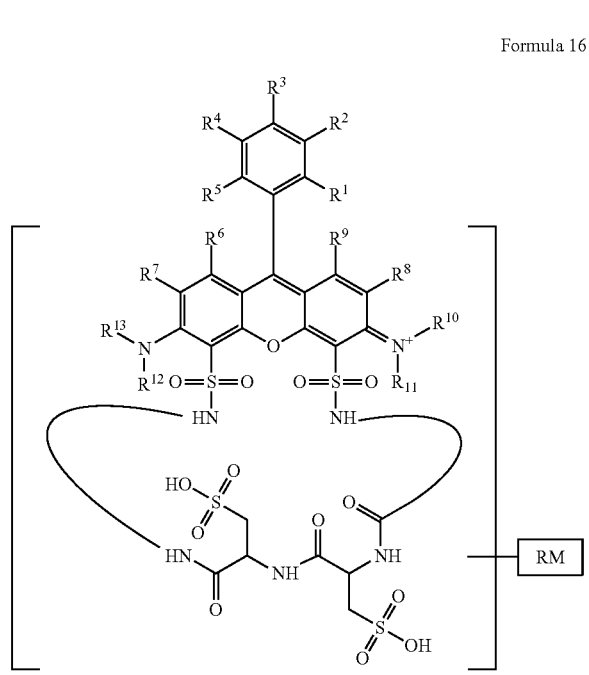

wherein $R^1$ is hydrogen, alkyl, alkoxy, carboxy or sulfo; $R^2$ to $R^9$ are independently a hydrogen, an alkyl having 1-20 carbons, an alkoxy having 1-20 carbons, a trifluoromethyl, a halogen, a methylthio, a sulfonyl, a boronyl, a phosphonyl, a cyano, a carbonyl, a hydroxy, an amino, a thiol, an aryl, a heteroaryl or an RM; $R^{10}$, $R^{11}$, $R^{12}$ and $R^{13}$ are independently an alkyl, a halogenated alkyl, an arylalkyl, an alkoxyalkyl, a polyethyleneglycol or an RM; One or more of $R^6$ and $R^7$, $R^8$ and $R^9$, $R^8$ and $R^{10}$, or $R^7$ and $R^{13}$ taken in combination form a 5- to 8-membered ring; RM is a chemically reactive moiety described below.

Another preferred embodiment of the invention is a compound of Formula 17

Formula 17

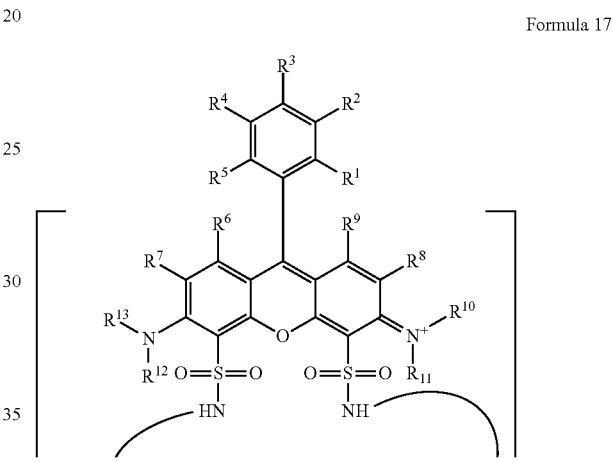

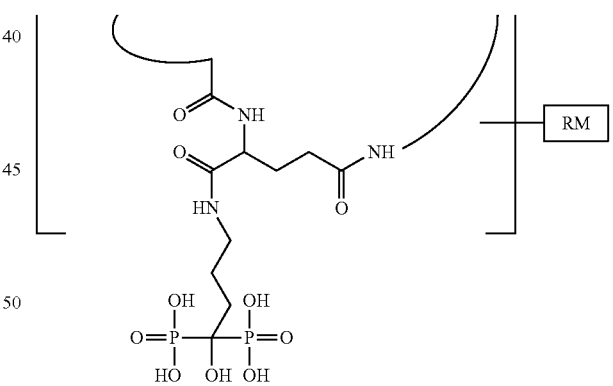

wherein $R^1$ is hydrogen, alkyl, alkoxy, carboxy or sulfo; $R^2$ to $R^9$ are independently a hydrogen, an alkyl having 1-20 carbons, an alkoxy having 1-20 carbons, a trifluoromethyl, a halogen, a methylthio, a sulfonyl, a boronyl, a phosphonyl, a cyano, a carbonyl, a hydroxy, an amino, a thiol, an aryl, a heteroaryl or an RM; $R^{10}$, $R^{11}$, $R^{12}$ and $R^{13}$ are independently an alkyl, a halogenated alkyl, an arylalkyl, an alkoxyalkyl, a polyethyleneglycol or an RM; One or more of $R^6$ and $R^7$, $R^8$ and $R^9$, $R^8$ and $R^{10}$, or $R^7$ and $R^{13}$ taken in combination form a 5- to 8-membered ring; RM is a chemically reactive moiety described below.

Another preferred embodiment of the invention is a compound of Formula 18
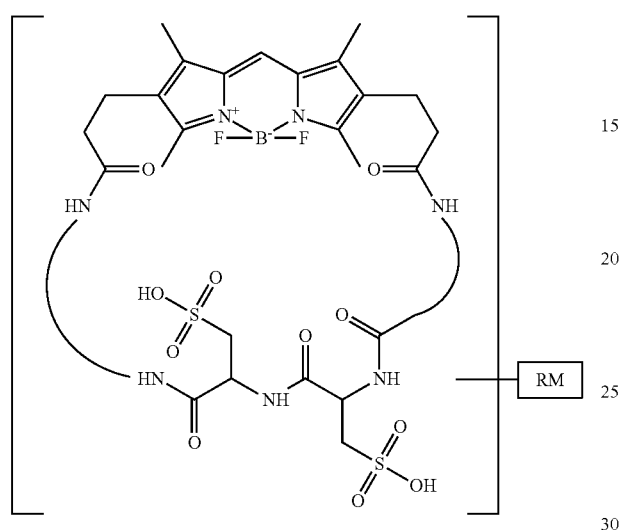
Formula 18
wherein RM is a chemically reactive moiety described below.
Another preferred embodiment of the invention is a compound of Formula 19
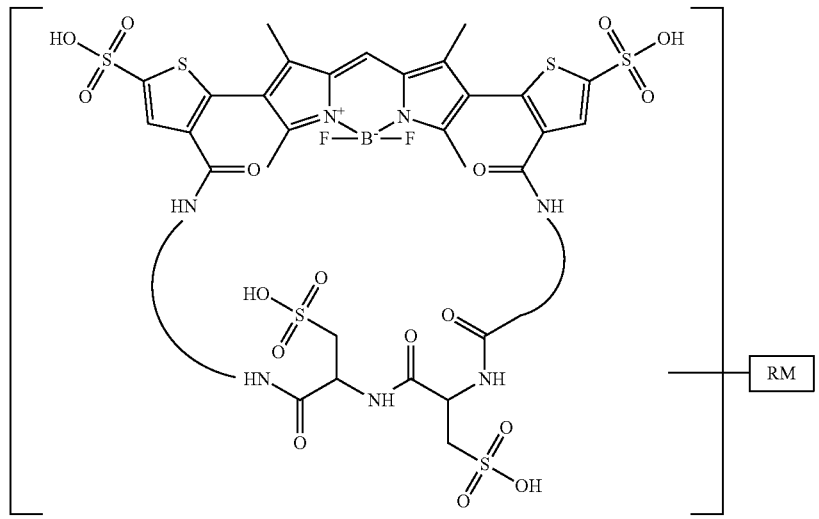
Formula 19
wherein RM is a chemically reactive moiety described below.

Another preferred embodiment of the invention is a compound of Formula 20
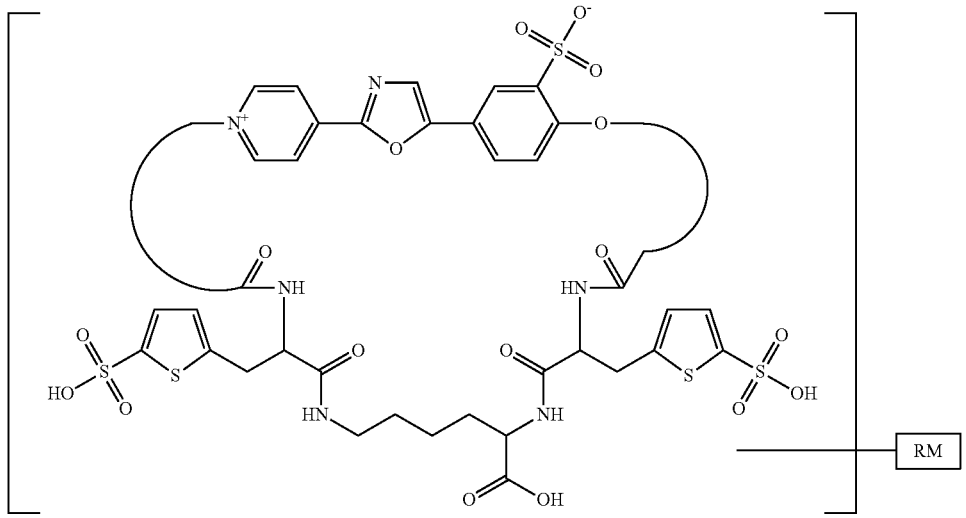
Formula 20
30
wherein RM is a chemically reactive moiety described below.
Another preferred embodiment of the invention is a compound of Formula 21
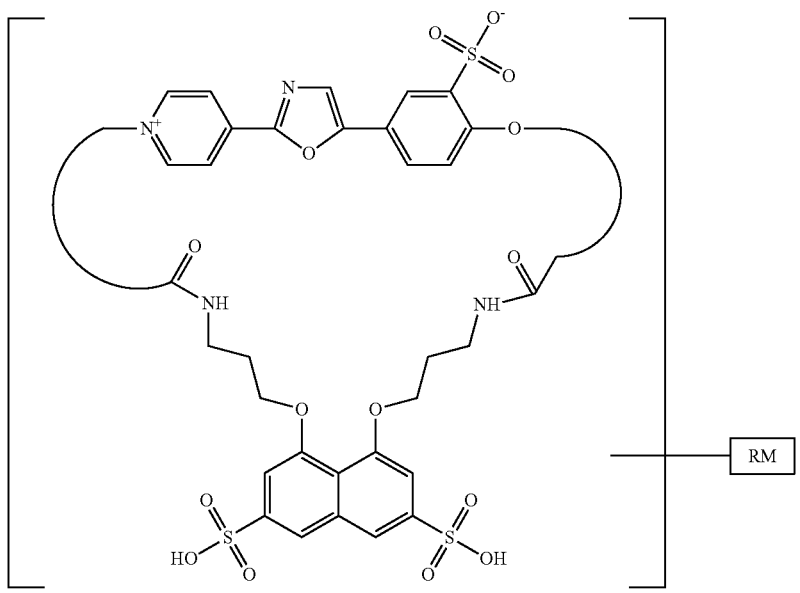
Formula 21
wherein RM is a chemically reactive moiety described below.

Another preferred embodiment of the invention is a compound of Formula 22

Formula 22

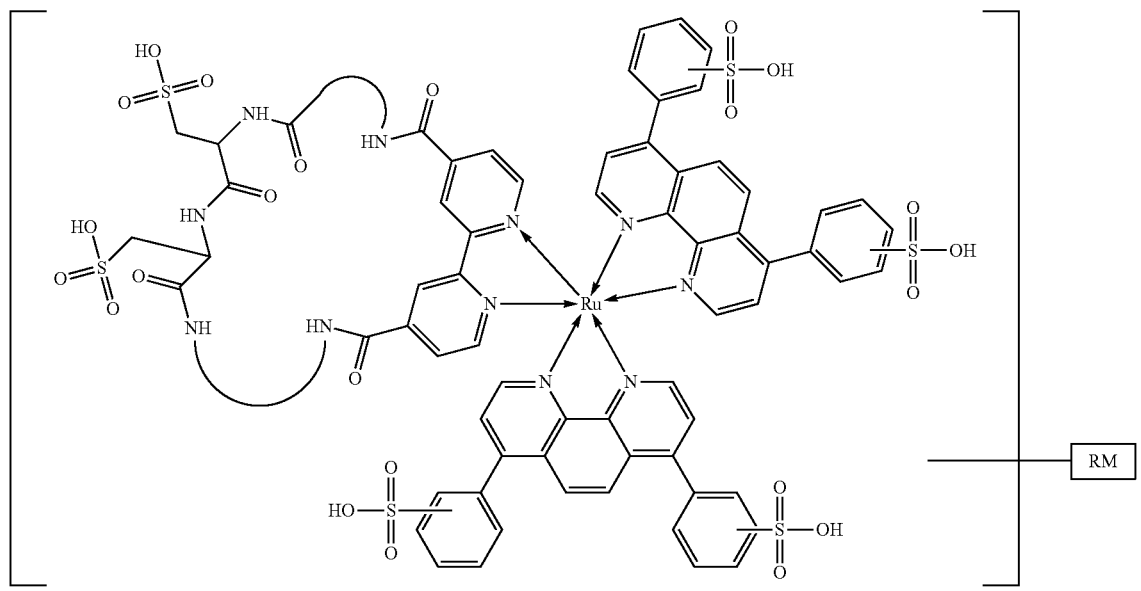

wherein RM is a chemically reactive moiety described below.

Another preferred embodiment of the invention is a compound of Formula 23

Formula 23

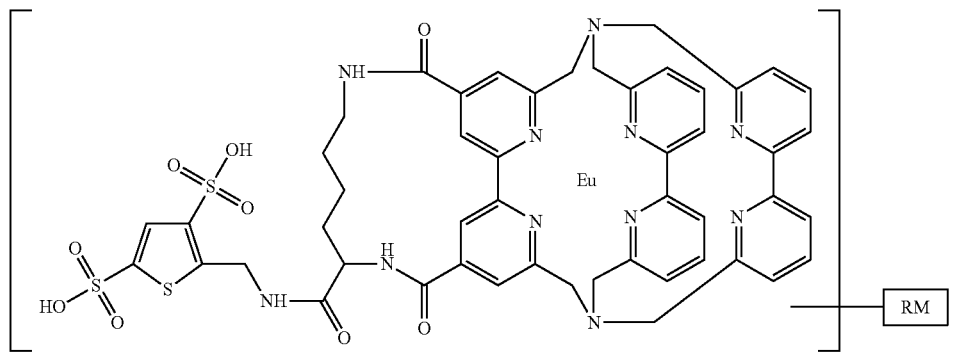

wherein RM is a chemically reactive moiety described below.

Many embodiments of the compounds of the invention possess an overall electronic charge. It is to be understood that when such electronic charges are shown to be present, they are balanced by the presence of appropriate counterions, which may or may not be explicitly identified. A biologically compatible counterion, which is preferred for some applications, is not toxic in biological applications, and does not have a substantially deleterious effect on biomolecules. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium or pyridinium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

It is to be understood that the dyes of the invention have been drawn in one or another particular electronic resonance structure. Every aspect of the instant invention applies equally to dyes that are formally drawn with other permitted resonance structures, as the electronic charge on the subject dyes is delocalized throughout the dye itself.

As used herein, a "reactive moiety", denoted "RM", refers to a moiety on a compound that is capable of chemically reacting with a functional group on a different compound to form a covalent linkage.

In one embodiment of the invention, the dye contains at least one RM, where RM is the reactive moiety that is attached to the dye by a covalent linkage L. In certain embodiments, the covalent linkage attaching the dye to RM contains multiple intervening atoms that serve as a spacer. The dyes with an RM label a wide variety of organic or inorganic substances that contain or are modified to contain functional groups with suitable reactivity, resulting in chemical attachment of the conjugated substance. As used herein, reactive moiety "RM" means moiety on the compound that is capable of chemically reacting with a functional group on a different compound to form a covalent linkage. Typically the reactive moiety is an electrophile or nucleophile that can form a covalent linkage through exposure to the corresponding functional group that is a nucleophile or electrophile, respectively. Alternatively, the reactive moiety is a photoactivatable group, and becomes chemically reactive only after illumination with light of an appropriate wavelength. Typically, the conjugation reaction between the reactive dye and the substance to be conjugated results in one or more atoms of the reactive moiety RM to be incorporated into a new linkage L attaching the dye to the conjugated substance. Selected examples of reactive moieties and linkages are shown in Table 1 where the reaction of an electrophilic group and a nucleophilic group yields a covalent linkage.

TABLE 1

RM examples that are used for preparing covalent linkages

| Electrophilic Group | Nucleophilic Group | Resulting Conjugate |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thioethers |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |

TABLE 1-continued

RM examples that are used for preparing covalent linkages

| Electrophilic Group | Nucleophilic Group | Resulting Conjugate |
|---|---|---|
| sulfonyl halides | amines/anilines | sulfonamides |
| sulfonyl halides | phenols/alcohols | sulfonate esters |

*Activated esters, as understood in the art, generally have the formula —COL, where L is a good leaving group (e.g. succinimidyloxy (—ONC$_4$H$_4$O$_2$) sulfosuccinimidyloxy (—ONC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOAlk or —OCN(Alk$_1$)NH(Alk$_2$), where Alk$_1$ and Alk$_2$, which may be the same or different, are C$_1$-C$_{20}$ alkyl, C$_1$-C$_{20}$ perfluoroalkyl, or C$_1$-C$_{20}$ alkoxy; or cyclohexyl, 3-dimethylaminopropyl, or N-morpholinoethyl).
**Acyl azides can also rearrange to isocyanates.

Choice of the reactive moiety used to attach the dye to the substance to be conjugated typically depends on the functional group on the substance to be conjugated and the type or length of covalent linkage desired. The types of functional groups typically present on the organic or inorganic substances include, but are not limited to, amines, amides, thiols, alcohols, phenols, aldehydes, ketones, phosphonates, imidazoles, hydrazines, hydroxylamines, disubstituted amines, halides, epoxides, carboxylate esters, sulfonate esters, purines, pyrimidines, carboxylic acids, olefinic bonds, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one dye, which may be the same or different, or to a substance that is additionally modified by a hapten, such as biotin. Although some selectivity can be obtained by careful control of the reaction conditions, selectivity of labeling is best obtained by selection of an appropriate reactive dye.

Typically, RM will react with an amine, a thiol, an alcohol, an aldehyde or a ketone. Preferably RM reacts with an amine or a thiol functional group. In one embodiment, RM is an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. Nos. 5,580,990; 5,714,327; 5,985,566.

Where the reactive moiety is a photoactivatable group, such as an azide, diazirinyl, azidoaryl, or psoralen derivative, the dye becomes chemically reactive only after illumination with light of an appropriate wavelength. Where RM is an activated ester of a carboxylic acid, the reactive dye is particularly useful for preparing dye-conjugates of proteins, nucleotides, oligonucleotides, or haptens. Where RM is a maleimide or haloacetamide the reactive dye is particularly useful for conjugation to thiol-containing substances. Where RM is a hydrazide, the reactive dye is particularly useful for conjugation to periodate-oxidized carbohydrates and glycoproteins, and in addition is an aldehyde-fixable polar tracer for cell microinjection. Preferably, RM is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. More preferably, RM is a succinimidyl ester of a carboxylic acid, a maleimide, an iodoacetamide, or a reactive platinum complex. Based on the above-mentioned attributes, the appropriate reactive dyes of the invention are selected for the preparation of the desired dye-conjugates, whose advantageous properties make them useful for a wide variety of applications. Particularly useful dye-conjugates include, among others, conjugates where substrate is a peptide, a nucleotide, an antigen, a steroid, a vitamin, a drug, a hapten, a metabolite, a toxin, an environmental pollutant, an amino acid, a protein, a nucleic acid, a nucleic acid polymer, a carbohydrate, a lipid, an ion-complexing moiety, a glass or a non-biological polymer. Alternatively, substrate is a cell, a cellular system, a cellular fragment, or a subcellular particle (e.g. inter alia), a virus particle, a bacterial particle, a virus component, a biological cell (such as animal cell, plant cell, bacteria, yeast, or protist), or a cellular component. Reactive dyes typically label functional groups at the cell surface, in cell membranes, organelles, or cytoplasm.

Typically substrate is an amino acid, a peptide, a protein, a tyramine, a polysaccharide, an ion-complexing moiety, a nucleoside, a nucleotide, an oligonucleotide, a nucleic acid, a hapten, a psoralen, a drug, a hormone, a lipid, a lipid assembly, a polymer, a polymeric microparticle, a biological cell or virus. More typically, substrate is a peptide, a protein, a nucleotide, an oligonucleotide, or a nucleic acid. When conjugating dyes of the invention to such biopolymers, it is possible to incorporate more dyes per molecule to increase the fluorescent signal. For example, it is possible to incorporate at least three molecules of such dyes per molecule of antibody without loss of total fluorescence, whereas fluorescence of the spectrally comparable Cy5 (wherein n=2) is strongly quenched when greater than approximately two Cy5 dyes are incorporated per antibody. These results confirm problems with Cy5 conjugates reported by others, e.g. BIOCONJU-GATE CHEM., 11, 696 (2000). The optimally labeled conjugates of the invention are typically much more fluorescent than conjugates of the Cy5 dye or 1,1'-crosslinked Cy5 at the same antibody concentration.

In one embodiment, substrate is an amino acid (including those that are protected or are substituted by phosphonates, carbohydrates, or $C_1$ to $C_{25}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins, chemokines and growth factors. In one preferred aspect, the conjugated protein is a phycobiliprotein, such as allophycocyanin, phycocyanin, phycoerythrin, allophycocyanin B, B-phycoerythrin, and phycoerythrocyanin, (for example, see U.S. Pat. No. 5,714,386 to Roederer (1998)). Particularly preferred are conjugates of R-phycoerythrin and of allophycocyanin with selected dyes of the invention that serve as excited-state energy acceptors or donors. In these conjugates, excited state energy transfer results in long wavelength fluorescence emission when excited at relatively short wavelengths.

In one aspect of the invention, substrate is a conjugated substance that is an antibody (including intact antibodies, antibody fragments, and antibody sera, etc.), an amino acid, an angiostatin or endostatin, an avidin or streptavidin, a biotin (e.g. an amidobiotin, a biocytin, a desthiobiotin, etc.), a blood component protein (e.g. an albumin, a fibrinogen, a plasminogen, etc.), a dextran, an enzyme, an enzyme inhibitor, an IgG-binding protein (e.g. a protein A, protein G, protein A/G, etc.), a fluorescent protein (e.g. a phycobiliprotein, an aequorin, a green fluorescent protein, etc.), a growth factor, a hormone, a lectin (e.g. a wheat germ agglutinin, a conconavalin A, etc.), a lipopolysaccharide, a metal-binding protein (e.g. a calmodulin, etc.), a microorganism or portion thereof (e.g. a bacteria, a virus, a yeast, etc.), a neuropeptide and other biologically active factors (e.g. a dermorphin, a deltropin, an endomorphin, an endorphin, a tumor necrosis factor etc.), a non-biological microparticle (e.g. of ferrofluid, gold, polystyrene, etc.), a nucleotide, an oligonucleotide, a peptide toxin (e.g. an apamin, a bungarotoxin, a phalloidin, etc.), a phospholipid-binding protein (e.g. an annexin, etc.), a small-molecule drug (e.g. a methotrexate, etc.), a structural protein (e.g. an actin, a fibronectin, a laminin, a microtubule-associated protein, a tublin, etc.), or a tyramide.

In another embodiment, substrate is a nucleic acid base, nucleoside, nucleotide or a nucleic acid polymer, including those that are modified to possess an additional linker or spacer for attachment of the dyes of the invention, such as an alkynyl linkage (U.S. Pat. No. 5,047,519), an aminoallyl linkage (U.S. Pat. No. 4,711,955), or a heteroatom-substituted linker (U.S. Pat. No. 5,684,142) or other linkages. In another embodiment, the conjugated substance is a nucleoside or nucleotide analog that links a purine or pyrimidine base to a phosphate or polyphosphate moiety through a noncyclic spacer. In another embodiment, the dye is conjugated to the carbohydrate portion of a nucleotide or nucleoside, typically through a hydroxyl group but additionally through a thiol or amino group (U.S. Pat. Nos. 5,659,025; 5,668,268; 5,679,785). Typically, the conjugated nucleotide is a nucleoside triphosphate or a deoxynucleoside triphosphate or a dideoxynucleoside triphosphate. Incorporation of methylene moieties or nitrogen or sulfur heteroatoms into the phosphate or polyphosphate moiety is also useful. Nonpurine and nonpyrimidine bases such as 7-deazapurines (U.S. Pat. No. 6,150, 510) and nucleic acids containing such bases can also be coupled to dyes of the invention. Nucleic acid adducts prepared by reaction of depurinated nucleic acids with amine, hydrazide or hydroxylamine derivatives provide an additional means of labeling and detecting nucleic acids, e.g. Atamna et al., PROC. NATL. ACAD. SCI. U.S.A. 97, 686-691 (2000).

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates, or peptide nucleic acids such as N-(2-aminoethyl)glycine units. When the nucleic acid is a synthetic oligonucleotide, it typically contains fewer than 50 nucleotides, more typically fewer than 25 nucleotides. Conjugates of peptide nucleic acids (PNA) (Nielsen, et al. U.S. Pat. No. 5,539, 082), may be preferred for some applications because of their generally faster hybridization rates.

In one embodiment, the conjugated oligonucleotides of the invention are aptamers for a particular target molecule, such as a metabolite, dye, hapten, or protein. That is, the oligonucleotides have been selected to bind preferentially to the target molecule. Methods of preparing and screening aptamers for a given target molecule have been previously described and are known in the art, e.g., U.S. Pat. No. 5,567,588 to Gold (1996).

In another embodiment, substrate is a carbohydrate that is typically a polysaccharide, such as a dextran, heparin, glycogen, amylopectin, mannan, inulin, starch, agarose and cellulose. Alternatively, the carbohydrate is a polysaccharide that is a lipopolysaccharide. Preferred polysaccharide conjugates are dextran, or lipopolysaccharide conjugates.

Conjugates having an ion-complexing moiety serve as indicators for calcium, sodium, magnesium, zinc, potassium, or other biologically important metal ions. Preferred ion-complexing moieties are crown ethers (U.S. Pat. No. 5,405,975); derivatives of 1,2-bis-(2-aminophenoxyethane)-N,N,N',N'-tetraacetic acid (BAPTA chelators; U.S. Pat. Nos. 5,453,517; 5,516,911 and 5,049,673); derivatives of 2-carboxymethoxyaniline-N,N-di-acetic acid (APTRA chelators; AM. J. PHYSIOL., 256, C540 (1989)); or pyridine- and phenanthroline-based metal ion chelators (U.S. Pat. No. 5,648,270); or derivatives of nitrilotriacetic acid, e.g. McMahan et al., ANAL. BIOCHEM., 236, 101-106 (1996). Preferably, the ion-complexing moiety is a crown ether chelator, a BAPTA chelator, an APTRA chelator or a derivative of nitrilotriacetic acid.

Other conjugates of non-biological materials include dye-conjugates of organic or inorganic polymers, polymeric films, polymeric wafers, polymeric membranes, polymeric particles, or polymeric microparticles (magnetic and non-magnetic microspheres); iron, gold or silver particles; conducting and non-conducting metals and non-metals; and glass and plastic surfaces and particles. Conjugates are optionally prepared by copolymerization of a dye that contains an appropriate functionality while preparing the polymer, or by chemical modification of a polymer that contains functional groups with suitable chemical reactivity. Other types of reactions that are useful for preparing dye-conjugates of polymers include catalyzed polymerizations or copolymerizations of alkenes and reactions of dienes with dienophiles, transesterifications or transaminations. In another embodiment, the conjugated substance is a glass or silica, which may be formed into an optical fiber or other structure.

In one embodiment, conjugates of biological polymers such as peptides, proteins, oligonucleotides, nucleic acid polymers are also labeled with at least a second luminescent dye, which is optionally an additional dye of the present invention, to form an energy-transfer pair. In some aspects of the invention, the labeled conjugate functions as an enzyme substrate, and enzymatic hydrolysis disrupts the energy transfer. In another embodiment of the invention, the energy-transfer pair that incorporates a dye of the invention is conjugated to an oligonucleotide that displays efficient fluorescence quenching in its hairpin conformation (e.g., the so-called "molecular beacons", Tyagi, et al., NATURE BIOTECHNOLOGY, 16, 49 (1998)).

The preparation of dye conjugates using reactive dyes is well documented, e.g. Hermanson G T, BIOCOJUGATE TECHNIQUES, Academic Press, New York (1996); Haugland R P, METHODS MOL. BIOL., 45, 205-21 (1995); and Brinkley, BIOCONJUGATE CHEM., 3, 2 (1992). Conjugates typically result from mixing appropriate reactive dyes and the substance to be conjugated in a suitable solvent in which both are soluble. The majority of the dyes of the invention are readily soluble in aqueous solutions, facilitating conjugation reactions with most biological materials. For those reactive dyes that are photoactivated, conjugation requires illumination of the reaction mixture to activate the reactive dyes.

Synthesis

Figure 4:
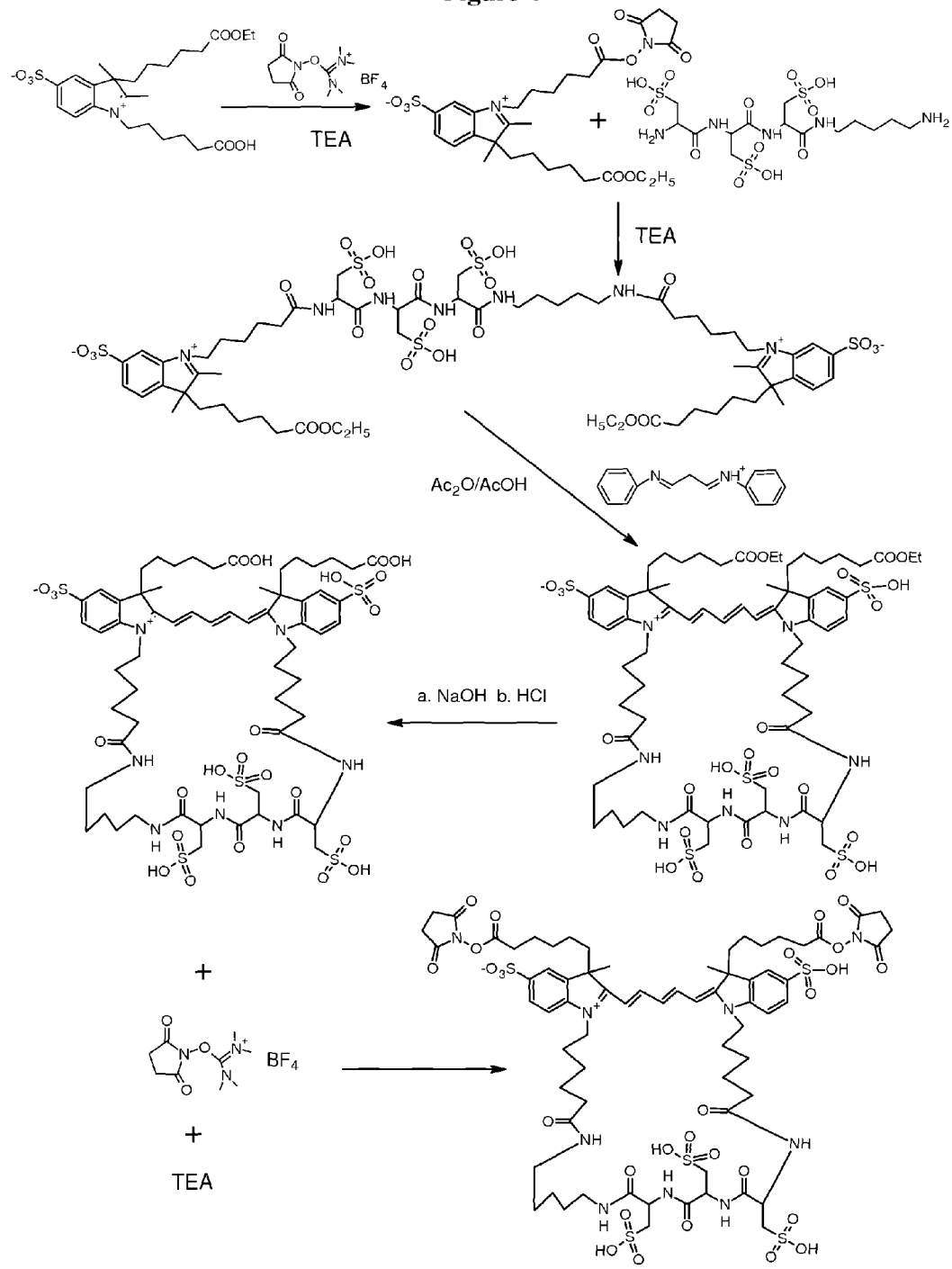
FIG. 4. Synthesis of a cyanine that has a water-soluble 1,1'-crosslinked intramolecular bridge FIG. 5. Synthesis of a cyanine that has a water-soluble 1,3'-crosslinked intramolecular bridge FIG. 6. Synthesis of a cyanine that has a water-soluble 3,3'-crosslinked intramolecular bridge FIG. 7. Synthesis of an oxazole that has a water-soluble intramolecular bridge FIG. 8. Synthesis of a rhodamine that has a water-soluble intramolecular bridge FIG. 9. Synthesis of a europium complex that has a water-soluble intramolecular bridge FIG. 10. Flow cytometry comparison of mouse anti human CD4 conjugates of Compound 49 and Pacific Orange (Invitrogen). Normal human blood is incubated with mouse anti human CD4 conjugates of Compound 108 and Pacific Orange. After incubation with the antibody conjugates, the treated blood is decanted and the pellet is suspended in 0.5 ml of 0.5% BSA/PBS for analysis on a BD™ LSRII Flow Cytometer (BD Biosciences, San Jose, Calif.). The analysis is performed with the 405 nm excitation of a violet laser, collecting the emission through a 550/40 nm bandpass filter.
Figure 5:
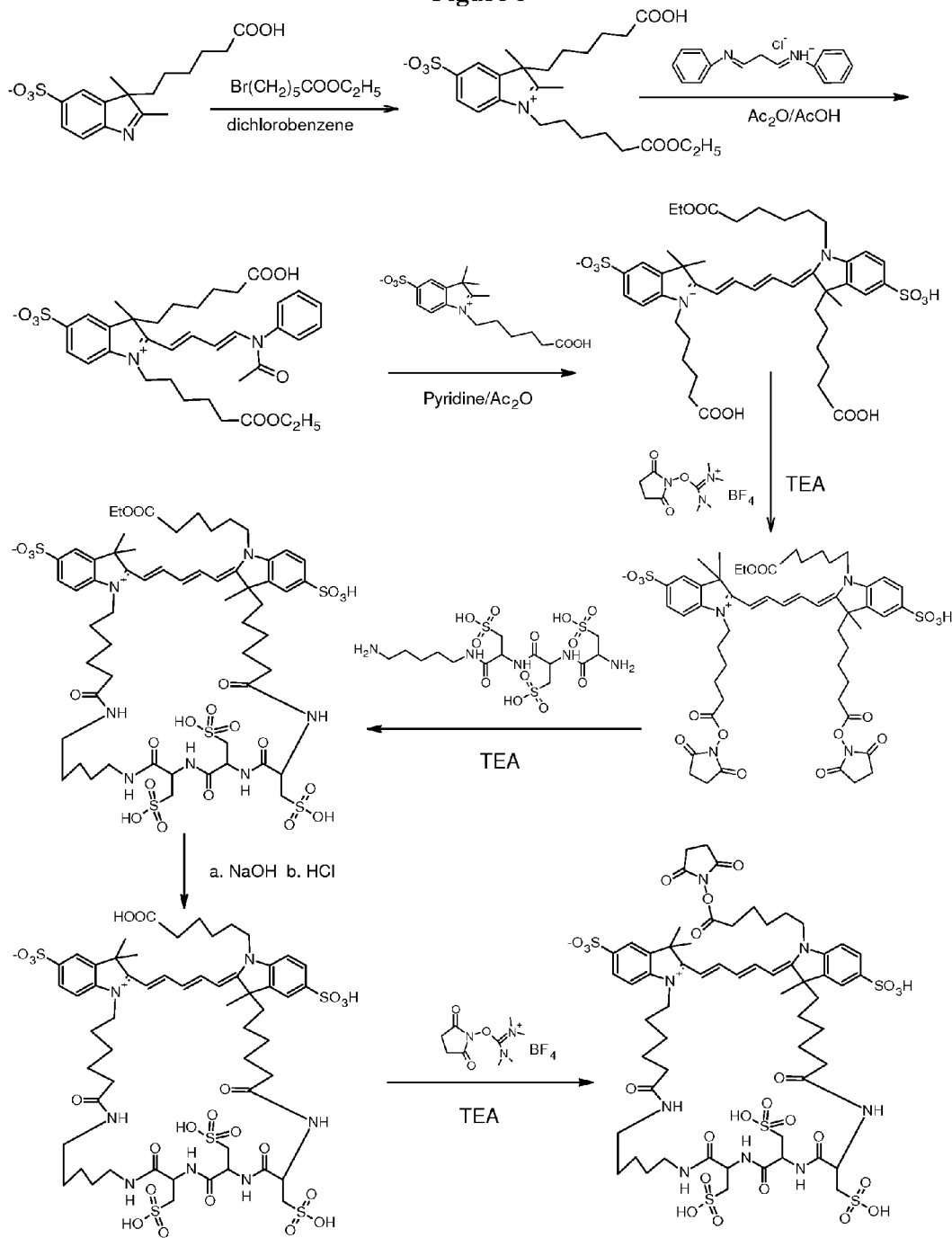
Figure 6:
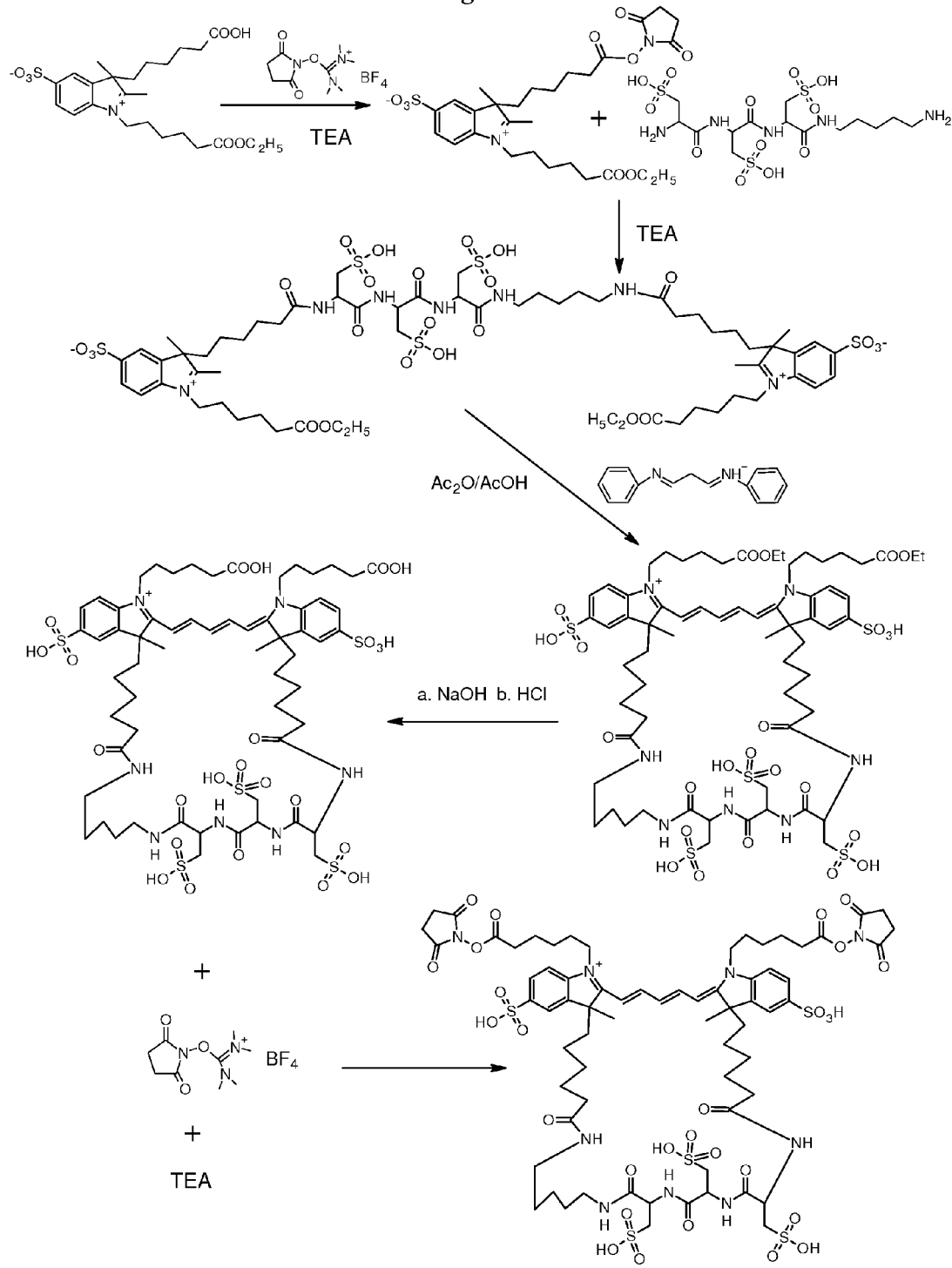
Figure 7:
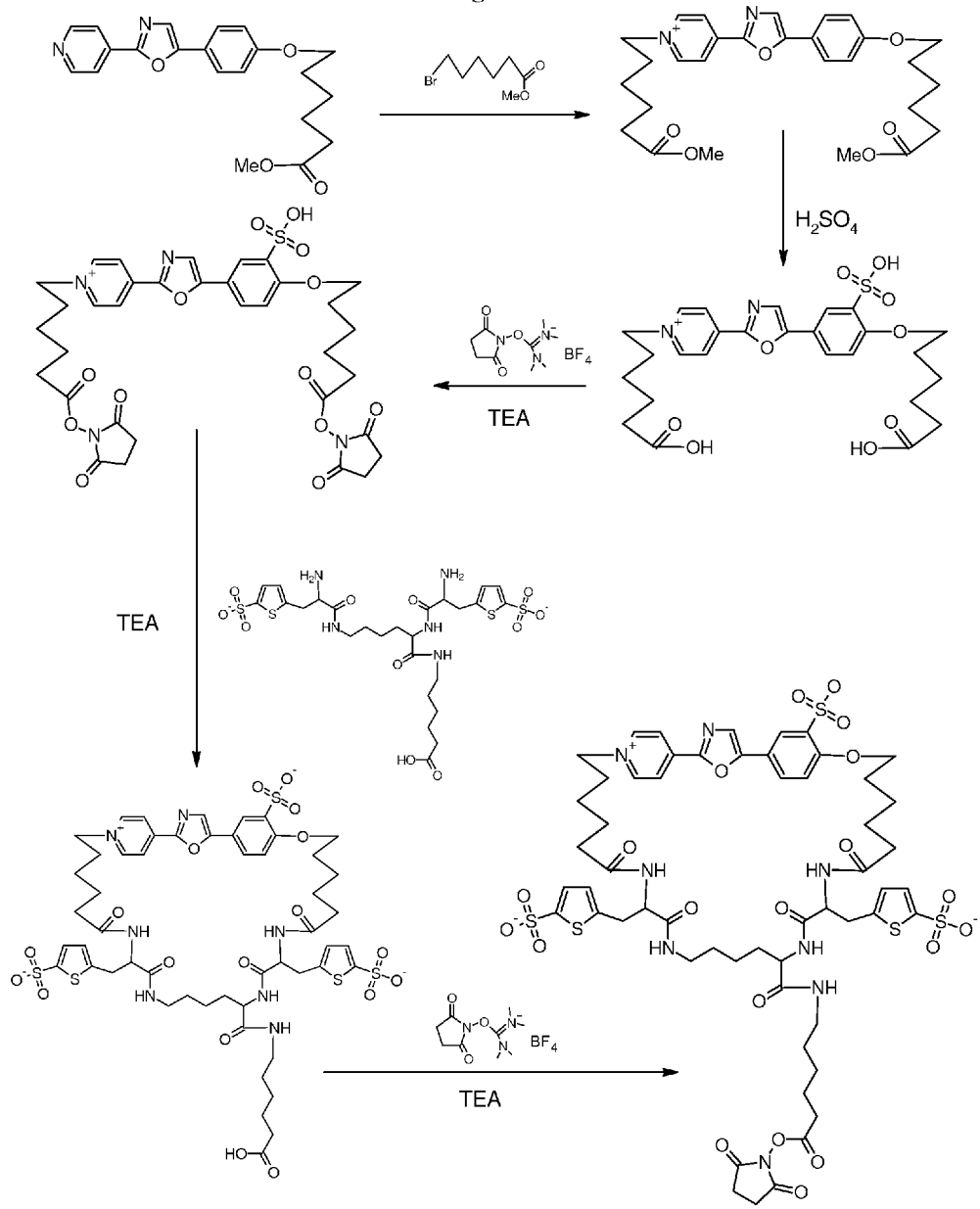
Figure 8:
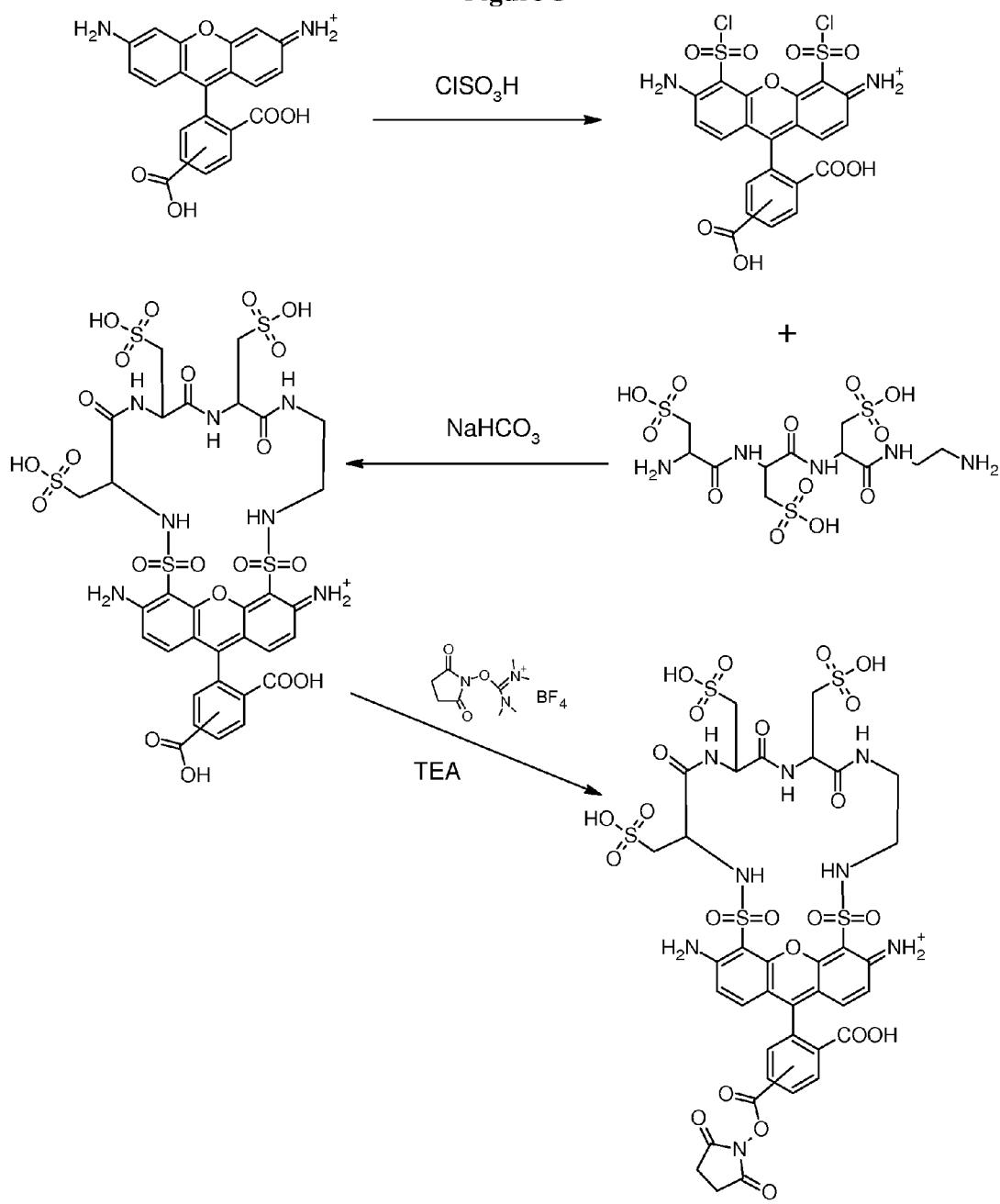
Figure 9:
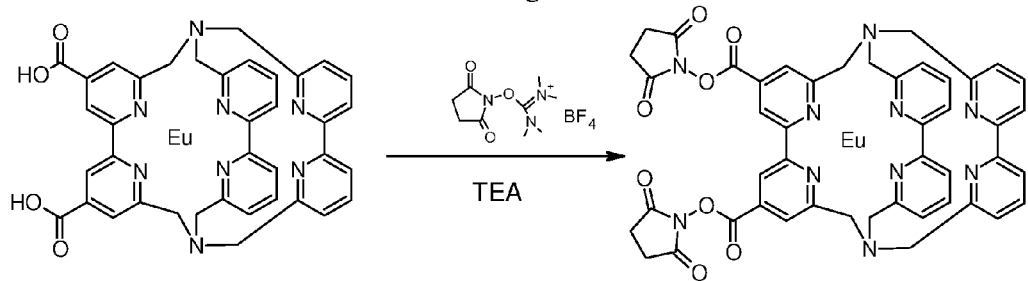
Figure 9:
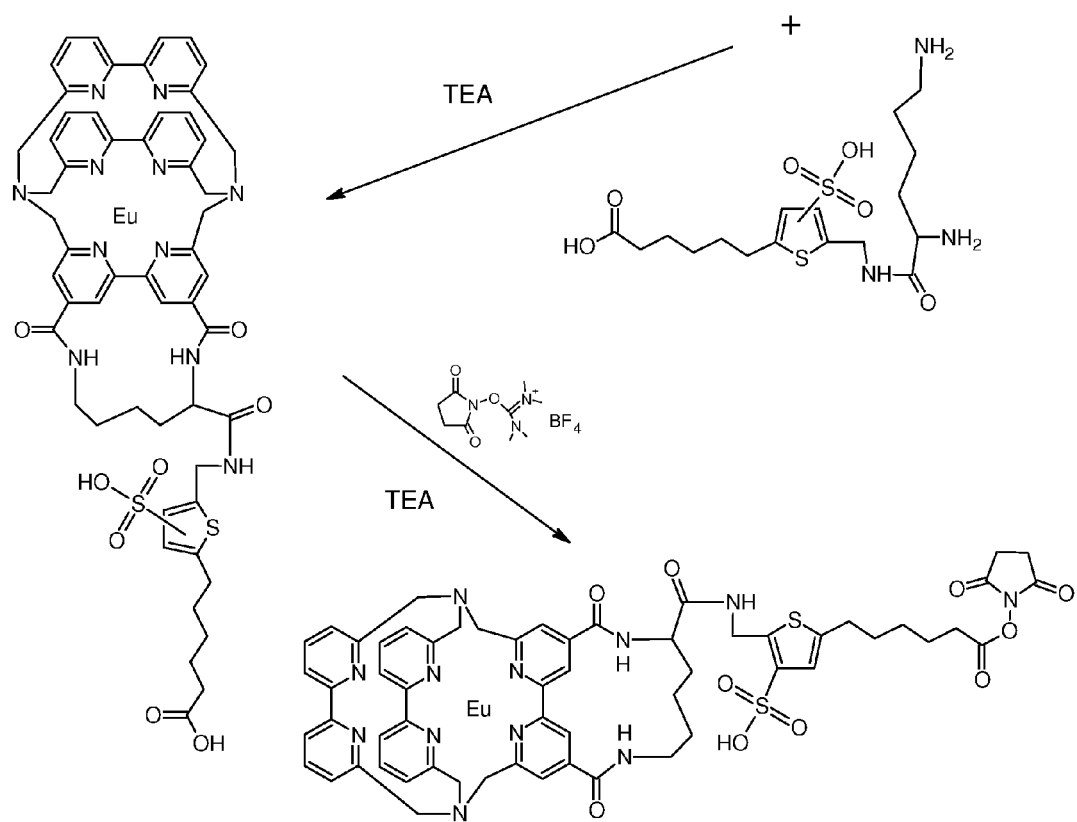

The luminescent dyes of the invention can be readily synthesized using two different routes. (1). A WSB crosslinker is prepared first. The WSB linker can be made using the standard liquid phase chemistry. It might be also prepared by the standard solid phase peptide synthesis if the WSB has more than 3 water-soluble groups. The WSB can be coupled to a luminescent dye that contains two functional groups. This strategy is illustrated in FIGS. 5, 7, 8 and 9. (2). A WSB is coupled to a luminescent dye precursor that is later condensed to give the desired dye. This strategy is illustrated in FIGS. 4 and 6.

The syntheses of luminescent dyes are well described in the literature. These basic structures are optionally further substituted, during or after synthesis, to give the corresponding dye substituents as defined above. For carbocyanines, the key intermediates are readily synthesized by a reaction that is analogous to a Fischer indole synthesis (Sundberg, "THE CHEMISTRY OF INDOLES" 1970, Academic Press; Hamer, "THE CYANINE DYES AND RELATED COMPOUNDS", 1964, John Wiley & Sons). Synthesis of the cyanine dyes of the invention depends on initial preparation of key indoline intermediate. Licha, et al., U.S. Pat. No. 6,083,485 (2000) described a typical synthesis of indoline intermediate. These basic structures are optionally further substituted, during or after synthesis, to give the corresponding dye substituents as defined above. The novel key intermediates are readily synthesized by a reaction that is analogous to a Fischer indole synthesis or through the condensations of phenylendiamine with a carbonyl compound. A WSB-substituted carbocyanine is illustrated in FIG. 4.

Synthesis of the cyanine dyes of the invention, where attachment is at the bridged and conjugated double bonds, depends on initial preparation of certain key bridged intermediates. For example, N,N'-diphenylformamidine, triethylorthoformate malonaldehyde bis(phenyl)mine) hydrochloride, 1,1,3-trimethoxypropane, 1,1,3,3-tetramethoxypropane and glutaconaldehyde dianil monochloride are the well-known bridged intermediates used in the synthesis of carbocyanines. More examples of appropriate carbocyanines that have bridged and conjugated double bonds have been previously described in the literature of U.S. Pat. No. 7,465,810 to Diwu et al; U.S. Pat. No. 5,831,098 to Ollmann, Jr (1998); U.S. Pat. No. 6,086,737 to Patonay, et al. (2000); U.S. Pat. No. 6,048,982 to Waggoner (2000); and U.S. Pat. No. 5,453,505 to Lee, et al. (1995); U.S. Pat. No. 5,639,874 to Middendorf, et al. (1997); U.S. Pat. No. 3,864,644 to Lincoln, et al. (1975); U.S. Pat. No. 4,011,086 to Simson (1977). The typical total synthesis of carbocyanines substituted at the bridged and conjugated carbon atoms with an RM is illustrated in FIGS. 4, 5 and 6.

For the synthesis of carbocyanines, an appropriately substituted aryl hydrazine, which is typically an appropriately substituted phenylhydrazine, is reacted with an appropriately substituted methyl ketone to yield a 3,3-disubstituted 2-methylindole derivative. It is particularly suitable to utilize a sulfonated phenylhydrazine derivative or a sulfonated naphthylhydrazine derivative to increase the solubility of the final dye. The 3,3-disubstituted-2-methylindole is then quaternized on the nitrogen atom to an indolium derivative with an alkylating agent that is typically an alkyl halide such as ethyl iodide, an alkylsulfonate such as methyl p-toluenesulfonate or a cyclic sulfonate such as propanesultone or butanesultone. Typically, the key indolium or benzoindolium intermediates are sulfonated one or more times before or after quaternization and subsequent condensation with the benzazolium moiety and polymethine moiety to form the subject dyes. Variations on these methods are well known in the art that yield substituents on the polymethine bridge or on the indolium or benzolium portion of the dye precursor.

The azacarbocyanine dyes of the present invention can be analogously synthesized, e.g., Leung W, et al., WO 02/26891; Brooker, et al., J. AM. CHEM. SOC., 64, 199 (1942); Chu-Moyer, et al. J. ORG. CHEM., 60, 5721(1995); Turner, J. ORG. CHEM., 48, 3401 (1983); Khanna, et al. J. ORG. CHEM., 60, 960 (1995); British Patent No. 870,753 to Ficken, et al. (1961). In general, the synthesis of these dyes requires three precursors: the appropriate benzazolium or azabenzazolium salt, and a source for the polymethine spacer. Typically each component is selected so as to incorporate the appropriate chemical substituents, or functional groups (e.g. RM) that can be converted to the appropriate substituents. The chemistry that is required to prepare and combine these precursors so as to yield any of the subject derivatives is generally well understood by one skilled in the art.

Xanthene dyes are prepared from resorcinol derivatives (to give fluoresceins), 3-aminophenols (to give rhodamines) or the combinations of resorcinol and 3-aminophenols (to give rhodols), e.g., U.S. Pat. No. 7,704,284 to Eliu, et al. (2010); U.S. Pat. No. 7,491,830 to Lam, et al. (2009); U.S. Pat. No. 7,344,701 to Reddington, et al. (2008); U.S. Pat. No. 6,229,055 to Klaubert, et al. (2001); U.S. Pat. No. 6,130,101 to Mao et al. (2000); Venkataraman, "THE CHEMISTRY OF SYNTHETIC DYES", Volume 2, 1952.

Oxazole dyes are typically synthesized the condensation of acid derivatives (e.g., acyl chlorides, anhydrides or activatd esters) with 2-aminoketones followed by dehydration to give the desired oxazole dyes, e.g., Kauffman et al., J. Heterocyclic Chem. 1992, 29, 1245; Litak and Kauffman, J. Heterocyclic Chem. 1994, 31, 457; Diwu et al., Photochem. Photobiol. 1997, 66, 424; U.S. Pat. Appl. No. 2007007754 to Buller et al. Other alternative synthetic methods for preparing a variety of oxazole dyes are also known in the literature (Chien, "SYNTHESIS OF OXAZOLE LASER DYES", Southern Illinois University at Carbondale, 1988; Fisher, "OXAZOLE CHEMISTRY: ELECTROPHILIC AND NUCLEOPHILIC ADDITIONS, INTER- AND INTRA-MOLECULAR CYCLOADDITIONS AND OXAZOLE FORMATION VIA AMIDOALKYLATION", 1991; Palmer, "THE CHEMISTRY OF HETEROCYCLIC COMPOUNDS, OXAZOLES: SYNTHESIS, REACTIONS, AND SPECTROSCOPY, VOLUME 60, PARTS A & B, CHEMISTRY OF HETEROCYCLIC COMPOUNDS: A SERIES OF MONOGRAPHS", 2004).

Bodipys are synthesized for the condensation of an appropriately substituted pyrrole with a carbonyl compound followed by the $BF_3$ complexation to give the desired Bodipy dyes, e.g., U.S. Pat. No. 5,451,663 (1995) to Kang et al; U.S. Pat. No. 5,433,896 (1995) to Kang et al; U.S. Pat. No. 5,187,288 (1993) to Kang et al; U.S. Pat. No. 5,248,782 (1993) to Kang et al; U.S. Pat. No. 4,774,339 (1988) to Kang et al. These basic structures are optionally further substituted, during or after synthesis, to give the corresponding dye substituents as defined above. The synthesis of pyrrole precursors is very well known in the literature (Jones and Bean, "CHEMISTRY OF PYRROLES, ORGANIC CHEMICAL MONOGRAPH", 1977; Jones, "CHEMISTRY OF HETEROCYCLIC COMPOUNDS, VOLUME 48, PART 1 AND PART 2, THE SYNTHESIS AND THE PHYSICAL AND CHEMICAL ASPECTS OF THE PYRROLE RING, THE SYNTHESIS, REACTIVITY, AND PHYSICAL PROPERTIES OF SUBSTITUTED PYRROLES", 1992).

The synthesis of a metal complex is greatly dependent on the ligands, such as bipyridine derivatives that are well studied, e.g., U.S. Pat. No. 6,329,205 to Diwu et al; U.S. Pat. No. 6,316,267 to Bhalgat, et al; U.S. Pat. No. 7,087,384 to Autiero, et al. It is recognized that there are many possible variations that may yield equivalent results. The synthesis of metal ligands is well described in the literature (Bunzli, CHEM. REV. 2010, 110, 2729; BIOCONJUGATE CHEM. 2001, 12, 7; Bunzli and Piguet, CHEM. REV. 2002, 102, 1897; Kido, CHEM. REV. 2002, 102, 2357; Tsukube and Shinoda, CHEM. REV. 2002, 102, 2389).

The methods for the synthesis of dyes that contain a variety of reactive moieties such as those described in Table 1 are well documented in the art. Particularly useful are amine-reactive dyes such as "activated esters" of carboxylic acids, which are typically synthesized by coupling a carboxylic acid to a relatively acidic "leaving group". Other preferred amine-reactive moieties include sulfonyl halides, which are prepared from sulfonic acids using a halogenating agent such as $PCl_5$ or $POCl_3$; halotriazines, which are prepared by the reaction of cyanuric halides with amines; and isocyanates or isothiocyanates, which are prepared from amines and phosgene or thiophosgene, respectively.

Dyes containing amines and hydrazides are particularly useful for conjugation to carboxylic acids, aldehydes and ketones. Most often these are synthesized by reaction of an activated ester of a carboxylic acid or a sulfonyl halide with a diamine, such as cadaverine, or with a hydrazine. Alternatively, aromatic amines are commonly synthesized by chemical reduction of a nitroaromatic compound. Amines and hydrazines are particularly useful precursors for synthesis of thiol-reactive haloacetamides or maleimides by standard methods (Hermanson, "BIOCOJUGATE TECHNIQUES", Academic Press, New York (1996); Brinkley, BIOCONJUGATE CHEM 3, 2-13 (1992). Selected embodiments of the invention are given in Table 2.

TABLE 2
Example compounds of the invention
| Dye | Structure |
|---|---|
| 100 | 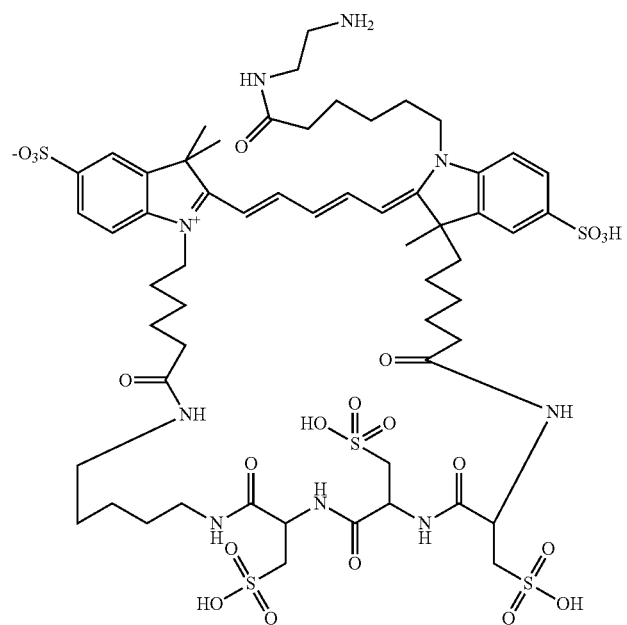 |
| 101 | 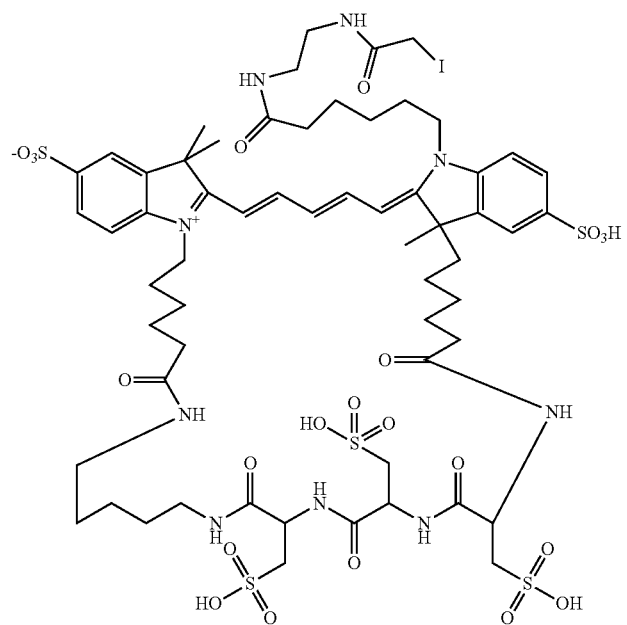 |

TABLE 2-continued
Example compounds of the invention
| Dye | Structure |
| --- | --- |
| 102 | 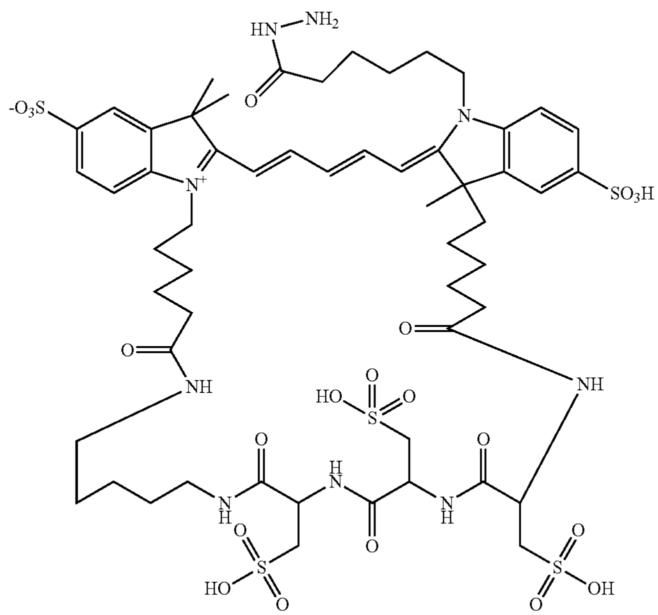 |
| 103 | 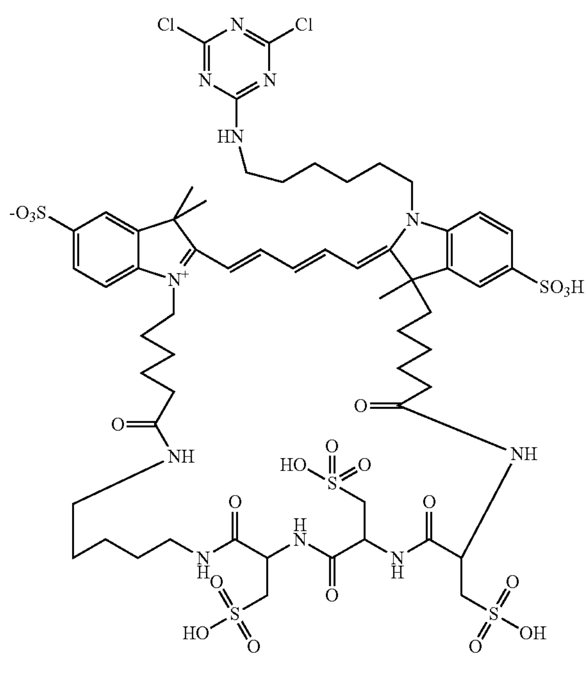 |
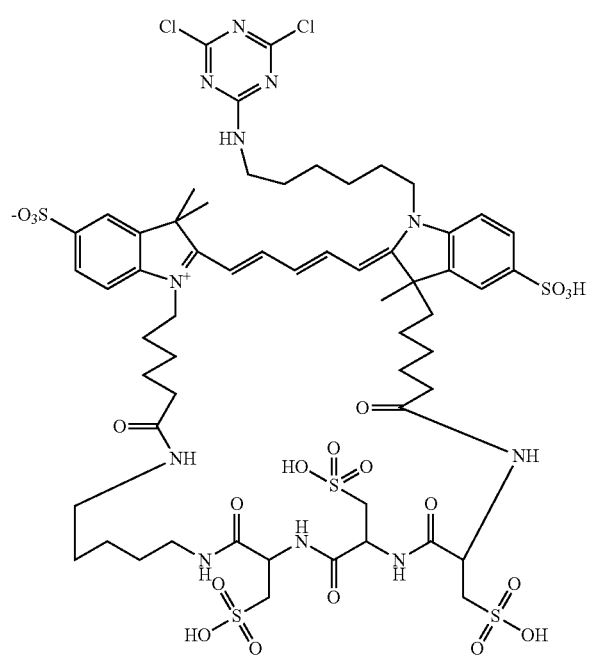

TABLE 2-continued
Example compounds of the invention
| Dye | Structure |
|---|---|
| 104 | 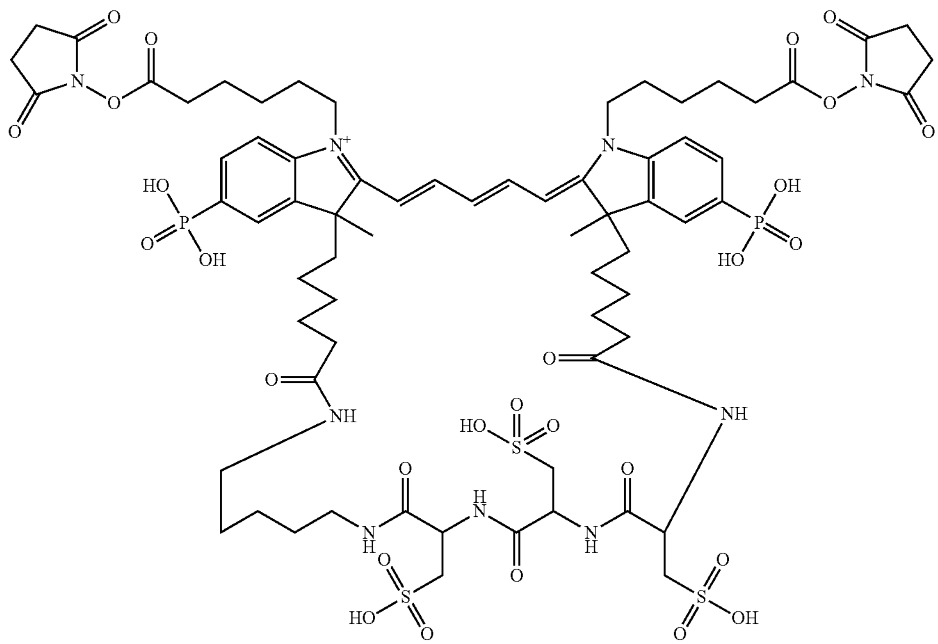 [SMILES: CC12CCCCCC(=O)NCCCCCNC(=O)C(CS(=O)(=O)O)NC(=O)C(CS(=O)(=O)O)NC(=O)C(CS(=O)(=O)O)NC(=O)CCCCCC3(C)/C(=C/C=C/C=C/C1=[N+](CCCCCC(=O)ON1C(=O)CCC1=O)c1ccc(P(=O)(O)O)cc12)N(CCCCCC(=O)ON1C(=O)CCC1=O)c1ccc(P(=O)(O)O)cc13] |
| 105 | 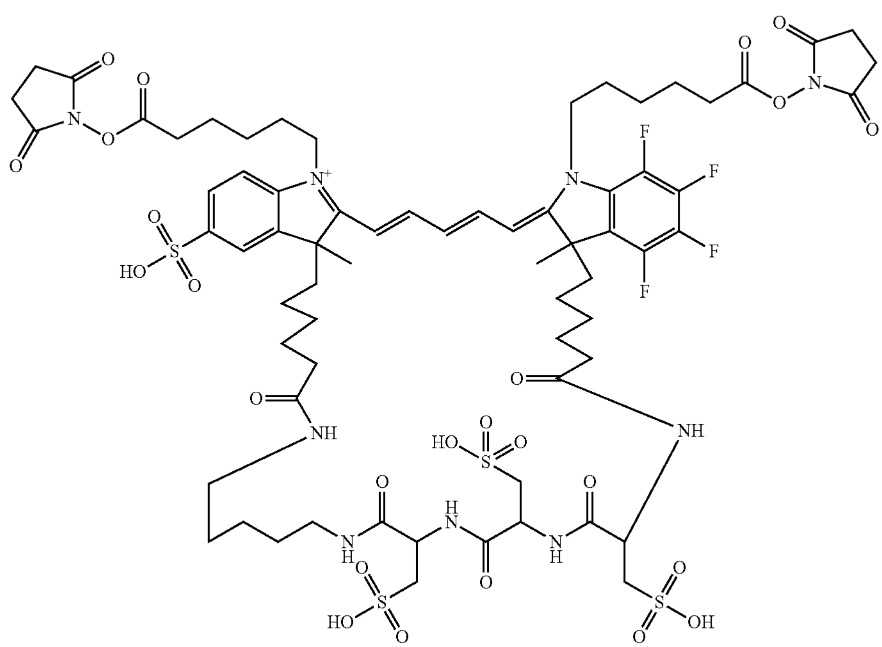 [SMILES: CC12CCCCCC(=O)NCCCCCNC(=O)C(CS(=O)(=O)O)NC(=O)C(CS(=O)(=O)O)NC(=O)C(CS(=O)(=O)O)NC(=O)CCCCCC3(C)/C(=C/C=C/C=C/C1=[N+](CCCCCC(=O)ON1C(=O)CCC1=O)c1ccc(S(=O)(=O)O)cc12)N(CCCCCC(=O)ON1C(=O)CCC1=O)c1c(F)c(F)c(F)c(F)c13] |
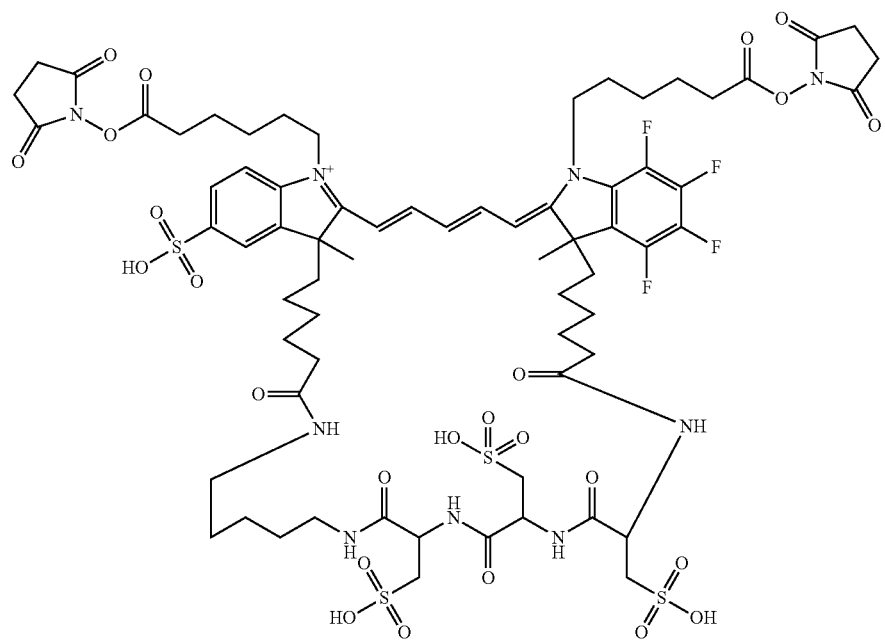

37
TABLE 2-continued
Example compounds of the invention
| Dye | Structure |
|---|---|
| 106 | 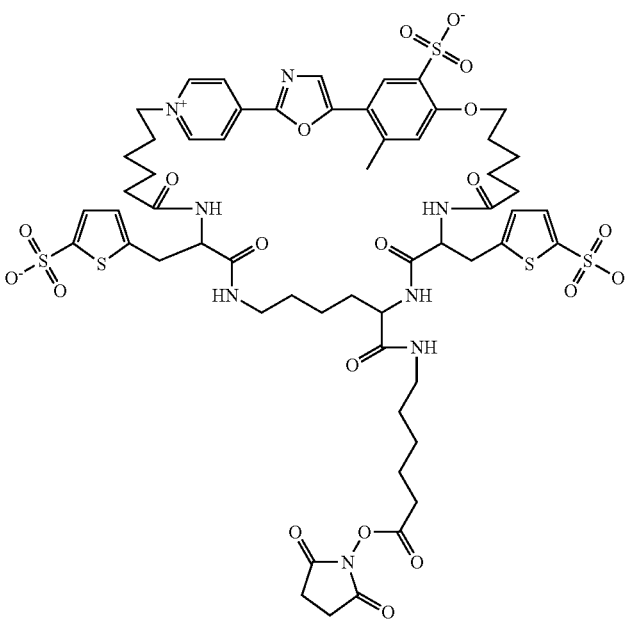 |
| 107 | 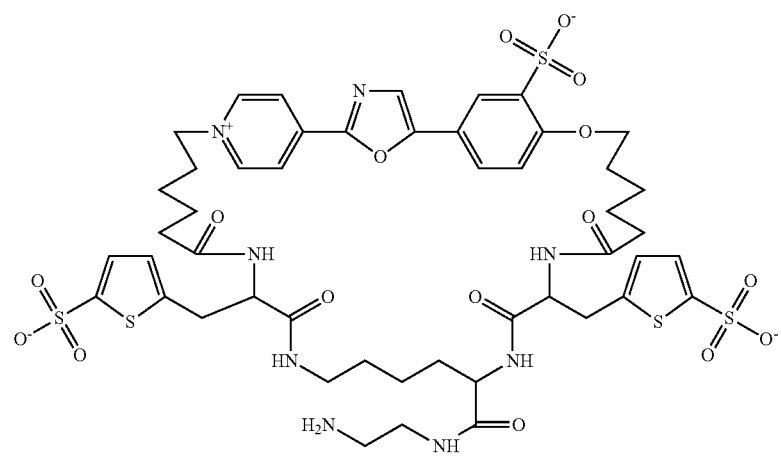 [SMILES: NCCNC(=O)C1CCCCNC(=O)C(Cc2ccc(S(=O)(=O)[O-])s2)NC(=O)CCCCC[n+]2ccc(cc2)-c2ncc(o2)-c2ccc(c(S(=O)(=O)[O-])c2)OCCCCCC(=O)NC(Cc2ccc(S(=O)(=O)[O-])s2)C(=O)N1] |

TABLE 2-continued
Example compounds of the invention
| Dye | Structure |
|---|---|
| 108 | 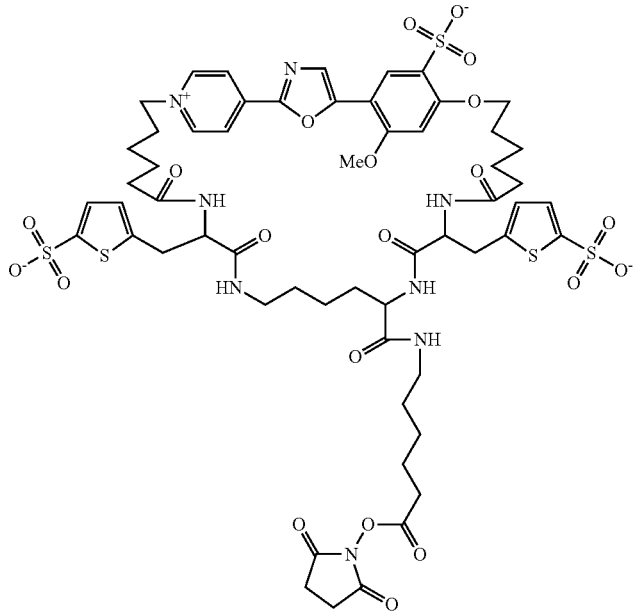 [SMILES: COc1cc2c(S(=O)(=O)[O-])cc1-c1cnc(o1)-c1cc[n+](cc1)CCCCCC(=O)NC(Cc1ccc(S(=O)(=O)[O-])s1)C(=O)NCCCCC(C(=O)NCCCCCC(=O)ON1C(=O)CCC1=O)NC(=O)C(Cc1ccc(S(=O)(=O)[O-])s1)NC(=O)CCCCCO2] |
| 109 | 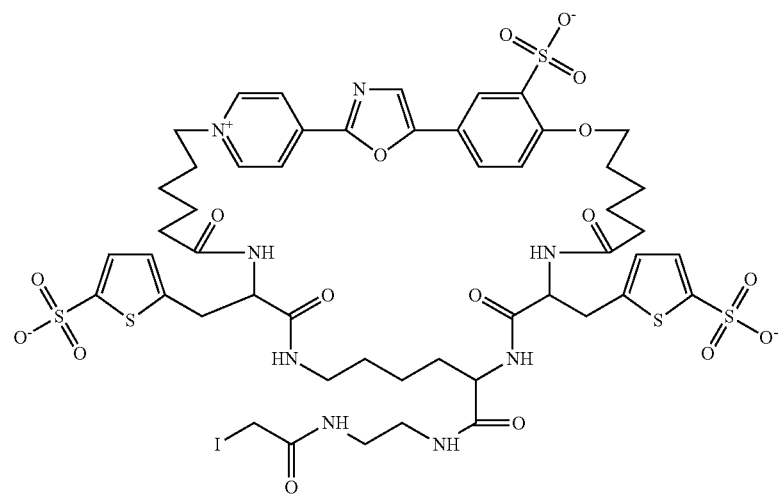 [SMILES: O=C(CI)NCCNC(=O)C1CCCCNC(=O)C(Cc2ccc(S(=O)(=O)[O-])s2)NC(=O)CCCCC[n+]2ccc(cc2)-c2ncc(o2)-c2ccc(c(S(=O)(=O)[O-])c2)OCCCCCC(=O)NC(Cc2ccc(S(=O)(=O)[O-])s2)C(=O)N1] |

TABLE 2-continued
Example compounds of the invention
| Dye | Structure |
|---|---|
| 110 | 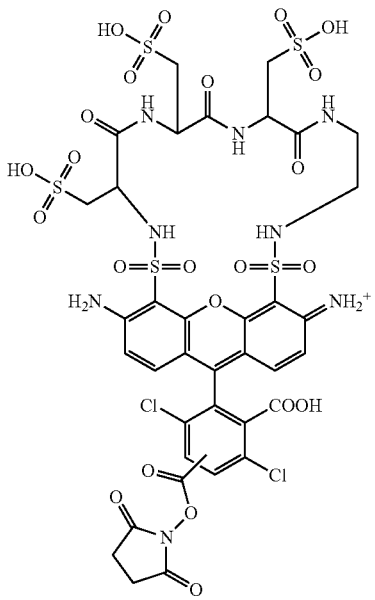 |
| 111 | 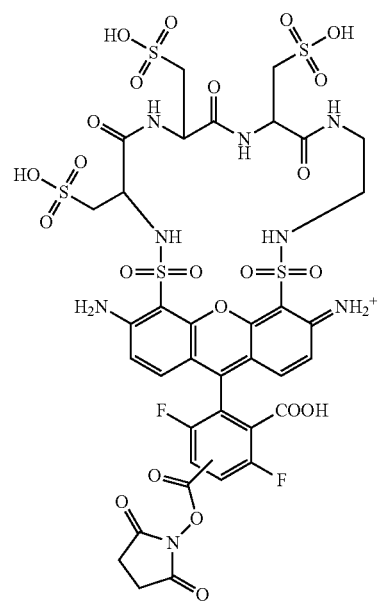 |

TABLE 2-continued
Example compounds of the invention
| Dye | Structure |
|---|---|
| 112 | 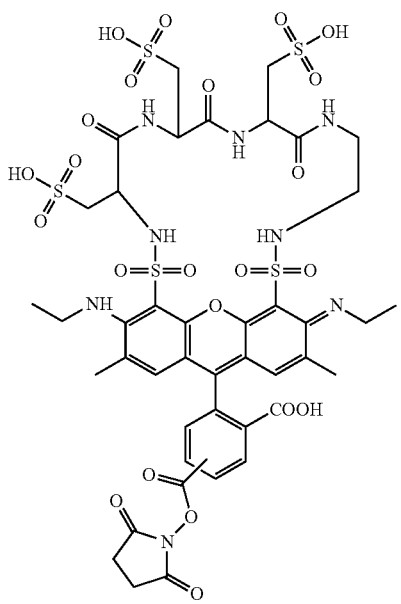 |
| 113 | 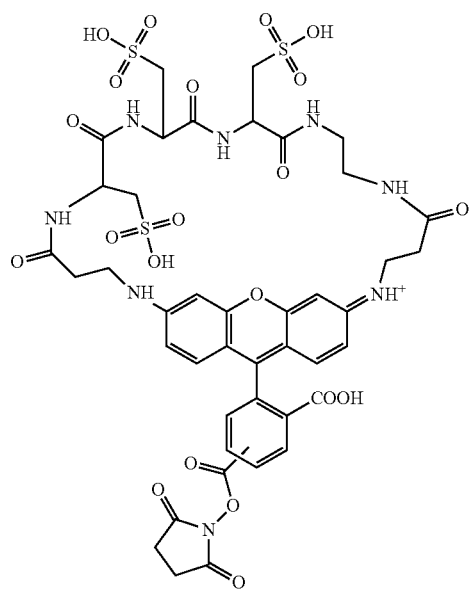 |

TABLE 2-continued
Example compounds of the invention
| Dye | Structure |
| --- | --- |
| 114 | 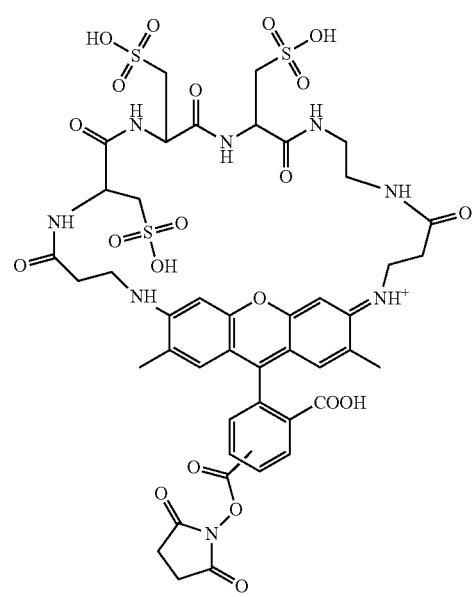 |
| 115 | 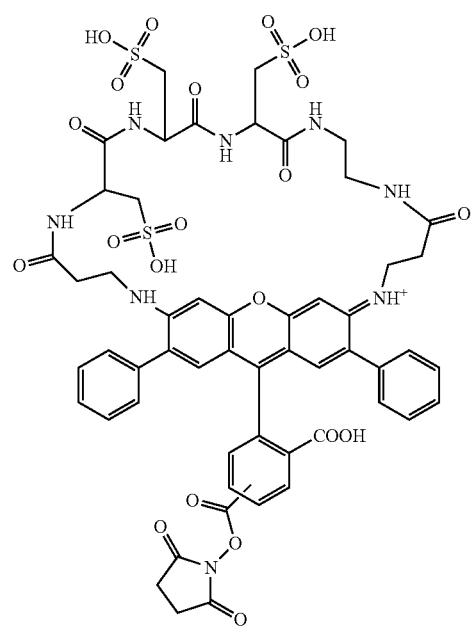 |

TABLE 2-continued
Example compounds of the invention
| Dye | Structure |
|---|---|
| 116 | 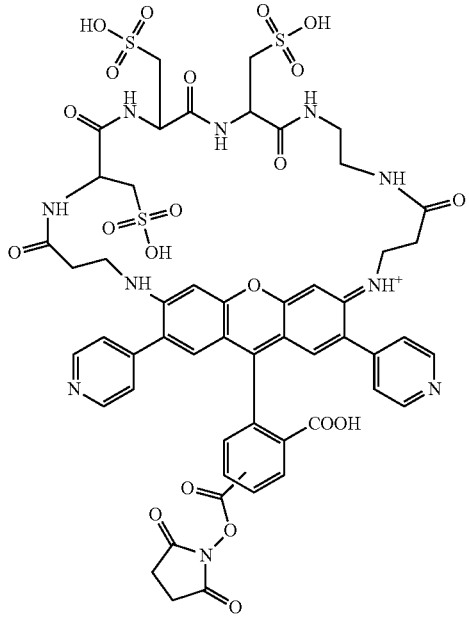 |
| 117 | 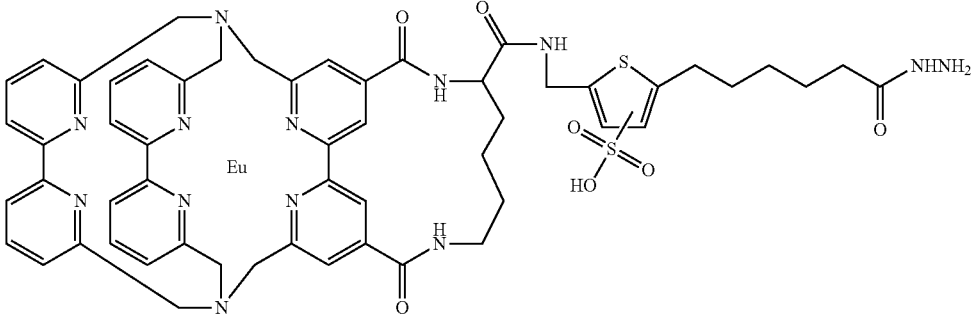 |
| 118 | 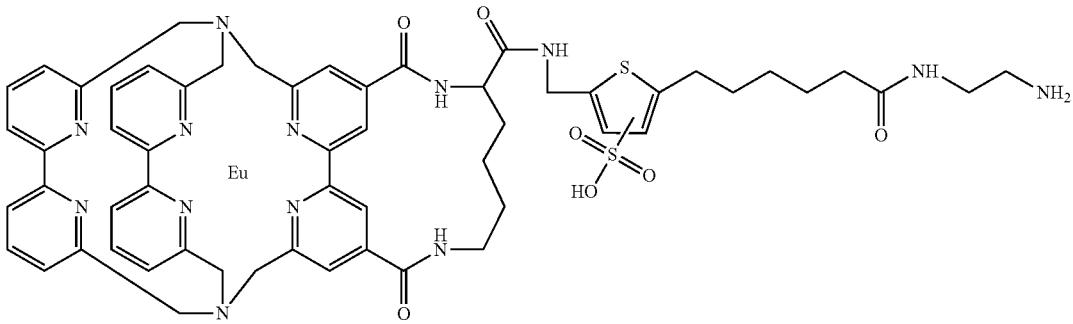 |

TABLE 2-continued

Example compounds of the invention

| Dye | Structure |
|---|---|
| 119 | (structure) |
| 120 | (structure) |
| 121 | (structure) |

TABLE 2-continued
Example compounds of the invention
| Dye | Structure |
|---|---|
| 122 | 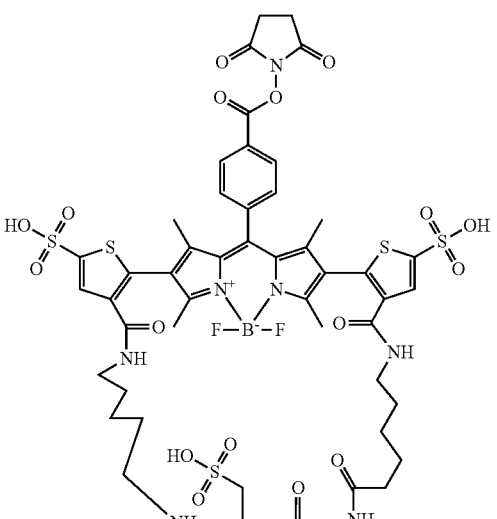 |
| 123 | 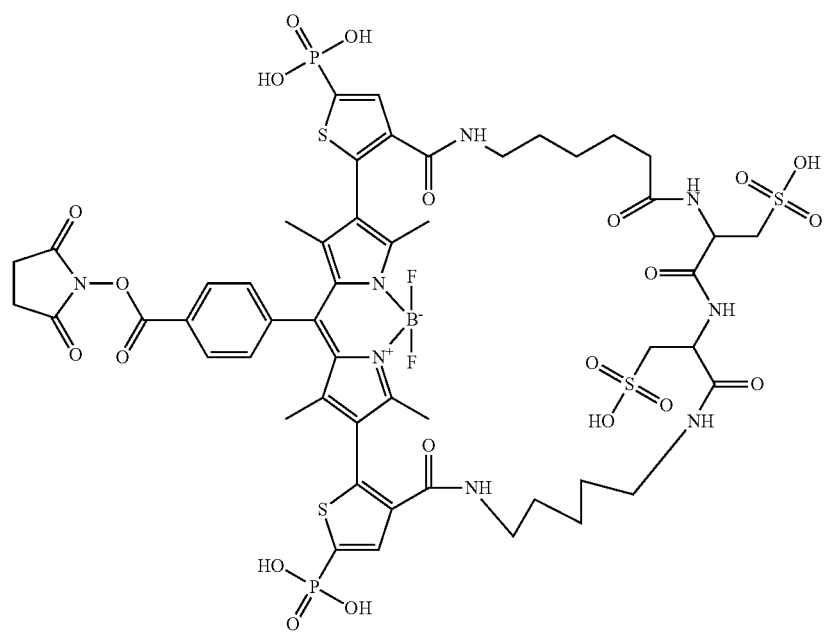 [SMILES: CC1=C2C(C)=[N+]3C1=C(c1ccc(C(=O)ON4C(=O)CCC4=O)cc1)c1c(C)c(c(C)n1[B-]3(F)F)-c1sc(P(=O)(O)O)cc1C(=O)NCCCCCC(=O)NC(CS(=O)(=O)O)C(=O)NC(CS(=O)(=O)O)C(=O)NCCCCCNC(=O)c1cc(P(=O)(O)O)sc12] |

TABLE 2-continued

Example compounds of the invention

| Dye | Structure |
| --- | --- |
| 124 | 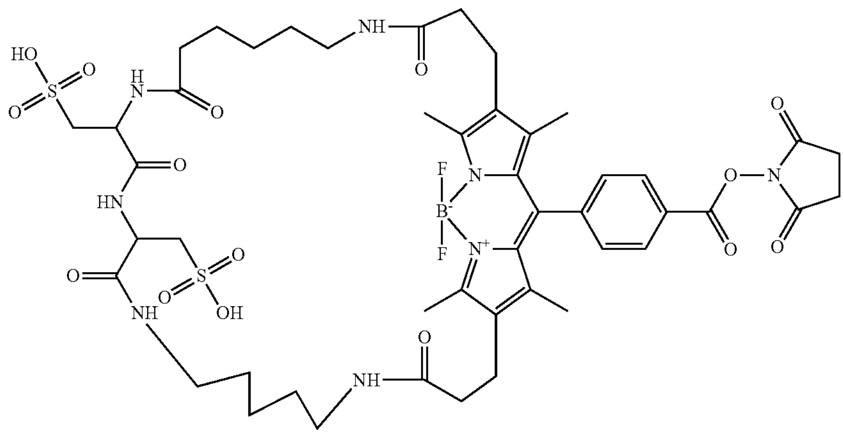 [SMILES: CC1=C2CCC(=O)NCCCCCNC(=O)C(CS(=O)(=O)O)NC(=O)C(CS(=O)(=O)O)NC(=O)CCCCCNC(=O)CCc3c(C)c4n(c3C)[B-](F)(F)[N+](=C2C)C1=C4c1ccc(C(=O)ON2C(=O)CCC2=O)cc1] |
| 125 | 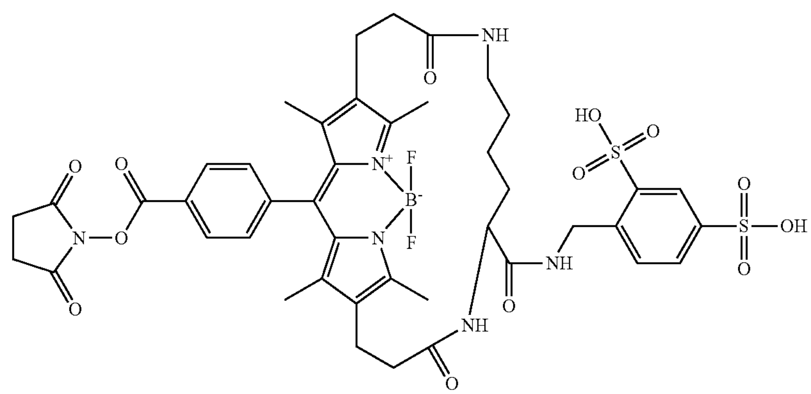 [SMILES: CC1=C2CCC(=O)NCCCCC(C(=O)NCc3ccc(S(=O)(=O)O)cc3S(=O)(=O)O)NC(=O)CCc3c(C)c4n(c3C)[B-](F)(F)[N+](=C2C)C1=C4c1ccc(C(=O)ON2C(=O)CCC2=O)cc1] |
| 126 | 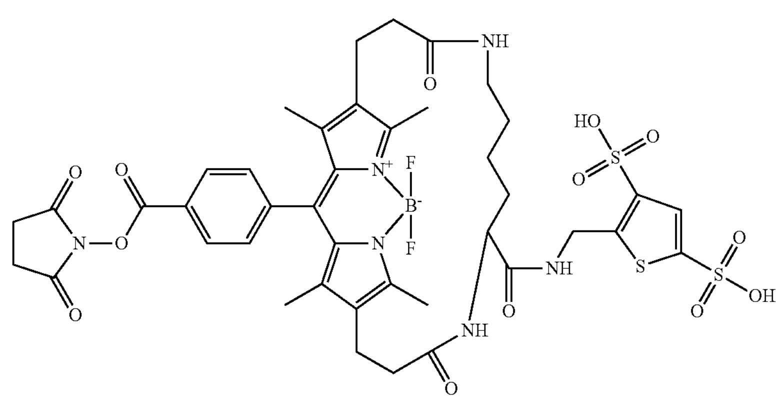 [SMILES: CC1=C2CCC(=O)NCCCCC(C(=O)NCc3sc(S(=O)(=O)O)cc3S(=O)(=O)O)NC(=O)CCc3c(C)c4n(c3C)[B-](F)(F)[N+](=C2C)C1=C4c1ccc(C(=O)ON2C(=O)CCC2=O)cc1] |

TABLE 2-continued
Example compounds of the invention
| Dye | Structure |
|---|---|
| 127 | 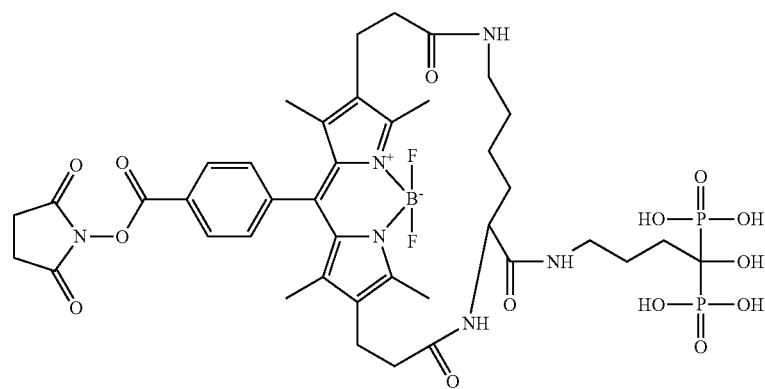 [SMILES: CC1=C2CCC(=O)NCCCCC(C(=O)NCCCC(O)(P(=O)(O)O)P(=O)(O)O)NC(=O)CCc3c(C)c4n(c3C)[B-](F)(F)[N+](=C2C)C1=C4c1ccc(C(=O)ON2C(=O)CCC2=O)cc1] |
| 128 | 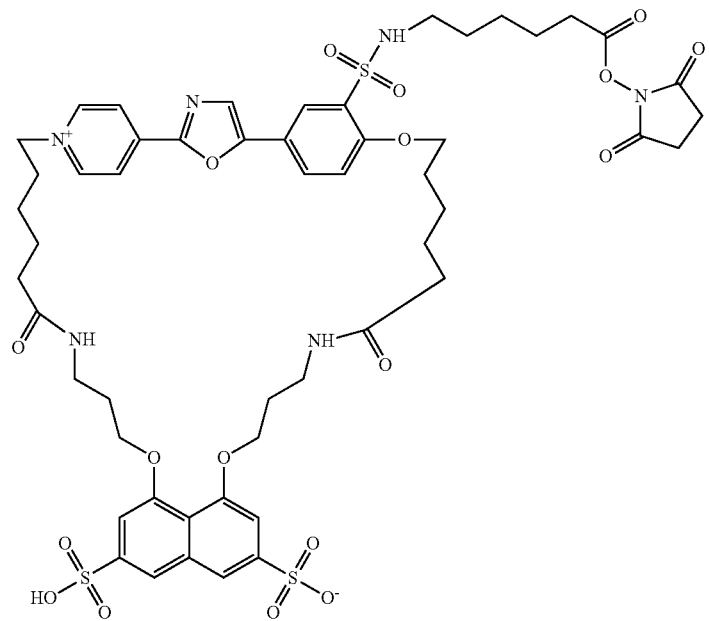 [SMILES: O=C1CCCCCOc2ccc(cc2S(=O)(=O)NCCCCCC(=O)ON2C(=O)CCC2=O)-c2cnc(o2)-c2cc[n+](cc2)CCCCCC(=O)NCCCOc2cc(S(=O)(=O)O)cc3cc(S(=O)(=O)[O-])cc(c23)OCCCN1] |

TABLE 2-continued
Example compounds of the invention
| Dye | Structure |
|---|---|
| 129 | 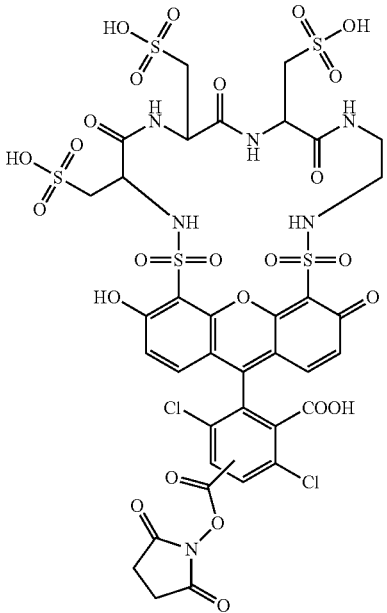 |
| 130 | 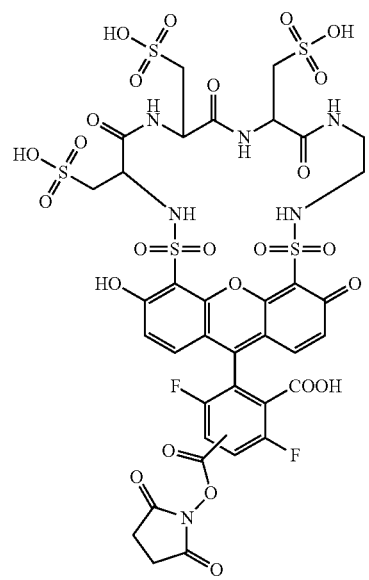 |

TABLE 2-continued
Example compounds of the invention
| Dye | Structure |
|---|---|
| 131 | 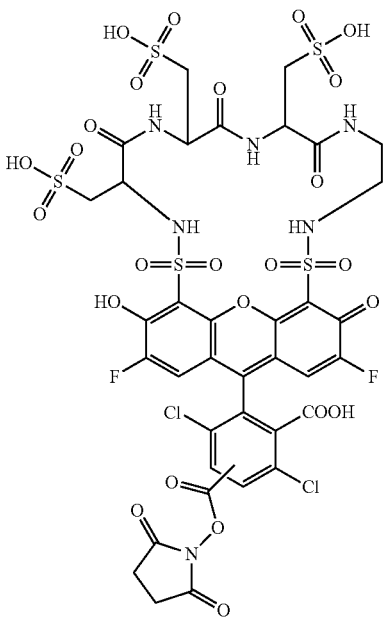 |
| 132 | 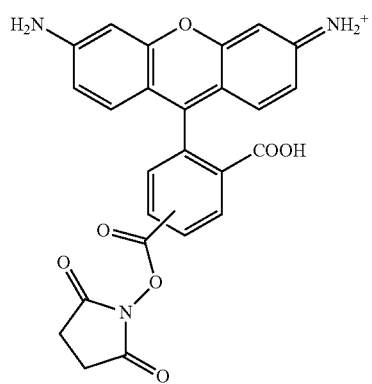 |

TABLE 2-continued
Example compounds of the invention
| Dye | Structure |
|---|---|
| 133 | 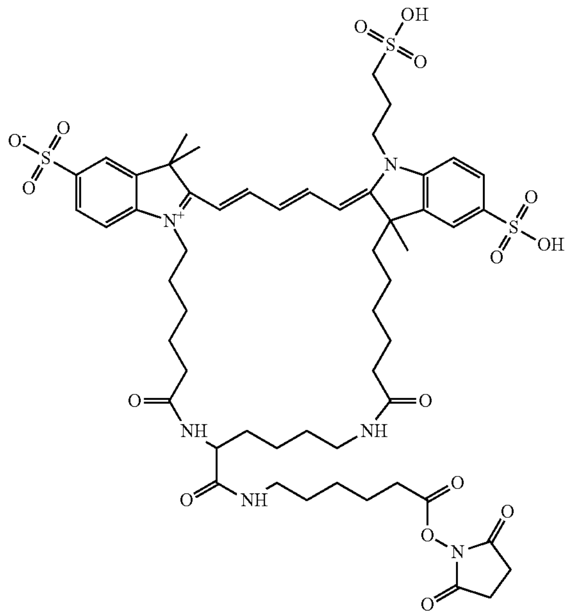 [SMILES: CC1(C)C2=[N+](CCCCCC(=O)NC(C(=O)NCCCCCC(=O)ON3C(=O)CCC3=O)CCCCNC(=O)CCCCCC3(C)/C(=C/C=C/C=C/2)N(CCCS(=O)(=O)O)c2ccc(S(=O)(=O)O)cc23)c2ccc(S(=O)(=O)[O-])cc21] |
| 134 | 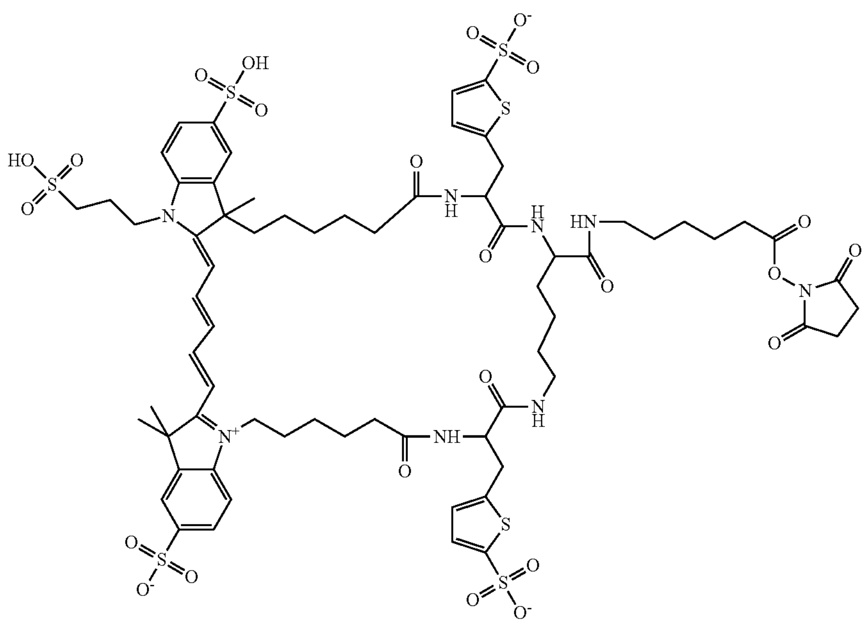 [SMILES: CC1(C)C2=[N+](CCCCCC(=O)NC(Cc3ccc(S(=O)(=O)[O-])s3)C(=O)NCCCCC(C(=O)NCCCCCC(=O)ON3C(=O)CCC3=O)NC(=O)C(Cc3ccc(S(=O)(=O)[O-])s3)NC(=O)CCCCCC3(C)/C(=C/C=C/C=C/2)N(CCCS(=O)(=O)O)c2ccc(S(=O)(=O)O)cc23)c2ccc(S(=O)(=O)[O-])cc21] |
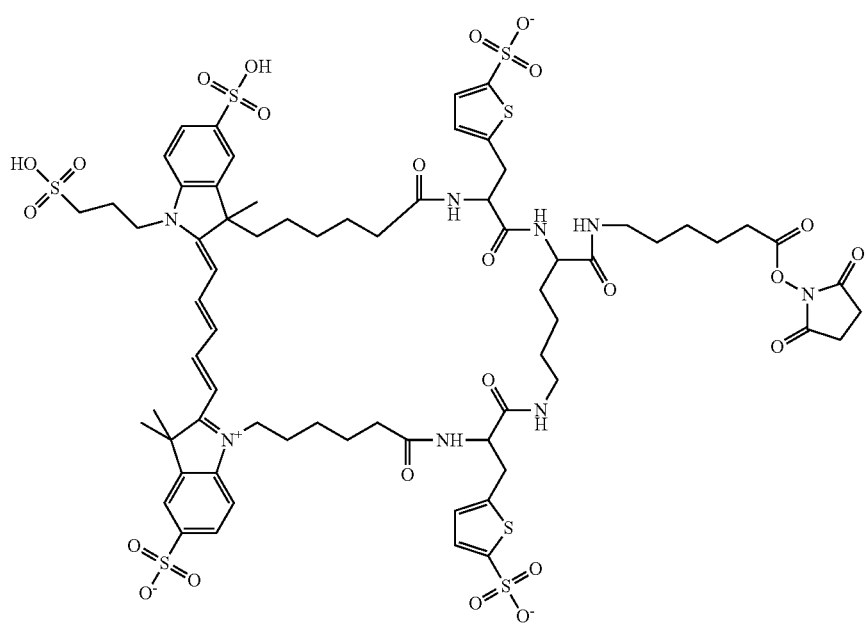

TABLE 2-continued

Example compounds of the invention

| Dye | Structure |
|---|---|
| 135 | 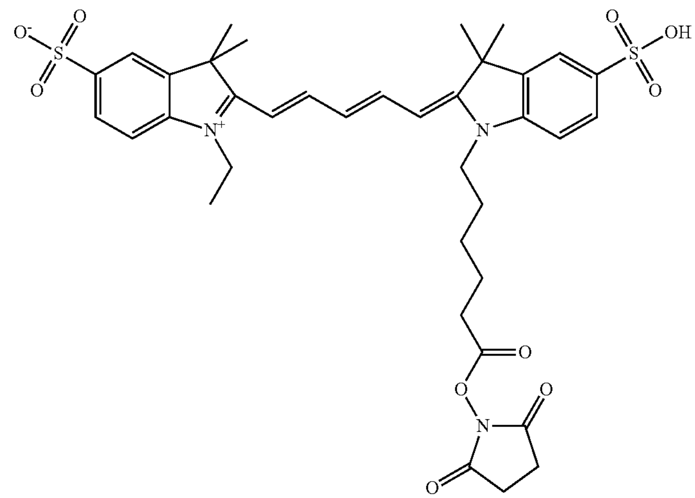 [SMILES: CC[N+]1=C(/C=C/C=C/C=C2/N(CCCCCC(=O)ON3C(=O)CCC3=O)c3ccc(S(=O)(=O)O)cc3C2(C)C)C(C)(C)c2cc(S(=O)(=O)[O-])ccc21] |
| 136 | 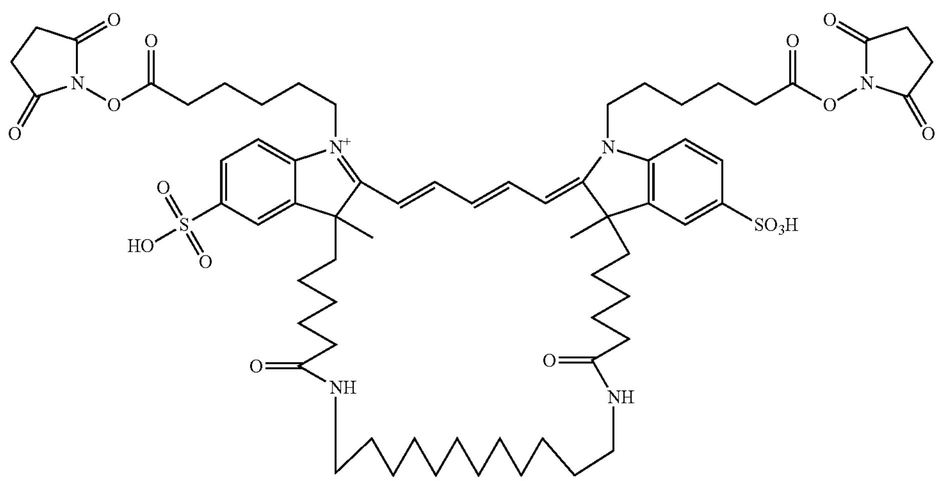 [SMILES: CC12CCCCCC(=O)NCCCCCCCCCCCCNC(=O)CCCCCC3(C)/C(=C/C=C/C=C/C1=[N+](CCCCCC(=O)ON1C(=O)CCC1=O)c1ccc(S(=O)(=O)O)cc12)N(CCCCCC(=O)ON1C(=O)CCC1=O)c1ccc(S(=O)(=O)O)cc13] |
| 137 | 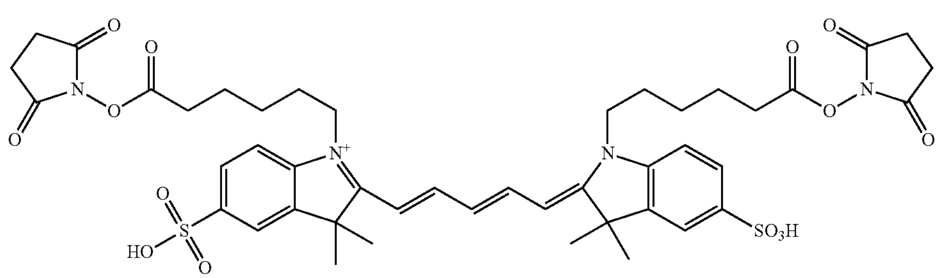 [SMILES: CC1(C)C(/C=C/C=C/C=C2\N(CCCCCC(=O)ON3C(=O)CCC3=O)c3ccc(S(=O)(=O)O)cc3C2(C)C)=[N+](CCCCCC(=O)ON2C(=O)CCC2=O)c2ccc(S(=O)(=O)O)cc21] |

Applications and Methods of Use

In one aspect of the invention, the dye compounds of the invention are used to directly stain or label a sample so that the sample can be identified or quantitated. For instance, such dyes may be added as part of an assay for a biological target analyte, as a detectable tracer element in a biological or non-biological fluid; or for such purposes as photodynamic therapy of tumors, in which a dyed sample is irradiated to selectively destroy tumor cells and tissues; or to photoablate arterial plaque or cells, usually through the photosensitized production of singlet oxygen. In one preferred embodiment, dye conjugate is used to stain a sample that comprises a ligand for which the conjugated substance is a complementary member of a specific binding pair (e.g. Table 3).

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids.

Alternatively, the sample is obtained from an environmental source such as soil, water, or air; or from an industrial source such as taken from a waste stream, a water source, a supply line, or a production lot.

TABLE 3

Representative specific binding pairs

| Antigen | Antibody |
| --- | --- |
| Biotin | Anti-biotin or avidin or streptavidin or neutravidin |
| IgG* | Protein A or protein G or anti-IgG antibody |
| Drug | Drug receptor |
| Toxin | Toxin receptor |
| Carbohydrate | Lectin or carbohydrate receptor |
| Peptide | Peptide receptor |
| Nucleotide | Complimentary nucleotide |
| Protein | Protein receptor |
| Enzyme substrate | Enzyme |
| DNA (RNA) | aDNA (aRNA)** |
| Hormone | Hormone receptor |
| Psoralen | Nucleic acid |
| Target molecule | RNA or DNA aptamer |
| Ion | Ion chelator |

*IgG is an immunoglobulin;
**aDNA and aRNA are the antisense (complementary) strands used for hybridization In yet another embodiment, the sample is present on or in solid or semi-solid matrix. In one aspect of the invention, the matrix is a membrane. In another aspect, the matrix is an electrophoretic gel, such as is used for separating and characterizing nucleic acids or proteins, or is a blot prepared by transfer from an electrophoretic gel to a membrane. In another aspect, the matrix is a silicon chip or glass slide, and the analyte of interest has been immobilized on the chip or slide in an array (e.g. the sample comprises proteins or nucleic acid polymers in a microarray). In yet another aspect, the matrix is a microwell plate or microfluidic chip, and the sample is analyzed by automated methods, typically by various methods of high-throughput screening, such as drug screening.

The dye compounds of the invention are generally utilized by combining a dye compound of the invention as described above with the sample of interest under conditions selected to yield a detectable optical response. The term "dye compound" is used herein to refer to all aspects of the claimed dyes, including both reactive dyes and dye conjugates. The dye compound typically forms a covalent or non-covalent association or complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard or expected response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic. Some dyes of the invention may exhibit little fluorescence emission, but are still useful as chromophoric dyes. Such chromophores are useful as energy acceptors in FRET applications, or to simply impart the desired color to a sample or portion of a sample.

For biological applications, the dye compounds of the invention are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar or higher. The optimal concentration is determined by systematic variation until satisfactory results with minimal background fluorescence are accomplished.

The dye compounds are most advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acids, nucleic acids or carbohydrate polymers, or lipid membrane complexes). These dyes are generally non-toxic to living cells and other biological components, within the concentrations of use.

The dye compound is combined with the sample in any way that facilitates contact between the dye compound and the sample components of interest. Typically, the dye compound or a solution containing the dye compound is simply added to the sample. Certain dyes of the invention, particularly those that are substituted by one or more sulfonic acid moieties, tend to be impermeant to membranes of biological cells, and once inside viable cells are typically well retained. Treatments that permeabilize the plasma membrane, such as electroporation, shock treatments or high extracellular ATP can be used to introduce selected dye compounds into cells. Alternatively, selected dye compounds can be physically inserted into cells, e.g. by pressure microinjection, scrape loading, patch clamp methods, or phagocytosis.

Dyes that incorporate an aliphatic amine or a hydrazine residue can be microinjected into cells, where they can be fixed in place by aldehyde fixatives such as formaldehyde or glutaraldehyde. This fixability makes such dyes useful for intracellular applications such as neuronal tracing.

Dye compounds that possess a lipophilic substituent, such as phospholipids, will noncovalently incorporate into lipid assemblies, e.g. for use as probes for membrane structure; or for incorporation in liposomes, lipoproteins, films, plastics, lipophilic microspheres or similar materials; or for tracing. Lipophilic dyes are useful as fluorescent probes of membrane structure.

Chemically reactive dye compounds will covalently attach to a corresponding functional group on a wide variety of materials, forming dye conjugates as described above. Using dye compounds to label reactive sites on the surface of cells, in cell membranes or in intracellular compartments such as organelles, or in the cell's cytoplasm, permits the determination of their presence or quantity, accessibility, or their spatial and temporal distribution in the sample. Photoreactive dyes can be used similarly to photolabel components of the outer membrane of biological cells or as photo-fixable polar tracers for cells.

Optionally, the sample is washed after staining to remove residual, excess or unbound dye compound. The sample is optionally combined with one or more other solutions in the course of staining, including wash solutions, permeabilization and/or fixation solutions, and solutions containing additional detection reagents. An additional detection reagent typically produces a detectable response due to the presence of a specific cell component, intracellular substance, or cellular condition, according to methods generally known in the art. Where the additional detection reagent has, or yields a product with, spectral properties that differ from those of the subject dye compounds, multi-color applications are possible. This is particularly useful where the additional detection reagent is a dye or dye-conjugate of the present invention having spectral properties that are detectably distinct from those of the staining dye.

The dye conjugates of the invention are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. No. 5,332,666 to Prober, et al. (1994); U.S. Pat. No. 5,171,534 to Smith, et al. (1992); U.S. Pat. No. 4,997,928 to Hobbs (1991); and WO Appl. 94/05688 to Menchen, et al.). Dye-conjugates of multiple independent dyes of the invention possess utility for multi-color applications.

At any time after or during staining, the sample is illuminated with a wavelength of light selected to give a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred embodiments of the invention are dyes that are be excitable at or near the wavelengths 405 nm, 488 nm, 546 nm, 594 nm, 633-636 nm, 647 nm, 660 nm, 680 nm and beyond 700 nm, as these regions closely match the output of relatively inexpensive excitation sources.

The optical response is optionally detected by visual inspection, or by use of any of the following devices: CCD cameras, video cameras, photographic films, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

One aspect of the instant invention is the formulation of kits that facilitate the practice of various assays using any of the dyes of the invention, as described above. The kits of the invention typically comprise a colored or luminescent dye of the invention, either present as a chemically reactive label useful for preparing dye-conjugates, or present as a dye-conjugate where the conjugated substance is a specific binding pair member, or a nucleoside, a nucleotide, an oligonucleotide, a nucleic acid polymer, a peptide, or a protein. The kits optionally further comprise one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

EXAMPLES

Examples of synthetic strategies, conjugates and method of use for selected dyes of the invention are provided in the examples below. Further modifications and permutations will be obvious to one skilled in the art. The examples below are given so as to illustrate the practice of this invention. They are not intended to limit or define the entire scope of this invention.

Example 1

Preparation of Compound 1

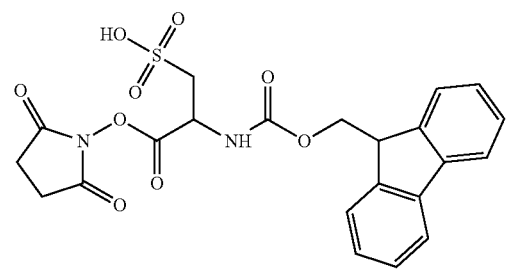 [SMILES: O=C(NC(CS(=O)(=O)O)C(=O)ON1C(=O)CCC1=O)OCC1c2ccccc2-c2ccccc21]

To a solution of FMOC-cysteic acid triethylamine salt (6 g in 25 mL DMSO) is added O—(N-succinimidyl)-N,N,N',N'-tetramethyluronium tetrafluoroborate (4 g), followed by the addition of triethylamine (1.4 mL). The mixture is stirred at room temperature for 1 h. The solution is poured into EtOAc (250 mL). The solid is centrifuged and washed with EtOAc (5×50 mL), ether (3×50 mL) and dried under vacuum to give Compound 1.

Example 2

Preparation of Compound 2

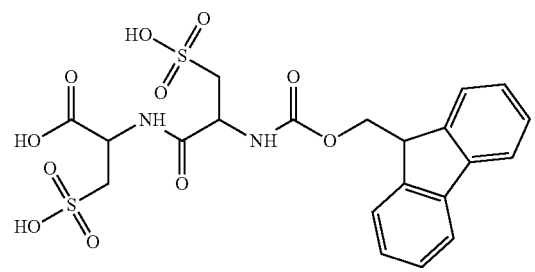 [SMILES: O=C(NC(CS(=O)(=O)O)C(=O)NC(CS(=O)(=O)O)C(=O)O)OCC1c2ccccc2-c2ccccc21]

To a solution of Compound 1 (6 g in 15 mL DMSO) is added cysteic acid triethylamine salt (3 g in 10 mL DMSO) at room temperature. The mixture is stirred at room temperature for 12 h. The solution is poured into EtOAc (250 mL). The solid is centrifuged and washed with EtOAc (5×50 mL), ether (3×50 mL) and dried under vacuum to give crude Compound 2. The crude solid is further purified by preparative HPLC to yield the pure Compound 2 using 0.1% TFA in water-0.1% TFA in MeCN buffer system.

Example 3

Preparation of Compound 3

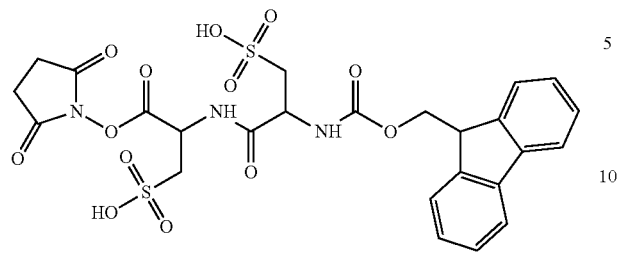

Compound 3 is analogously prepared from the reaction of Compound 2 with O—(N-succinimidyl)-N,N,N',N'-tetramethyluronium tetrafluoroborate according to the procedure of Compound 1.

Example 4

Preparation of Compound 4

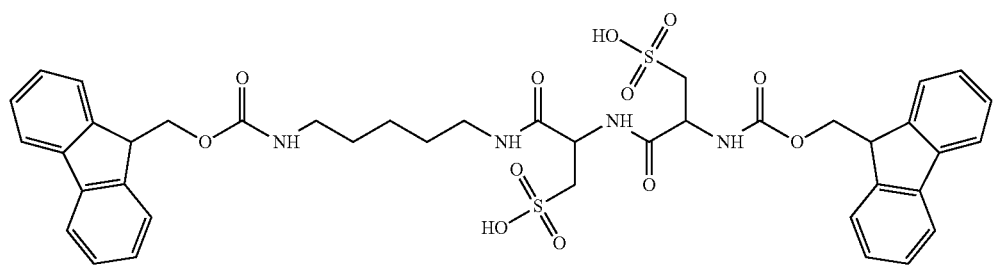 [SMILES: O=C(NCCCCCNC(=O)C(CS(=O)(=O)O)NC(=O)C(CS(=O)(=O)O)NC(=O)OCC1c2ccccc2-c2ccccc21)OCC1c2ccccc2-c2ccccc21]

To a solution of Compound 3 (3 g in 15 mL DMF) is added FMOC cadaverine HCl salt (5 g in 15 mL DMF) at room temperature, followed by the addition of triethylamine (1.5 mL). The mixture is stirred at room temperature for 12 h. The solution is poured into EtOAc (250 mL). The solid is centrifuged and washed with EtOAc (5×50 mL), ether (3×50 mL) and dried under vacuum to give crude Compound 4. The crude solid is further purified by preparative HPLC to yield the pure Compound using 0.1% TFA in water-0.1% TFA in MeCN buffer system.

Example 5

Preparation of Compound 5

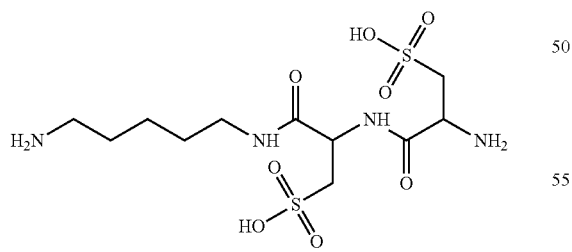

To a solution of Compound 4 (1 g in 15 mL DMF) is added piperidine (1.2 mL) at room temperature. The mixture is stirred at room temperature for 6 h. The solution is poured into EtOAc (250 mL). The solid is centrifuged and washed with EtOAc (5×50 mL), ether (3×50 mL) and dried under vacuum to give crude Compound 5. The crude solid is dissolved in 5% HCl, and further purified on a Sephadex LH-20 column to give the pure product using 0.1% HCl as the eluting system.

Example 6

Preparation of Compound 6

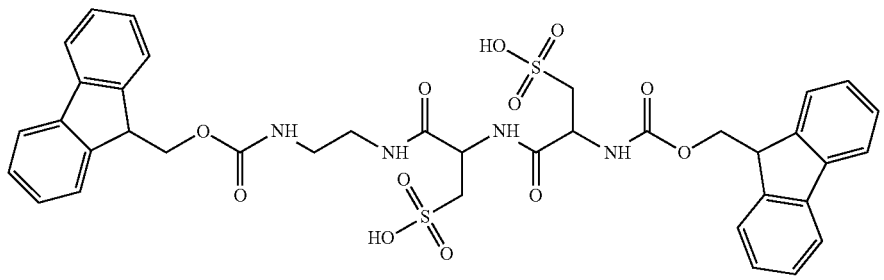 [SMILES: O=C(NCCNC(=O)C(CS(=O)(=O)O)NC(=O)C(CS(=O)(=O)O)NC(=O)OCC1c2ccccc2-c2ccccc21)OCC1c2ccccc2-c2ccccc21]

Compound 6 is analogously prepared from the reaction of Compound 3 with FMOC ethylenediamine according to the procedure of Compound 4.

Example 7

Preparation of Compound 7

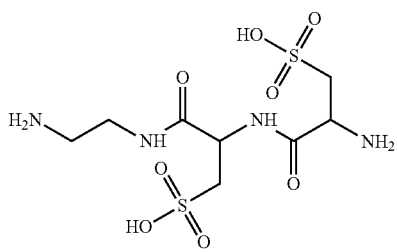 [SMILES: NCCNC(=O)C(CS(=O)(=O)O)NC(=O)C(N)CS(=O)(=O)O]

Compound 7 is analogously prepared from the deprotection of Compound 6 with piperidine according to the procedure of Compound 5.

Example 8

Preparation of Compound 8

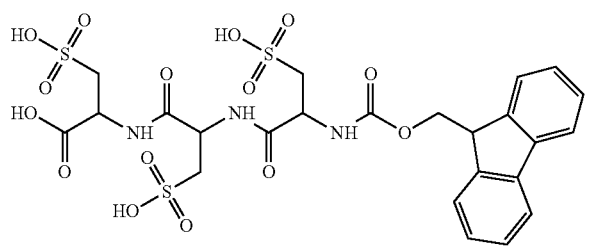 [SMILES: O=C(NC(CS(=O)(=O)O)C(=O)NC(CS(=O)(=O)O)C(=O)NC(CS(=O)(=O)O)C(=O)O)OCC1c2ccccc2-c2ccccc21]

Compound 8 is analogously prepared from the reaction of Compound 3 with cysteic acid according to the procedure of Compound 2.

Example 9

Preparation of Compound 9

Compound 9 is analogously prepared from the reaction of Compound 8 of with O—(N-succinimidyl)-N,N,N',N'-tetramethyluronium tetrafluoroborate according to the procedure of Compound 1.

Example 10

Preparation of Compound 10

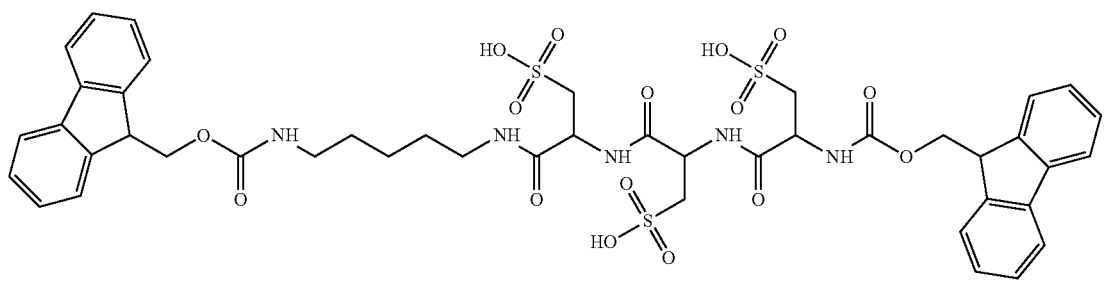 [SMILES: O=C(NCCCCCNC(=O)C(CS(=O)(=O)O)NC(=O)C(CS(=O)(=O)O)NC(=O)C(CS(=O)(=O)O)NC(=O)OCC1c2ccccc2-c2ccccc21)OCC1c2ccccc2-c2ccccc21]

Compound 10 is analogously prepared from the reaction of Compound 9 with FMOC cadaverine according to the procedure of Compound 4.

Example 11

Preparation of Compound 11

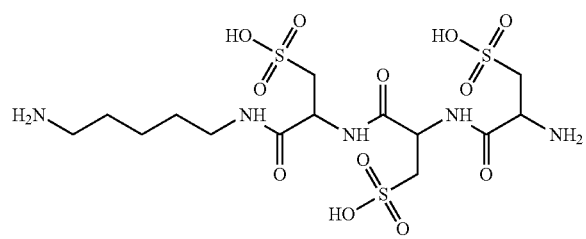 [SMILES: NCCCCCNC(=O)C(CS(=O)(=O)O)NC(=O)C(CS(=O)(=O)O)NC(=O)C(N)CS(=O)(=O)O]

Compound 11 is analogously prepared from the deprotection of Compound 10 with piperidine according to the procedure of Compound 5.

Example 12

Preparation of Compound 12

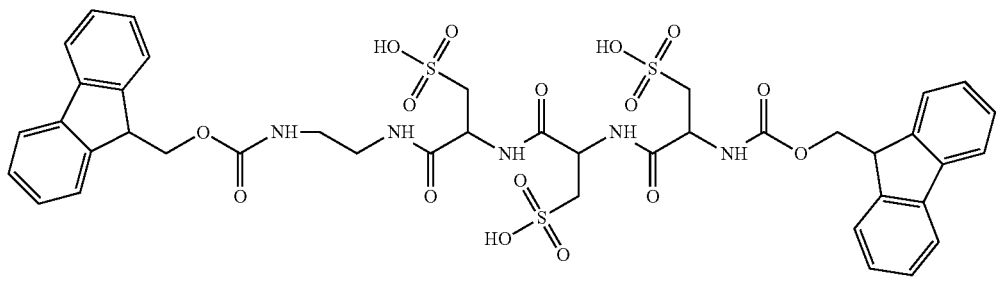 [SMILES: O=C(NCCNC(=O)C(CS(=O)(=O)O)NC(=O)C(CS(=O)(=O)O)NC(=O)C(CS(=O)(=O)O)NC(=O)OCC1c2ccccc2-c2ccccc21)OCC1c2ccccc2-c2ccccc21]

Compound 12 is analogously prepared from the reaction of Compound 9 with FMOC ethylenediamine according to the procedure of Compound 4.

Example 13

Preparation of Compound 13

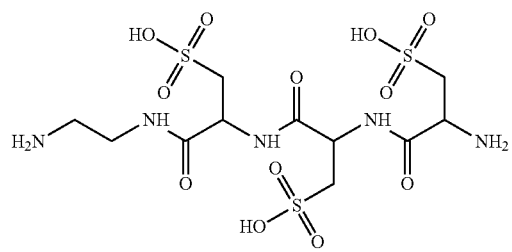 [SMILES: NCCNC(=O)C(CS(=O)(=O)O)NC(=O)C(CS(=O)(=O)O)NC(=O)C(N)CS(=O)(=O)O]

Compound 13 is analogously prepared from the deprotection of Compound 9 with piperidine according to the procedure of Compound 5.

Example 14

Preparation of Compound 14

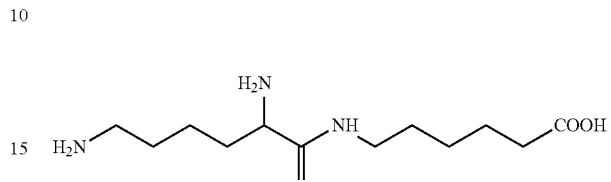

The mixture of Boc-Lys(Boc)-OH (10 g), N-hydroxysuccinimide (4 g) and DCC (7 g) in DMF (100 mL) is stirred at room temperature overnight. After removal of solid (DCU), the filtrate [Boc-Lys(Boc)-OSu] is added to a solution of 6-aminocaprioic acid (4 g) in water (50 mL), followed by addition of 5M $Na_2CO_3$ to adjust pH to 8-9. The mixture is stirred at room temperature overnight. After diluted with water (500 mL), the mixture is acidified with 5% aqueous HCl to pH 3 and extracted with ethyl acetate (5×250 mL). The combined extract is washed with brine and dried over $Na_2SO_4$. After removal of solvent, the residue [Boc-Lys(Boc)-NH(CH$_2$)$_5$COOH] is dissolved in 1,4-dioxane (1000 mL), followed by addition of 4M HCl in dioxane (1000 mL). The mixture is stirred for 6 hour. The solvent is decanted and the solid is washed with ethyl acetate (5×250 mL) and ether (3×200 mL). The HCl salt of Compound 14 is dried under vacuum.

Example 15

Preparation of Compound 15

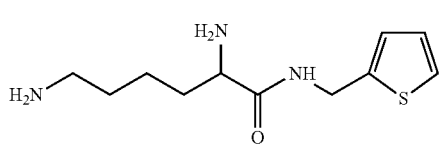 [SMILES: NCCCCC(N)C(=O)NCc1cccs1]

Compound 15 is analogously prepared from the reaction of Boc-Lys(Boc)-OH with 2-aminomethyl thiophene according to the procedure of Compound 14.

Example 16

Preparation of Compound 16

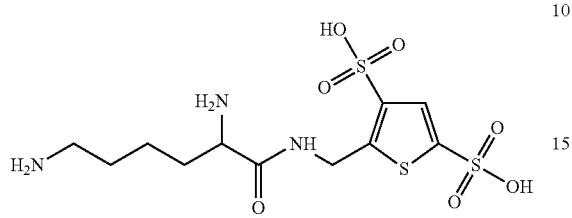

Compound 15 (1 g) is suspended in concentrated $H_2SO_4$ (5 mL). To the suspension is added 20% fuming $H_2SO_4$ (5 mL). The reaction mixture is stirred at 0° C. until the reaction is complete as indicated by TLC. To cold ether (200 ml) the reaction mixture is dropwise added with vigorous stirring to give the crude Compound 16. The crude material is further purified by preparative HPLC to yield the pure Compound 16 using 0.1% TFA in water-0.1% TFA in MeCN buffer system.

Example 17

Preparation of Compound 17

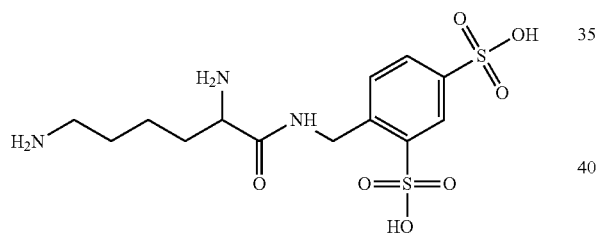

Compound 17 is analogously prepared from the reaction of Boc-Lys(Boc)-OH with 2',4'-disulfobenzylamine according to the procedure of Compound 14.

Example 18

Preparation of Compound 18

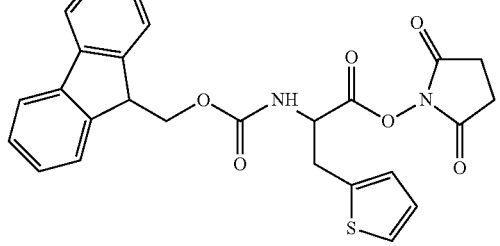

The mixture of beta-(2-thienyl)-FMOC-L-alanine (10 g), N-hydroxysuccinimide (10 g) and DCC (15 g) in DMF (100 mL) is stirred at room temperature overnight. The reaction mixture is filtered to remove the insoluble solid. To the filtrate is added water (250 mL), and the solid is collected by filtration. The solid is washed with water, and dried under high vacuum. The crude solid is directly used for the next step reaction without further purification.

Example 19

Preparation of Compound 19

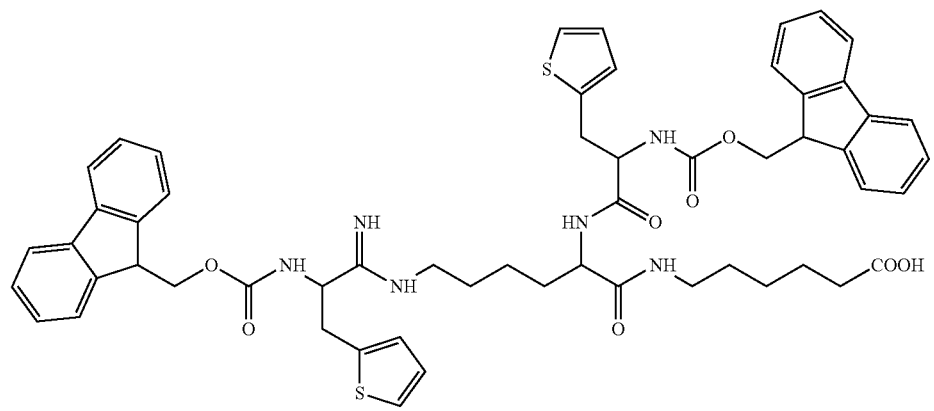 [SMILES: N=C(NCCCCC(NC(=O)C(Cc1cccs1)NC(=O)OCC1c2ccccc2-c2ccccc21)C(=O)NCCCCCC(=O)O)C(Cc1cccs1)NC(=O)OCC1c2ccccc2-c2ccccc21]

The mixture of Compounds 14 (5 g) and 18 (2 g) are dissolved in DMF (50 mL). To the solution is added triethylamine (3 mL), and is stirred at room temperature overnight. The reaction mixture is dropwise added to water (250 mL), and filtered to collect the precipitate. The solid is washed with water, and dried under high vacuum. The crude material is further purified by a silica gel column to yield the pure Compound 19 using a gradient of chloroform/methanol.

Example 20

Preparation of Compound 20

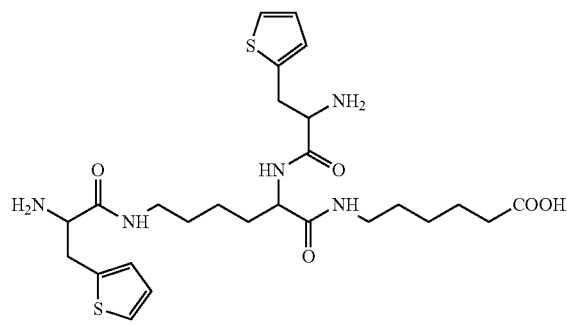 [SMILES: NC(Cc1cccs1)C(=O)NCCCCC(NC(=O)C(N)Cc1cccs1)C(=O)NCCCCCC(=O)O]

To a solution of Compound 19 (2 g in 20 mL DMF) is added piperidine (1.2 mL) at room temperature. The mixture is stirred at room temperature for 6 h. The solution is poured into EtOAc (150 mL). The solid is centrifuged and washed with EtOAc (5×50 mL), ether (3×50 mL) and dried under vacuum to give Compound 20.

Example 21

Preparation of Compound 21

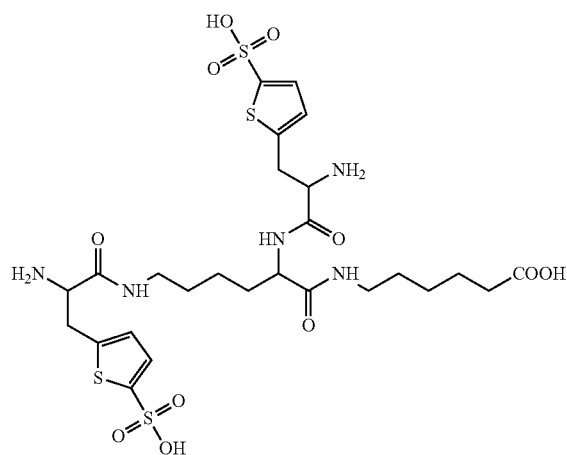 [SMILES: NC(Cc1ccc(S(=O)(=O)O)s1)C(=O)NCCCCC(NC(=O)C(N)Cc1ccc(S(=O)(=O)O)s1)C(=O)NCCCCCC(=O)O]

Compound 21 is analogously prepared from the sulfonation of Compound 20 using fuming sulfuric acid according to the procedure of Compound 16.

Example 22

Preparation of Compound 22

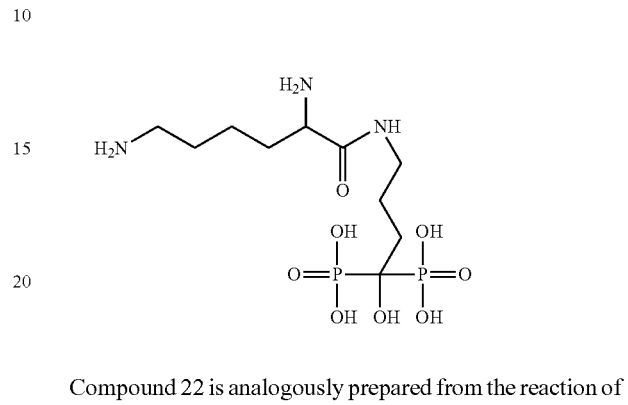

Compound 22 is analogously prepared from the reaction of Boc-Lys(Boc)-OH with 4-amino-1-hydroxy-1-phosphonobutyl phosphonic acid sodium salt according to the procedure of Compound 14.

Example 23

Preparation of Compound 23

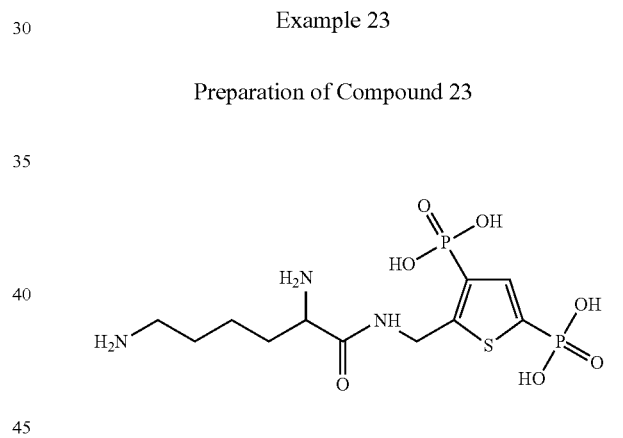

Compound 23 is analogously prepared from the reaction of Boc-Lys(Boc)-OH with 2-(2',4'-diphosphonylthienyl)methylamine according to the procedure of Compound 14.

Example 24

Preparation of Compound 24

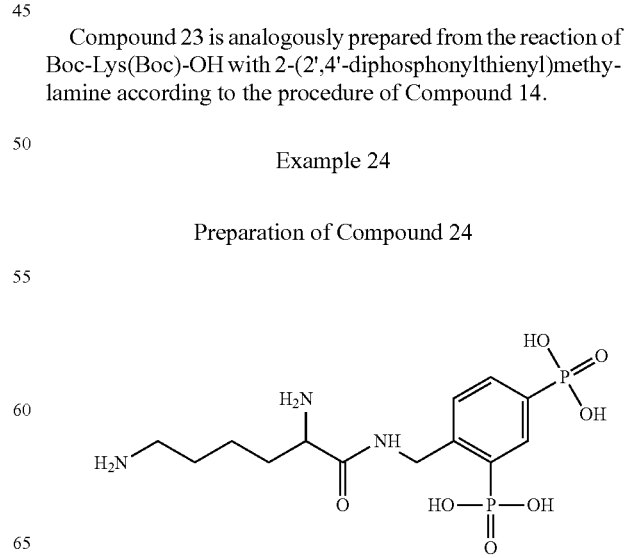

Compound 24 is analogously prepared from the reaction of Boc-Lys(Boc)-OH with 1-aminomethyl-2,4-diphosphonyl-benzene according to the procedure of Compound 14.

Example 25

Preparation of Compound 25

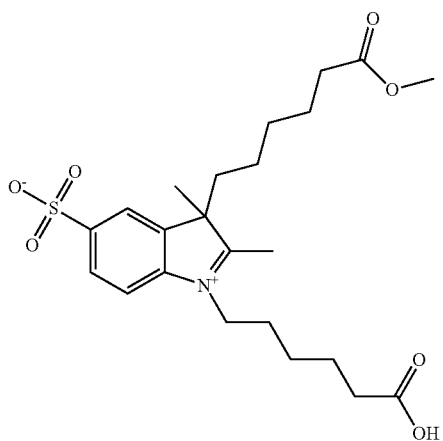 [SMILES: COC(=O)CCCCCC1(C)C(C)=[N+](CCCCCC(=O)O)c2ccc(S(=O)(=O)[O-])cc21]

Compound 25 is prepared as described in U.S. Pat. No. 7,465,810 (2008).

Example 26

Preparation of Compound 26

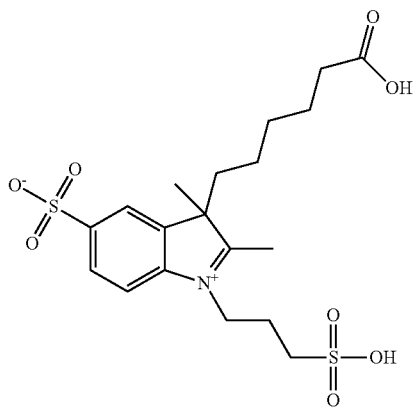 [SMILES: CC1=[N+](CCCS(=O)(=O)O)c2ccc(S(=O)(=O)[O-])cc2C1(C)CCCCCC(=O)O]

Compound 26 is prepared as described in U.S. Pat. No. 7,465,810 (2008).

Example 27

Preparation of Compound 27

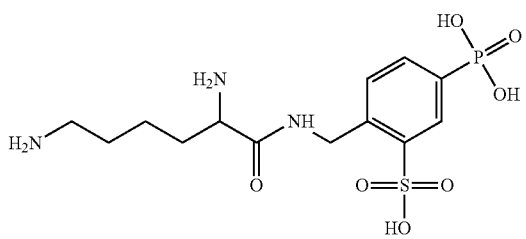 [SMILES: NCCCCC(N)C(=O)NCc1ccc(P(=O)(O)O)cc1S(=O)(=O)O]

Compound 27 is analogously prepared from the reaction of Boc-Lys(Boc)-OH with 1-aminomethyl-2-sulfonyl-4-phosphonylbenzene according to the procedure of Compound 14.

Example 28

Preparation of Compound 28

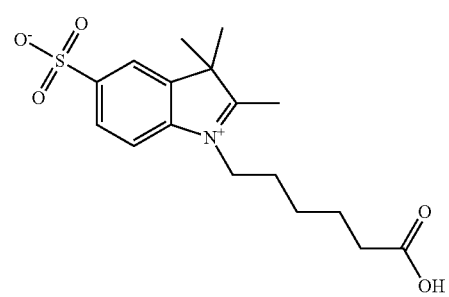 [SMILES: CC1=[N+](CCCCCC(=O)O)c2ccc(S(=O)(=O)[O-])cc2C1(C)C]

Compound 28 is prepared as described in U.S. Pat. No. 5,627,027 (1997).

Example 29

Preparation of Compound 29

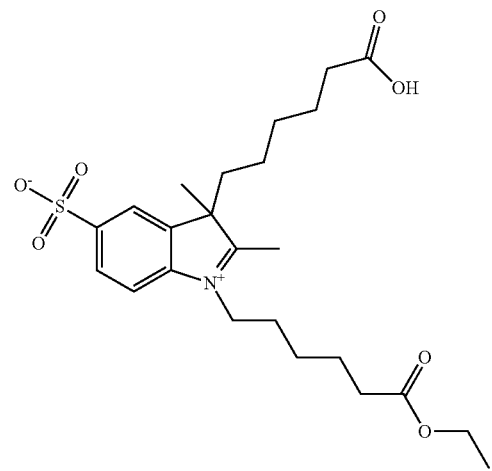 [SMILES: CCOC(=O)CCCCC[N+]1=C(C)C(C)(CCCCCC(=O)O)c2cc(S(=O)(=O)[O-])ccc21]

Compound 29 is prepared as described in U.S. Pat. No. 7,465,810 (2008).

Example 30

Preparation of Compound 30

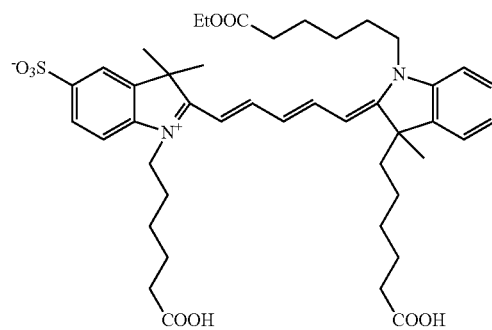

A solution of Compound 28 (1 g) and malonaldehyde bis(phenyl)mine) monohydrochloride (0.8 g) in acetic acid (5 mL) and acetic anhydride (5 mL) is heated at 120° C. for 2 hour. The completion of the reaction is monitored by absorption spectra in methanol. The solution of anyl intermediate is mixed with Compound 29 (1.5 g), then more acetic anhydride (5 mL) and pyridine (10 mL) are added. The reaction mixture is heated for 30 min until the anyl intermediate disappears (monitored by absorption spectra). The reaction mixture is cooled and poured into ethyl acetate (50 mL). The crude product is collected by centrifugation and washed with ethyl acetate twice, and further purified by preparative HPLC to yield the pure Compound 30 using 0.1% TFA in water-0.1% TFA in MeCN buffer system.

Example 31

Preparation of Compound 31

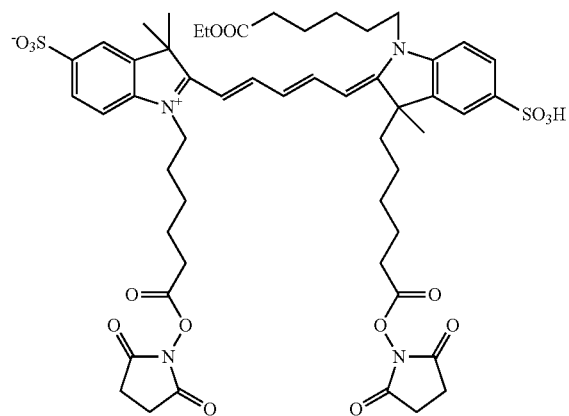

To a solution of Compound 30 (300 mg) and O—(N-succinimidyl)-N,N,N',N'-tetramethyluronium tetrafluoroborate (300 mg) in DMF (10 mL) is added triethylamine (0.4 mL). The mixture is stirred at room temperature for 2 h. The reaction mixture is poured into EtOAc (150 mL). The disuccinimidyl ester is collected by centrifugation and washed with EtOAc (5×50 mL), EtOEt (5×50 mL) and dried under vacuum.

Example 32

Preparation of Compound 32

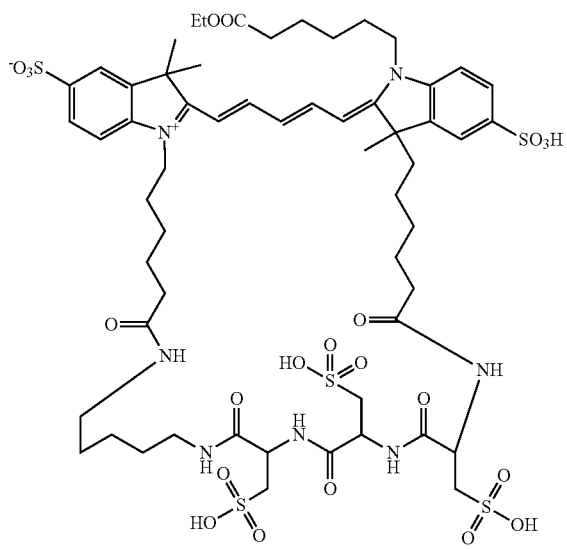

The crude Compound 31 (100 mg) is dissolved in DMF (150 mL) and a solution of Compound 11 (100 mg) in water (25 mL) [neutralized with $Na_2CO_3$ to pH 8.0] is added slowly during the period of 2 h. The mixture is stirred at room temperature overnight. After removal of solvent, the residue is purified by preparative HPLC to yield the pure Compound 32 using 0.1% TFA in water-0.1% TFA in MeCN buffer system.

Example 33

Preparation of Compound 33

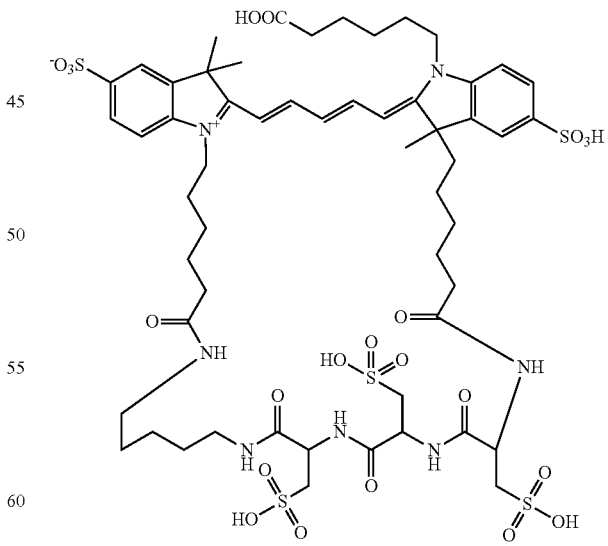

Compound 32 (50 mg) is dissolved in methanol (2 mL). To the solution is added 0.1M NaOH (0.5 mL) at room temperature. The mixture is stirred at room temperature for 3-6 hours and neutralized with 1M HCl to pH 6.0. After removal of solvent, the residue is purified by preparative HPLC to yield the pure Compound 33 using 0.1% TFA in water-0.1% TFA in MeCN buffer system.

Example 34

Preparation of Compound 34

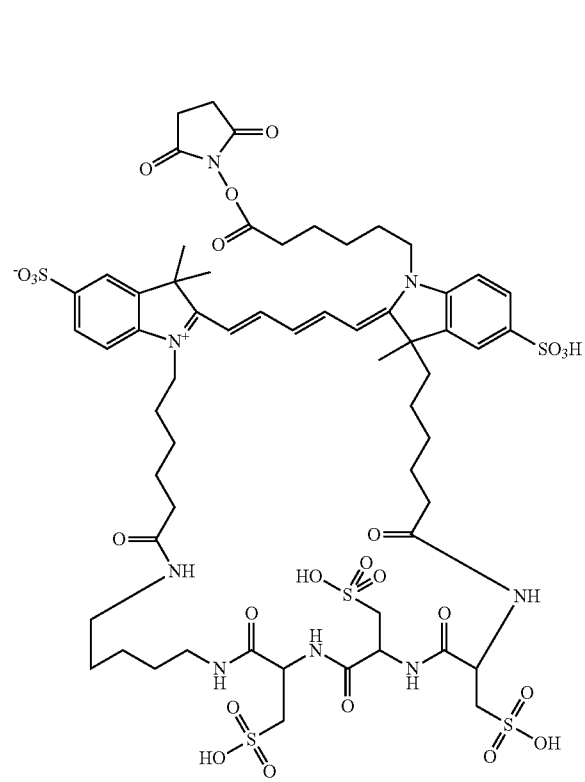

To a solution of Compound 33 (10 mg) in DMF (0.4 mL) is added O—(N-succinimidyl)-N,N,N',N'-tetramethyluronium tetrafluoroborate (4 mg), followed by triethylamine (0.03 mL). The mixture is stirred at room temperature for 1 h. The solution is poured into EtOAc (15 mL). The solid is centrifuged and washed with EtOAc (3×10 mL), ether (3×10 mL) and dried under vacuum to give Compound 34.

Example 35

Preparation of Compound 35

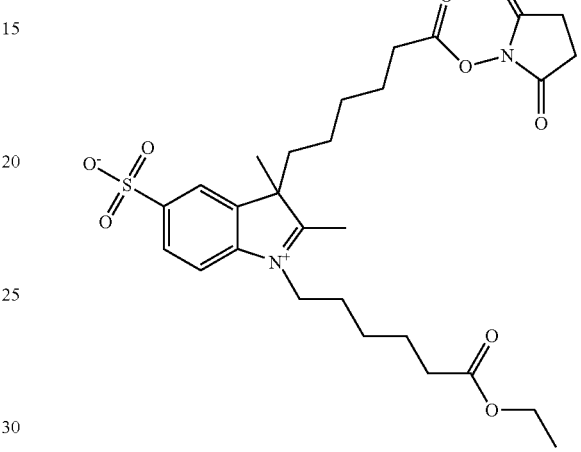

To the solution of Compound 29 ethyl ester (5 g) in DMF (20 mL) is added di(N-succinimidyl) carbonate (4 g), followed by triethylamine (4 mL). The mixture is stirred at room temperature for 1 h. The solution is poured into EtOAc (150 mL). The solid is centrifuged and washed with EtOAc (5×100 mL), ether (3×100 mL) and dried under vacuum to give Compound 35.

Example 36

Preparation of Compound 36

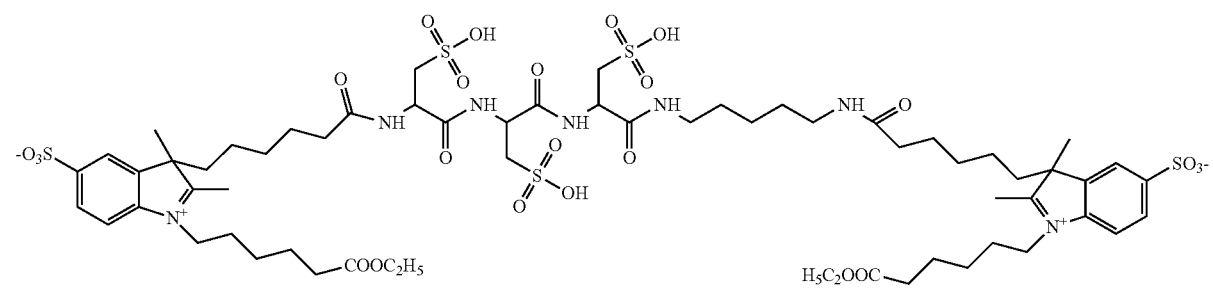

The mixture of Compounds 11 (100 mg) and 35 (500 mg) are dissolved in DMF (50 mL). To the solution is added triethylamine (3 mL), and is stirred at room temperature overnight. The reaction mixture is dropwise added to EtOAc (250 mL), and filtered to collect the precipitate. The solid is washed with EtOAc, and dried under high vacuum. The crude material is further purified by preparative HPLC to yield the pure Compound 36 using 0.1% TFA in water-0.1% TFA in MeCN buffer system.

Example 37

Preparation of Compound 37

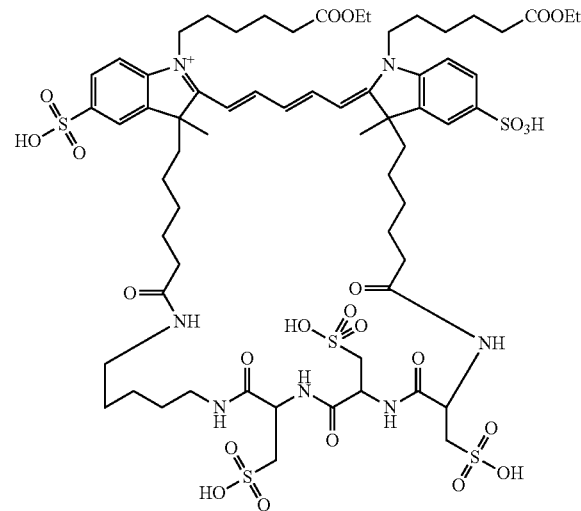 [SMILES: CCOC(=O)CCCCCN1\C2=C/C=C/C=C/C3=[N+](CCCCCC(=O)OCC)c4ccc(S(=O)(=O)O)cc4C3(C)CCCCCC(=O)NCCCCCNC(=O)C(CS(=O)(=O)O)NC(=O)C(CS(=O)(=O)O)NC(=O)C(CS(=O)(=O)O)NC(=O)CCCCCC2(C)c2cc(S(=O)(=O)O)ccc21]

Compound 36 (500 mg) and malonaldehyde bis(phenylmine) monohydrochloride (300 mg) are dissolved in acetic anhydride (1 mL), followed by addition of pyridine (1 mL). The mixture is heated to 120° C. for 1 h. After cooling to room temperature, the mixture is dropped into ethyl acetate. The crude dye is collected by centrifugation and washed with ethyl acetate twice. The crude material is further purified by preparative HPLC to yield the pure Compound 37 using 0.1% TFA in water-0.1% TFA in MeCN buffer system.

Example 38

Preparation of Compound 38

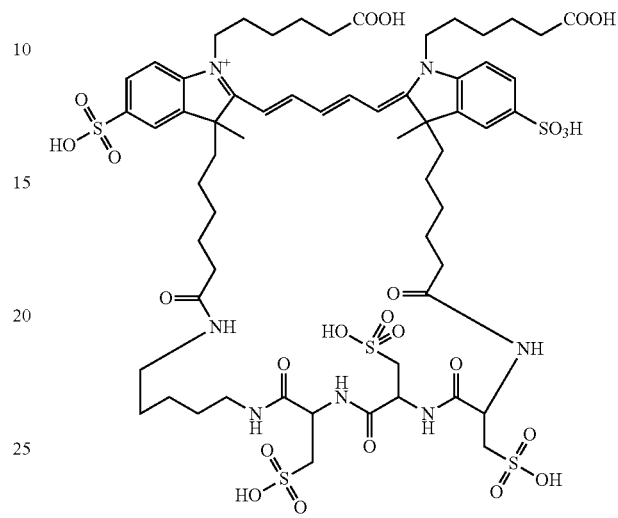

Compound 37 (20 mg) is dissolved in methanol (1 mL). To the solution is added 0.1M NaOH (0.5 mL) is slowly added at room temperature. The mixture is neutralized with 1M HCl to pH 6.0. After removal of solvent, the residue is purified by preparative HPLC to yield the pure Compound 38 using 0.1% TFA in water-0.1% TFA in MeCN buffer system.

Example 39

Preparation of Compound 39

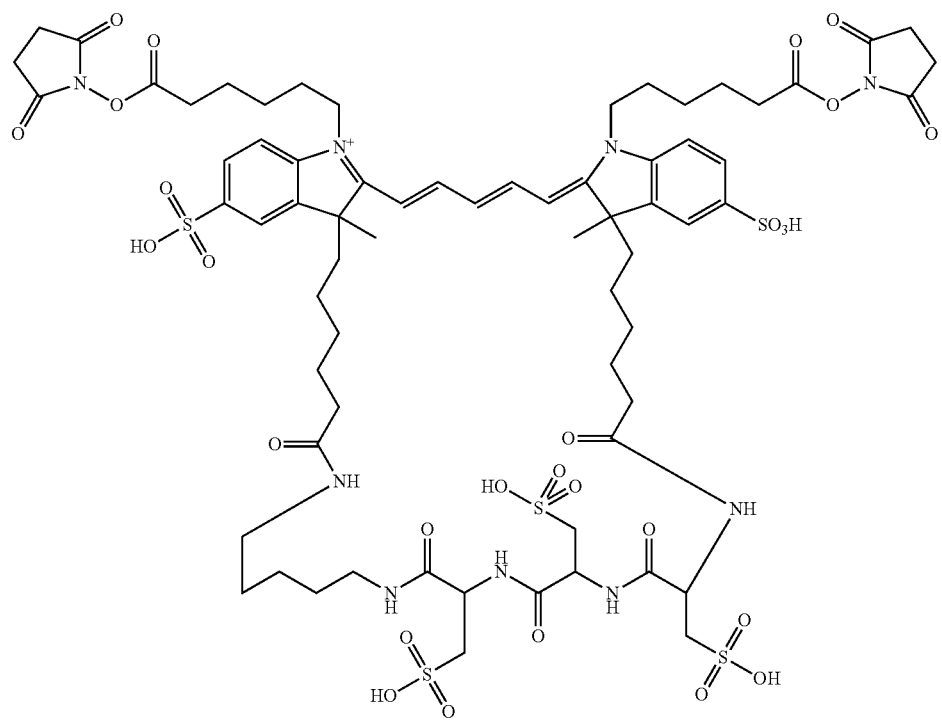 [SMILES: CC12CCCCCC(=O)NCCCCCNC(=O)C(CS(=O)(=O)O)NC(=O)C(CS(=O)(=O)O)NC(=O)C(CS(=O)(=O)O)NC(=O)CCCCCC3(C)/C(=C/C=C/C=C/C1=[N+](CCCCCC(=O)ON1C(=O)CCC1=O)c1ccc(S(=O)(=O)O)cc12)N(CCCCCC(=O)ON1C(=O)CCC1=O)c1ccc(S(=O)(=O)O)cc13]

To a solution of Compound 38 (10 mg) in DMF (0.4 mL) is added O—(N-succinimidyl)-N,N,N',N'-tetramethyluronium tetrafluoroborate (10 mg), followed by triethylamine (0.1 mL). The mixture is stirred at room temperature for 1 h. The solution mixture is poured into EtOAc (15 mL). The solid is centrifuged and washed with EtOAc (3×10 mL), ether (3×10 mL) and dried under vacuum to give Compound 39 as bright blue powder.

Example 40

Preparation of Compound 40

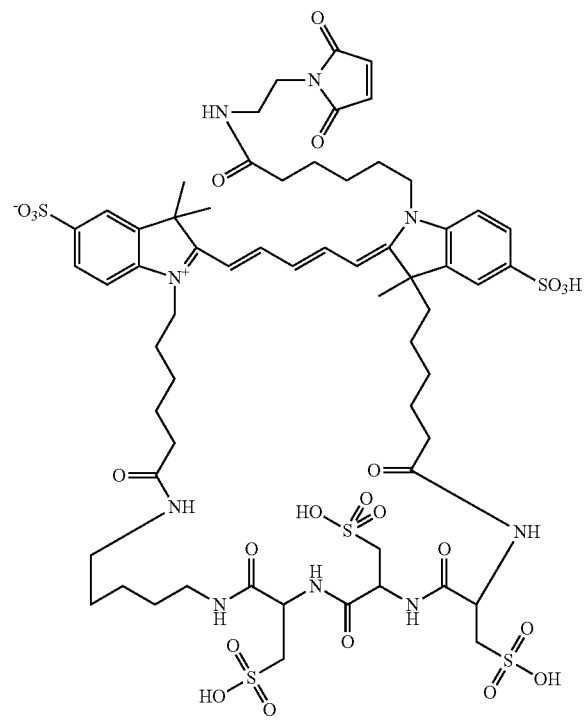

To Compound 34 (50 mg) in DMF (1 mL) at room temperature is added triethylamine (0.1 mL) and N-(2-aminoethyl)maleimide, trifluoroacetic acid salt (50 mg). The mixture is stirred at ambient temperature for 2 h. The solution mixture is poured into EtOAc (25 mL). The solid is centrifuged and washed with EtOAc (3×10 mL), ether (3×10 mL) and dried under vacuum to give crude Compound 40. The crude product is purified by preparative HPLC to yield the pure Compound 40 using 0.1% TFA in water-0.1% TFA in MeCN buffer system.

Example 41

Preparation of Compound 41

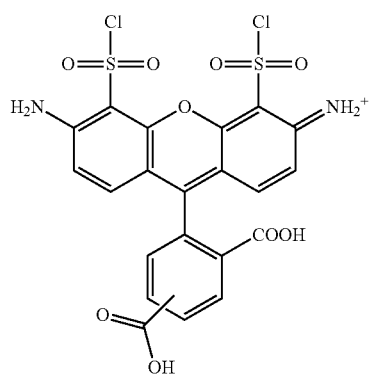

Compound 41 is prepared as described in U.S. Pat. Appl. No. 20080177086 (2008).

Example 42

Preparation of Compound 42

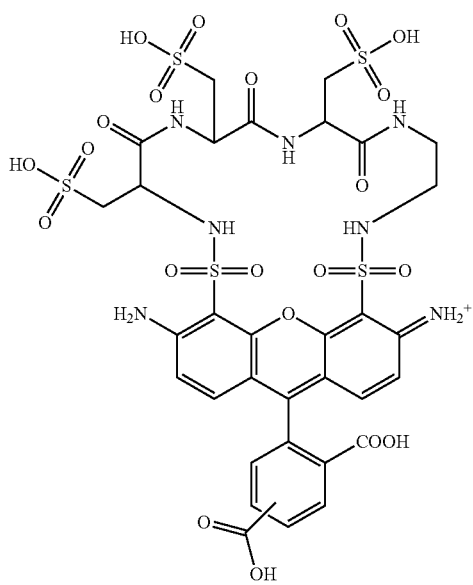

Compounds 41 (1 g) is dissolved in anhydrous DMF (50 mL). To DMF the solution of Compounds 41 is slowly added $Na_2CO_3$—$NaHCO_3$ solution of Compound 13 (150 mL, pH ~9.0), and is stirred at room temperature overnight. The reaction mixture is concentrated to ~5 mL, and dropwise added to 1:1 EtOAc-acetone (250 mL), and filtered to collect the precipitate. The solid is washed with EtOAc, and dried under high vacuum. The crude material is further purified by preparative HPLC to yield the pure Compound 42 using 0.1% TFA in water-0.1% TFA in MeCN buffer system.

Example 43

Preparation of Compound 43

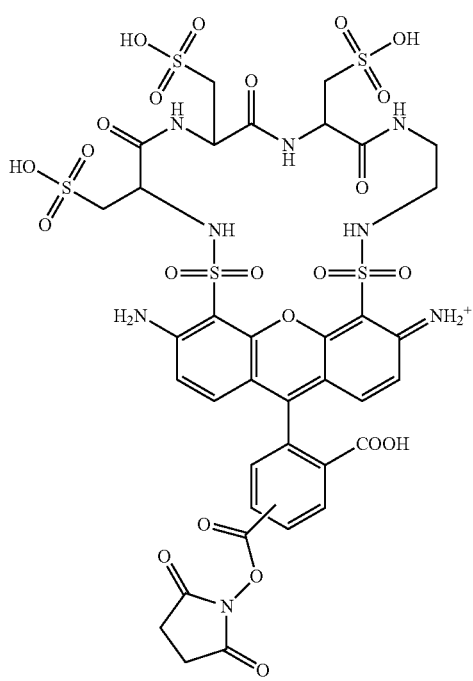

To a solution of Compound 42 (10 mg) in DMF (0.4 mL) is added O—(N-succinimidyl)-N,N,N',N'-tetramethyluronium tetrafluoroborate (10 mg), followed by triethylamine (0.1 mL). The mixture is stirred at room temperature for 1 h. The solution mixture is poured into EtOAc (15 mL). The solid is centrifuged and washed with EtOAc (3×10 mL), ether (3×10 mL) and dried under vacuum to give Compound 43.

Example 44

Preparation of Compound 44

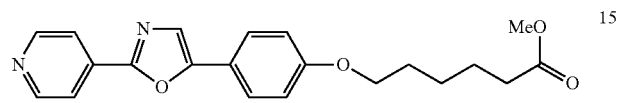

Compound 44 is prepared as described in U.S. Pat. Appl. No. 20070077549 (2009).

Example 45

Preparation of Compound 45

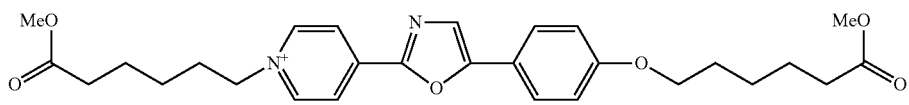 [SMILES: COC(=O)CCCCCOc1ccc(-c2cnc(-c3cc[n+](CCCCCC(=O)OC)cc3)o2)cc1]

Compound 44 (20 g) is suspended in 1,2-dichlorobenzene (30 mL). To the suspension is added methyl 6-bromohexanoate (30 mL). The reaction mixture is heated at ~130° C. until Compound 44 is mostly consumed. The reaction mixture is cooled to room temperature, and poured into EtOEt (500 mL). The EtOEt suspension is centrifuged to collect the precipitate that is washed with EtOEt. The crude material is further purified by a silica gel column to yield the pure Compound 45 using a gradient of chloroform/methanol.

Example 46

Preparation of Compound 46

Compound 45 (10 g) is suspended in concentrated $H_2SO_4$ (5 mL). To the suspension is added 20% fuming $H_2SO_4$ (10 ml). The reaction mixture is stirred at room temperature until the reaction is complete as indicated by TLC. To cold ether (500 ml) the reaction mixture is dropwise added with vigorous stirring to give the crude mixture of Compound 46 and its mono and diester. The crude material is suspended in 20% HCl, and heated at ~60° C. until the monoester and diester are mostly converted to the free acid. The crude material is further purified by preparative HPLC to yield the pure Compound 46 using 0.1% TFA in water-0.1% TFA in MeCN buffer system.

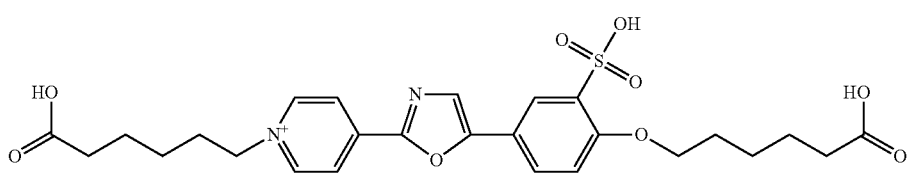 [SMILES: O=C(O)CCCCCOc1ccc(-c2cnc(-c3cc[n+](CCCCCC(=O)O)cc3)o2)cc1S(=O)(=O)O]

Example 47

Preparation of Compound 47

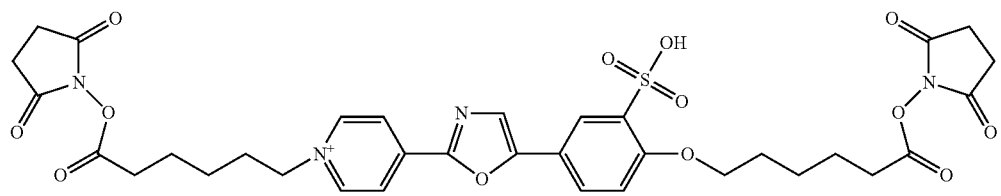 [SMILES: O=C(CCCCCOc1ccc(-c2cnc(-c3cc[n+](CCCCCC(=O)ON4C(=O)CCC4=O)cc3)o2)cc1S(=O)(=O)O)ON1C(=O)CCC1=O]

Compound 47 is analogously prepared from the reaction of Compound 46 with O—(N-succinimidyl)-N,N,N',N'-tetramethyluronium tetrafluoroborate according to the procedure of Compound 39.

Example 48

Preparation of Compound 48

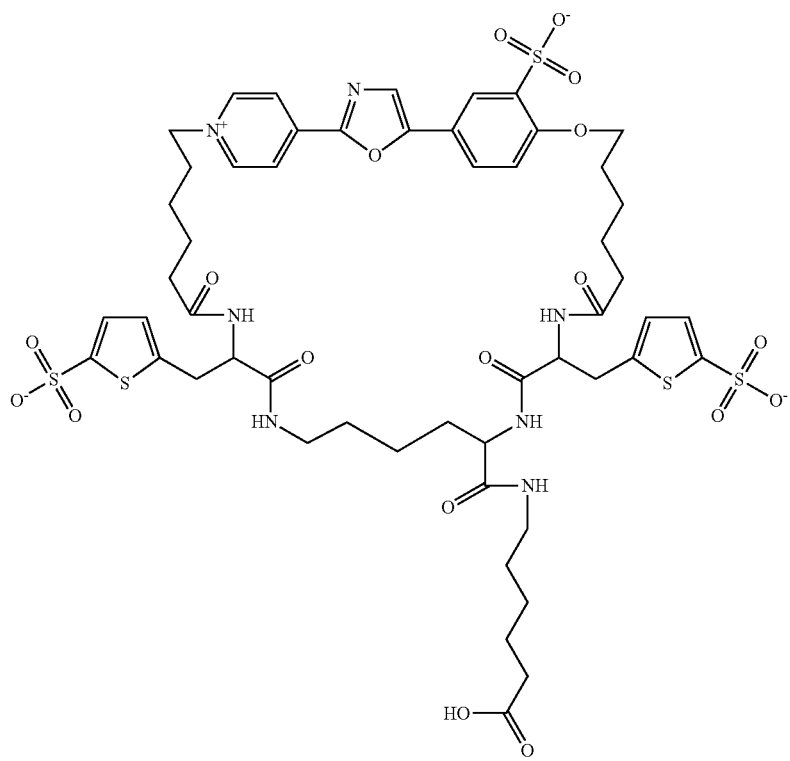 [SMILES: O=C(O)CCCCCNC(=O)C1CCCCNC(=O)C(Cc2ccc(S(=O)(=O)[O-])s2)NC(=O)CCCCC[n+]2ccc(cc2)-c2ncc(o2)-c2ccc(c(S(=O)(=O)[O-])c2)OCCCCCC(=O)NC(Cc2ccc(S(=O)(=O)[O-])s2)C(=O)N1]

The crude Compound 47 (4 g) is dissolved in anhydrous DMF (250 mL) and a solution of Compound 21 (3 g) in anhydrous DMF (250 mL) [neutralized with triethylamine to pH 8.0] is added slowly during the period of 8 h. The mixture is stirred at room temperature overnight. After removal of solvent, the residue is purified by preparative HPLC to yield the pure Compound 48 using 0.1% TFA in water-0.1% TFA in MeCN buffer system.

Example 49

Preparation of Compound 49

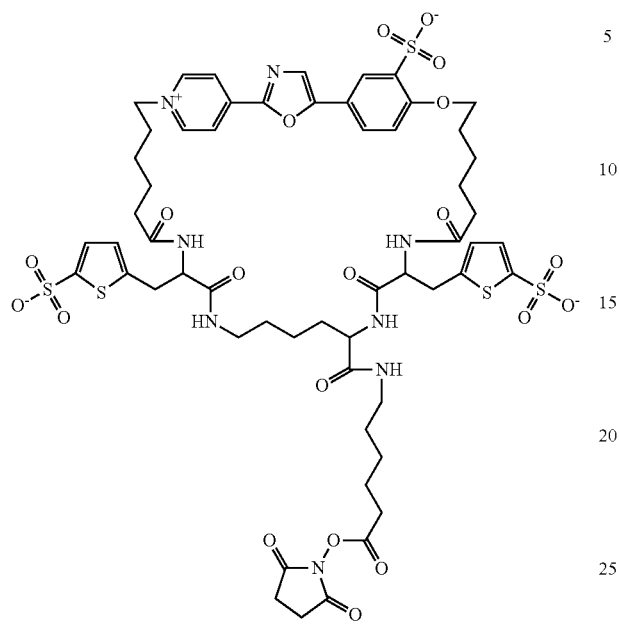

Compound 49 is analogously prepared from the reaction of Compound 48 with O—(N-succinimidyl)-N,N,N',N'-tetramethyluronium tetrafluoroborate according to the procedure of Compound 43.

Example 50

Preparation of Compound 50

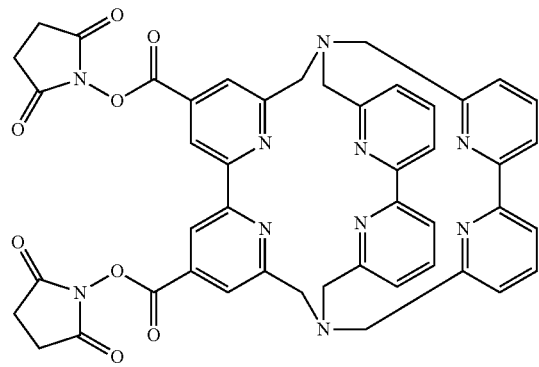 [SMILES: O=C(ON1C(=O)CCC1=O)c1cc2nc(c1)-c1cc(C(=O)ON3C(=O)CCC3=O)cc(n1)CN1Cc3cccc(n3)-c3cccc(n3)CN(Cc3cccc(n3)-c3cccc(n3)C1)C2]

Compound 50 is prepared as described in U.S. Pat. No. 5,162,508 (1992).

Example 51

Preparation of Compound 51

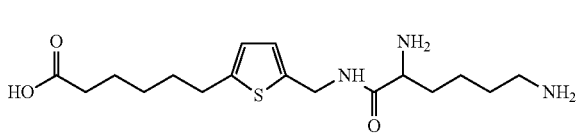 [SMILES: NCCCCC(N)C(=O)NCc1ccc(CCCCCC(=O)O)s1]

Compound 51 is analogously prepared from the reaction of Boc-Lys(Boc)-OH with 2-aminomethyl-5-(5'-carboxypentyl)thiophene according to the procedure of Compound 14.

Example 52

Preparation of Compound 52

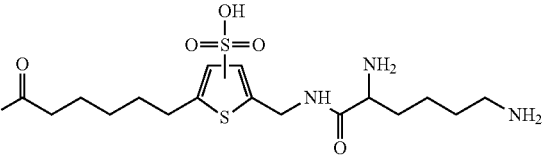

Compound 52 is analogously prepared from the sulfonation of Compound 51 according to the procedure of Compound 16.

Example 53

Preparation of Compound 53

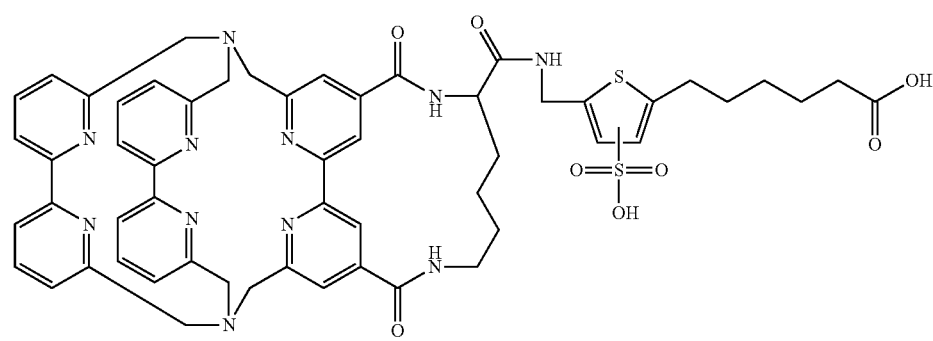

The crude Compound 50 (1 g) is dissolved in anhydrous DMF (250 mL) and a solution of Compound 52 (450 mg) in anhydrous DMF (250 mL) [neutralized with triethylamine to pH 8.0] is added slowly during the period of 10 h. The mixture is stirred at room temperature overnight. After removal of solvent, the residue is purified by preparative HPLC to yield the pure Compound 53 using 0.1% TFA in water-0.1% TFA in MeCN buffer system. The purified compound is redissolved in methanol, and neutralized with to pH 7.0. The evaporation of the solution gives Compound 53 as sodium salt.

Example 54

Preparation of Compound 54

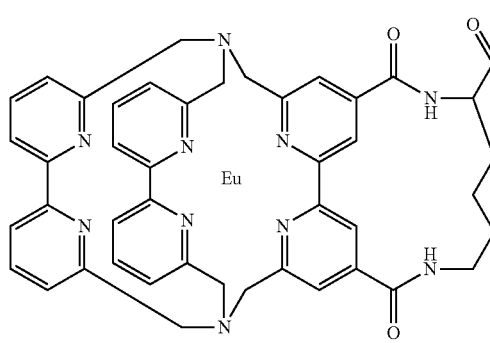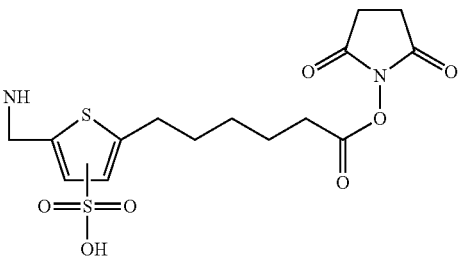

Compound 53 is in situ converted into its corresponding Eu complex with EuCl3 as described in U.S. Pat. No. 5,162,508 (1992). Compound 53-Eu complex (10 mg) and N,N'-disuccinimidyl carbonate (5 mg) are dissolved in DMF (0.5 ml). To the solution is added 4-dimethylaminopyridine (0.5 mg) and anhydrous pyridine (0.5 ml) under dry nitrogen protection with vigorous stiffing at room temperature. The reaction mixture is stirred under dry nitrogen protection at room temperature until the reaction is complete as indicated by HPLC. The reaction mixture is poured into ether, and the resulted precipitate is collected by filtration. The solid is washed with ether to yield the desired Compound 54.

Example 55

Preparation of a Peptide-Dye Conjugate

To aminophalloidin (5 mg) and the succinimidyl ester derivative Compound 34 (10 mg) in DMF (0.5 mL) is added N,N-diisopropylethylamine (25 μL). The mixture is stirred at room temperature for 3 hours. To this solution is added 5 mL of EtOAc. The solid is collected by centrifugation. The crude product is purified on SEPHADEX LH-20, eluting with water, followed by preparative HPLC to give the pure phalloidin conjugate. The product is an effective stain for F-actin filaments in fixed-cell preparations.

Example 56

Preparation of Protein-Dye Conjugates

A series of dye conjugates of goat anti-mouse IgG (GAM), goat anti-rabbit IgG (GAR), streptavidin, transferrin and other proteins, including R-phycoerythrin (R-PE) and allophycocyanin (APC) are prepared by standard means (Haugland, et al., METH. MOL. BIOL., 45, 205 (1995); Haugland, METH. MOL. BIOL., 45, 223 (1995); Haugland, METH. MOL. BIOL., 45,235 (1995); Haugland, CURRENT PROTOCOLS IN CELL BIOLOGY, 16.5.1-16.5.22 (2000)) using mono-succinimidyl ester or bis-succinimidyl ester compounds. The typical method for protein conjugation with succinimidyl esters of the invention is as follows. Variations in ratios of dye to protein, protein concentration, time, temperature, buffer composition and other variables that are well known in the art are possible that still yield useful conjugates. A solution of the protein is prepared at about 10 mg/mL in 0.1M sodium bicarbonate. The labeling reagents are dissolved in a suitable solvent such as DMF or DMSO at about 10 mg/mL. Water is a suitable solvent for many dyes of the invention. Predetermined amounts of the labeling reagents are added to the protein solutions with stiffing. A molar ratio of 10 equivalents of dye to 1 equivalent of protein is typical, though the optimal amount varies with the particular labeling reagent, the protein being labeled and the protein's concentration, and is determined empirically.

When optimizing the fluorescence yield and determining the effect of degree of substitution (DOS) on this brightness, it is typical to vary the ratio of reactive dye to protein over a several-fold range. The reaction mixture is incubated at room temperature for one hour or on ice for several hours. The dye-protein conjugate is typically separated from free unreacted reagent by size-exclusion chromatography, such as on Amersham PD-10 resin equilibrated with phosphate-buffered saline (PBS). The initial, protein-containing colored band is collected and the degree of substitution is determined from the absorbance at the absorbance maximum of each fluorophore, using the extinction coefficient of the free fluorophore. The dye-protein conjugate thus obtained can be subfractionated to yield conjugates with higher, lower or more uniform DOS.

Following is a specific example of using Compound 34 to prepare IgG-dye conjugate:

Step 1. Preparing Protein Solution (Solution A):
Mix 50 μL of 1M NaHCO3 with 450 μL of IgG protein solution (4 mg/mL) to give 0.5 mL protein sample solution. The resulted solution should have pH 8.5±0.5.

Step 2. Preparing Dye Solution (Solution B):
To 50 μL of DMSO add 1 mg of Compound 34, and stir until the compound is completely dissolved.

Step 3. Running Conjugation Reaction:
Add the dye solution (B) to the protein solution (A) with effective stirring or shaking, and keep the reaction mixture stirred or shaken for 1-3 hrs.

Step 4. Purifying the Conjugate:
a). Dilute 10× elution buffer with de-ionized water to give 1× elution buffer (Solution C) that is used to elute the protein conjugate from PD-10 column; b). Load the column with the reaction mixture (from step 3, filtrated if necessary) or supernatant as soon as the liquid in the pre-packed column runs just below the top surface; c). Add 1 mL of the 1× elution buffer as soon as the sample runs just below the top resin surface; Repeat this 'sample washing' process twice; Add more 1× elution buffer solution to elute the desired sample; d). Collect the faster-running band that is usually the desired labeled protein. Keep the slower-running band that is usually free or hydrolyzed dye until the desired product is identified.

Step 5. Characterizing the Desired Dye-Protein Conjugate:
a). Measure OD (absorbance) at 280 nm and dye maximum absorption wavelength (Note: for most spectrophotometers, the sample (from the column fractions) need be diluted with de-ionized water so that the OD values are in the range 0.1 to 0.9). The O.D. (absorbance) at 280 nm is the maximum absorption of protein (Note: to obtain accurate DOS, you must make sure that the conjugate is free of the non-conjugated dye); b). Calculating DOS using the following equation:

$$DOS=[dye]/[protein]=A_{dye} \times \epsilon_p/250000(A_{280}-CF \times A_{dye})$$

[dye] is the dye concentration, and can be readily calculated from the Beer-Lambert Law: $A=\epsilon_{dye}C \times L$; [protein] is the target protein concentration. This value can be either estimated by the weight (added to the reaction) if the conjugation efficiency is high enough (preferably >70%) or more accurately calculated by the Beer-Lambert Law: $A=\epsilon_{protein}C \times L$. For example, IgG has the c value to be 203,000 $cm^{-1}M^{-1}$. CF is the dye correct factor, and calculated by the ratio of $OD_{280}$ $nm/OD_{dye\ maximum\ absorption\ wavelength}$.

Example 57

Fluorescent Labeling of Periodate-Oxidized Proteins

Two samples of 5 mg each of goat IgG antibody in 1 mL of 0.1M sodium acetate, 0.135 M NaCl, pH 5.5, are treated with 2.1 mg of sodium metaperiodate on ice, for 1 and 2 hours, respectively. The reactions are stopped by addition of 30 µL ethylene glycol. The antibodies are purified on a Sephadex G25 column packed in PBS pH 7.2. One-tenth volume of 1M sodium bicarbonate is added to raise the pH and Compound 102 or 117 is added at a molar ratio of dye to protein of 50:1. The reaction is stirred for 2 hours at room temperature. Sodium cyanoborohydride is added to a final concentration of 10 mM and the reaction is stirred for 4 hours at room temperature. The antibody conjugates are purified by dialysis and on Sephadex G25 columns as described above. Antibodies that are oxidized for 1 hour typically yield a degree of substitution of 1 mole of dye per mole of IgG. Antibodies that are oxidized for 2 hours typically yield a DOS of approximately 2 mole of dye per mole of IgG. Periodate-oxidized proteins in gels and on blots can also be labeled, essentially as described in Estep et al., ANAL. BIOCHEM., 157, 100-105 (1986).

Example 58

Labeling Beta-Galactosidase with a Thiol-Reactive Dye

A solution of beta-galactosidase, a protein rich in free thiol groups, is prepared in PBS (2.0 mg in 400 µL). The protein solution is then treated with a 20 mg/L solution of the maleimide derivative Compound 40 in DMF. Unreacted dye is removed on a spin column. The degree of substitution by the dye is estimated using the extinction coefficient of the free dye as described in Example 56. The protein concentration is estimated from the absorbance at 280 nm, corrected for the absorbance of Compound 40 at that wavelength.

Example 59

Comparison of the Protein Conjugates Prepared from Non-Crosslinked Dyes with the WSB-Crosslinked Dyes Dye-protein conjugates are synthesized as described in Example 56 and conjugated to GAR at various DOS. FIGS. 1-3 are the direct comparison of fluorescence properties of GAR conjugates prepared from non-crosslinked dye SE, dye SE crosslinked with a hydrophobic bridge, and dye SE crosslinked with a WSB of this invention. One can see that the WSB-corsslinking has resulted in a significant improvement of fluorescence performance of dye compounds. The brighter fluorescence emission of WSB compounds is observed at all of the tested DOS's.

Example 60

Fluorescence Energy Transfer In Conjugates of R-Phycoerythrin and Allophycocyanin R-phycoerythrin (R-PE) conjugate of dye SE compounds is prepared as in Example 56 with a DOS sufficiently high to quench the donor fluorescence almost completely (DOS about 4-8). The resulting phycobiliprotein conjugate is excited at 488 nm and the fluorescence emission is compared to that of unmodified R-phycoerythrin excited at the same wavelength. Highly efficient energy transfer (>99%) occurs from the protein to the fluorescent dye. A conjugate of these complexes with streptavidin is prepared essentially as described by Haugland (METH. MOL. BIOL., 45, 205 (1995)). This streptavidin conjugate retains the energy transfer properties and is useful for cell staining in flow cytometers that utilize the argon-ion laser for excitation. Tandem conjugates of allophycocyanin can also be made, with longer wavelength dyes of the invention such as Compound 34 or 39 yield emission well beyond 700 nm when excited near 633 nm.

Example 61

Labeling of Actin in Cultured Mammalian Cells

Bovine pulmonary artery cells (BPAEC) are grown to 30-50% of confluence on glass. The cells are fixed with 3.7% formaldehyde, permeabilized with 0.2% Triton X-100, and blocked with 6% BSA. The cells are incubated with the phalloidin dye-conjugate of Example 55. The cells are rinsed with blocking buffer and mounted in PBS pH 7.4. The stained cells display actin filaments decorated with red fluorescence.

Example 62

Preparation and Use of a Fluorescent Tyramide

A 2-fold molar excess of tyramine hydrochloride is added to Compound 34 in aqueous solution at room temperature followed by an excess of triethylamine. After 30 minutes the red solid is precipitated with acetone, washed with ether and purified by preparative HPLC. Bovine pulmonary artery cells (BPAEC) are grown to 30-50% of confluence on glass. The cells are fixed with 3.7% formaldehyde, permeabilized with 0.2% Triton X-100, and blocked with 1 mg/mL streptavidin and 1 mM biotin. After washing, cells are exposed to about 0.05 µg/mL of biotinylated anti-cytochrome C oxidase (anti-COX) then incubated with Streptavidin-HRP conjugate at room temperature. Cells are rinsed again. The sample is then incubated with Compound 34 tyramide and examined using fluorescence microscopy.

Example 63

Preparation of Aminodextran Dye-Conjugates 70,000 MW aminodextran (50 mg) derivatized with an average of 13 amino groups is dissolved at 10 mg/mL in 0.1M $NaHCO_3$. A dye SE compound is added to give a dye/dextran ratio of about 10-15. After 6-12 hours the conjugate is purified on SEPHADEX G-50, eluting with water. Typically 4-6 moles of dye are conjugated to 70,000 MW dextran.

Example 64

Preparation of Fluorescent-Dye Labeled Microspheres

Uniform microspheres are chemically modified to have functional groups such as amino or carboxyl or aldehydes. These functionalized microspheres are covalently conjugated with the corresponding reactive dyes as listed in Table 1. For example, the amine-modified microspheres are readily conjugated to the dyes of the invention through succinimidyl esters such as Compounds 34, 39, 49 and 54. A dye-labeled protein is covalently coupled through its amine residues to the carboxylate groups of the polymer using ethyl 3-(dimethylaminopropyl)carbodiimide (EDAC).

Example 65

Preparation of Dye-Bacteria Conjugates

Heat-killed *Escherichia coli* are suspended at 10 mg/mL in pH 8-9 buffer, and incubated with 0.5-1.0 mg/mL of an amine-reactive dye, typically a succinimidyl ester derivative (such as Compound 34, 39, 49 and 54). After 30-60 minutes the labeled bacteria are centrifuged and washed several times with buffer to remove any unconjugated dye. Labeled bacteria is analyzed by flow cytometry.

Example 66

Preparation of Nucleotide-Dye Conjugates

To 2 mg of 5-(3-aminoallyl)-2'-deoxyuridine 5'-triphosphate (Sigma Chemical) in 100 µL water is added Compound 34, 39, 49 or 54 in 100 µL DMF and 5 µL triethylamine. After 3 hours, the solution is evaporated and the residue is purified by HPLC. The product fractions are lyophilized to give fluorescent nucleotide conjugate. Alternatively, fluorescent dye-conjugates of deoxyuridine 5'-triphosphate are prepared from 5-(3-amino-1-propynyl)-2'-deoxyuridine 5'-triphosphate, or by treating a thiolated nucleotide or a thiophosphate nucleotide with a thiol-reactive dye of the invention (such as Compound 101). Additionally, 2'-(or 3')-2-aminoethylaminocarbonyladenosine 5'-triphosphate is reacted with a slight excess of Compound 34, 39, 49 or 54 and, following precipitation with ethanol, the ribose-modified product is purified by preparative HPLC. Additional nucleotides conjugated with the dyes of invention can be readily prepared by someone skilled in the art following the published procedures such as Nimmakayalu M, et al., BIOTECHNIQUES, 28, 518-522 (2000); Giaid A, et al. HISTOCHEMISTRY, 93, 191-196 (1989).

Example 67

Preparation of an Oligonucleotide Dye-Conjugate

A 5'-amine-modified, 18-base M13 primer sequence (about 100 µg) is dissolved in 4 µL water. To this is added 250 µg of Compound 34, 39, 49 or 54 in 100 µL 0.1M sodium borate, pH 8.5. After 16 hours, 10 µL of 5 M NaCl and 3 volumes of cold ethanol are added. The mixture is cooled to −20° C., centrifuged, the supernatant is decanted, the pellet is rinsed with ethanol and then dissolved in 100 µL water. The labeled oligonucleotide is purified by HPLC. The desired peak is collected and evaporated to give the fluorescent oligonucleotide.

Example 68

In Situ Hybridization of an RNA Probe

Mouse fibroblasts are fixed and prepared for mRNA in situ hybridization using standard procedures. A dye-labeled RNA probe is prepared by in vitro transcription of a plasmid containing the mouse actin structural gene cloned downstream of a phage T3 RNA polymerase promoter. Labeling reactions comprise combining 2 µL DNA template (1 µg DNA), 1 µL each of 10 mM ATP, CTP and GTP, 0.75 µL 10 mM UTP, 2.5 µL 1 mM aminoallyl-labeled UTP, 2 µL 10× transcription buffer (400 mM Tris, pH 8.0, 100 mM $MgCl_2$, 20 mM spermidine, 100 mM NaCl), 1 µL T3 RNA polymerase (40 units/µL), 1 µL 2 mg/mL BSA, and 8.75 µL water. Reactions are incubated at 37° C. for two hours. The DNA template is removed by treatment with 20 units DNase I for 15 minutes, at 37° C. The RNA transcript is purified by extraction with an equal volume of phenol:chloroform, 1:1, and then by chromatography on SEPHADEX G50. Labeled RNA is denatured for 5 minutes at 50° C., and then hybridized to cellular preparations using standard procedures.

Example 69

Preparing DNA Hybridization Probes Using Amine-Modified DNA and an Amine-Reactive Dye of the Invention Nick translation is performed using pUC1.77 plasmid DNA containing a chromosome 1 human alpha-satellite probe. To a microcentrifuge tube is added, in the following order: 23.5 µL water, 5 µL 10× Nick Translation buffer (0.5 M Tris-HCl, 50 mM $MgCl_2$, 0.5 mg/mL BSA, pH 7.8), 5 µL 0.1M DTT, 4 µL d(GAC)TP mix (0.5 mM dATP, 0.5 mM dCTP, 0.5 mM dGTP), 1 µL 0.5 mM dTTP, 4 µL 0.5 mM aminoallyl-dUTP, 1 µL 1 µg/µL template DNA, 5 µL DNase I (1 µg/mL, 2000 Kunitz units/mg), 1.5 µL DNA polymerase I (10 U/µL). The tube is incubated 2 hours at 15° C., then brought to a final volume of 100 µL with water. The amine-modified DNA is purified using a QIAQUICK PCR purification Kit (Qiagen). The amine-modified DNA is resuspended in 5 µL water. To the solution is added 3 µL 25 mg/mL sodium bicarbonate and 50 µg of Compound 34, 39, 49 or 54 in 5 µL DMF. The reaction is incubated for 1 hour at room temperature in the dark, to the reaction is added 90 µL water, and it is purified using a Qiagen PCR purification kit. The labeled DNA products are suitable for in situ hybridization experiments, use on microarrays and as fluorescence donors or acceptors in hybridization-based assays.

Example 70

Staining Cells with Tandem Dye-Labeled Streptavidin

Jurkat cells are washed twice with 1% BSA/PBS and resuspended at a concentration of $1 \times 10^7$ cells/mL. The Jurkat cells are then incubated on ice for 60 minutes with mouse anti human CD4 biotin at the recommended concentration of 10 µL for $1 \times 10^6$ cells. After incubation with the primary antibody, the cells are washed with 1% BSA/PBS and incubated on ice for 30 minutes with the fluorescent streptavidin-phycoerythrin conjugate of Example 59. The cells are washed with 1% BSA/PBS, centrifuged, and resuspended with 400 µL of 1% BSA/PBS. The samples are analyzed on a BD Calibur flow cytometer exciting with the 488 nm line of an argon laser or 633 nm line of an He—Ne laser, collecting the emission by a long pass filter. Using a FSC versus SSC dot plot the live cells are gated and the geometric mean of the fluorescence is measured. The data is analyzed for both fluorescence intensity and signal/noise ratio.

Example 71

Characterization of CD4, CD 8 and CD45 Conjugates by Flow Cytometry

Figure 10:
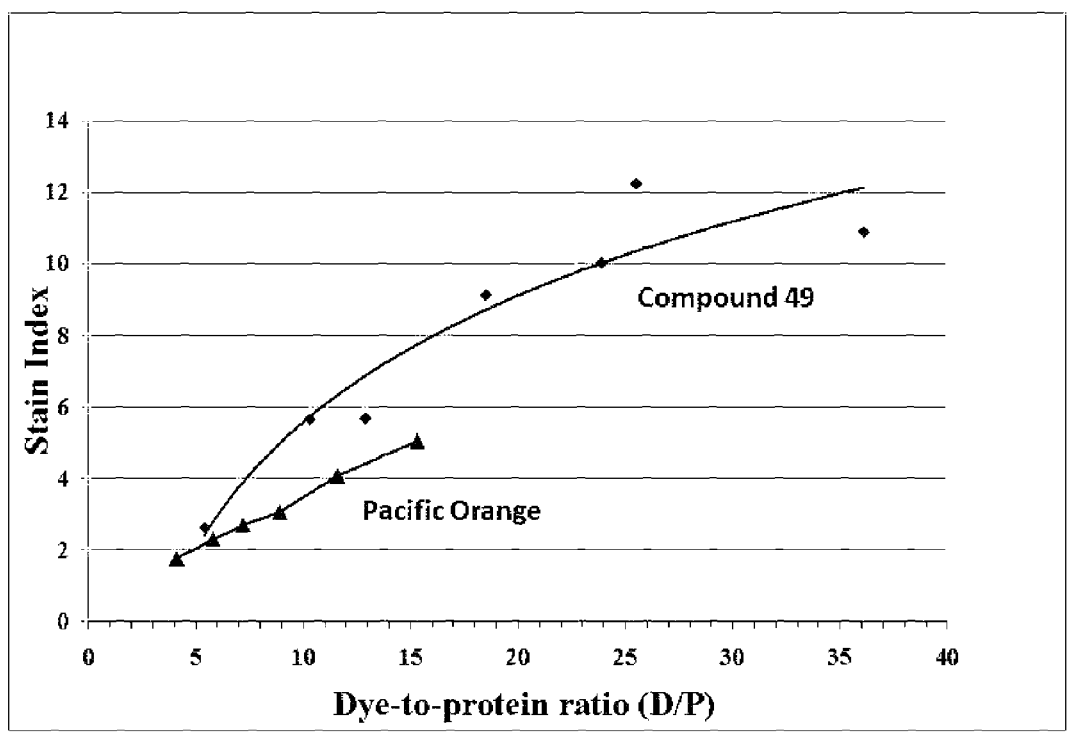

Normal human blood, collected in EDTA, is incubated at ambient temperature for 30 minutes with the mouse anti human CD4, CD 8 or CD45 conjugates of Compound 34, 39, 43 or 49 at the concentration of 1 µg for 1.1 ml of blood. After incubation with the antibody conjugate, the blood is suspended in a 20-fold volume (2 ml) of BD FACSLysing Solution and incubated for 8-10 minutes at ambient temperature. The samples are centrifuged at 2-300×g for 5 minutes, the supernatant is decanted and the pellet is suspended and washed with 2 ml of 0.5% BSA/PBS. The supernatant is again decanted and the pellet is suspended in 0.5 ml of 0.5% BSA/PBS for analysis on a BD LSRII Flow Cytometer. The analysis is performed such that the samples are excited with the 405 nm line of a violet laser, 488 nm line of an argon laser or 633 nm line of an He—Ne laser, collecting the emission a proper bandpass filter. Using a FSC versus SSC dot plot the lymphocytes are gated and the median fluorescence is measured. FIG. 10 indicates that mouse anti human CD4, CD8 and CD45 conjugates are highly fluorescent, giving good staining signal for cell analysis.

What is claimed is:

1. A chemically reactive luminescent dye having the formula:

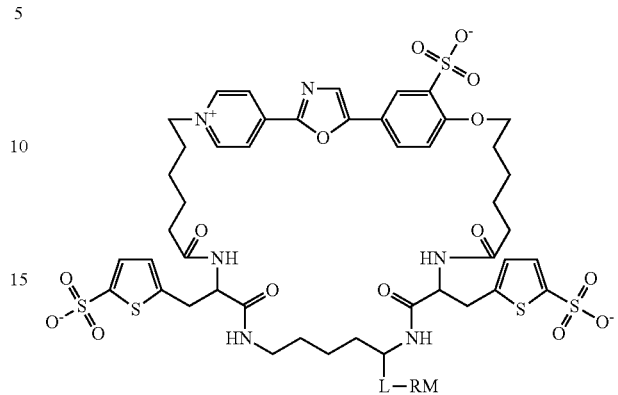

wherein L is a linker of 0-30 atoms length; and RM is an amine, a carboxylic acid, an activated ester of a carboxylic acid, a haloacetamide, a hydrazine, a hydroxylamine, an isothiocyanate, a maleimide, or a sulfonyl halide.

2. A luminescent dye conjugate having the formula:

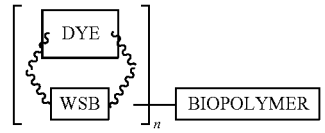

wherein WSB is a water-soluble bridge comprising at least a sulfonate or a phosphonate group; BIOPOLYMER is a biological substance having a molecular weight of larger than 1000 daltons; n is an integer of 1-30 provided that the dye is covalently connected to the BIOPOLYMER directly or indirectly via a linker "L"; and L is a linker of 0-30 atoms in length; and wherein said luminescent dye conjugate is derived from the reaction of:

a chemically reactive luminescent dye having the Formula:

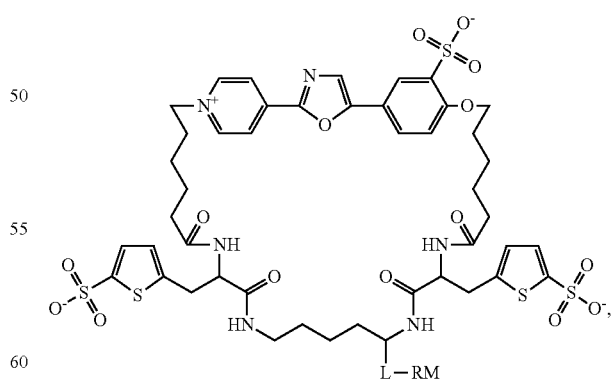

wherein L is the linker of 0-30 atoms length, and RM is an amine, a carboxylic acid, an activated ester of a carboxylic acid, a haloacetamide, a hydrazine, a hydroxylamine, an isothiocyanate, a maleimide, or a sulfonyl halide; and the BIOPOLYMER.

3. The conjugate of claim 2 wherein the BIOPOLYMER is a peptide, a protein, a polysaccharide, an oligonucleotide, a nucleic acid, a lipid, a phospholipid, a lipoprotein, a lipopolysaccharide, a liposome, a lipophilic polymer, a polymeric microparticle, an animal cell, a plant cell, a bacterium, a yeast, or a virus.

4. The conjugate of claim 2 wherein the BIOPOLYMER is an antibody.

* * * * *